United States Patent
Suzuki et al.

(10) Patent No.: US 11,781,146 B2
(45) Date of Patent: Oct. 10, 2023

(54) VECTOR INCLUDING A TRANSLATION-IMPAIRED DIHYDROFOLATE REDUCTASE GENE CASSETTE AND UBIQUITOUSLY ACTING CHROMATIN OPENING ELEMENT

(71) Applicants: National University Corporation Hokkaido University, Hokkaido (JP); Fuso Pharmaceutical Industries, Ltd., Osaka (JP)

(72) Inventors: Yasuhiko Suzuki, Hokkaido (JP); Miki Nakagawa, Hokkaido (JP); Yayoi Kameda, Hokkaido (JP); Satoru Konnai, Hokkaido (JP); Tomohiro Okagawa, Hokkaido (JP); Naoya Maekawa, Hokkaido (JP); Shinya Goto, Hokkaido (JP); Yamato Sajiki, Hokkaido (JP); Kazuhiko Ohashi, Hokkaido (JP); Shiro Murata, Hokkaido (JP); Yuzuru Kitahara, Tokyo (JP); Keiichi Yamamoto, Osaka (JP)

(73) Assignees: NATIONAL UNIVERSITY CORPORATION HOKKAIDO UNIVERSITY, Hokkaido (JP); FUSO PHARMACEUTICAL INDUSTRIES, LTD., Osaka (JP)

( * ) Notice: Subject to any disclaimer, the term of this patent is extended or adjusted under 35 U.S.C. 154(b) by 356 days.

(21) Appl. No.: 17/054,935

(22) PCT Filed: May 13, 2019

(86) PCT No.: PCT/JP2019/018899
§ 371 (c)(1),
(2) Date: Nov. 12, 2020

(87) PCT Pub. No.: WO2019/225372
PCT Pub. Date: Nov. 28, 2019

(65) Prior Publication Data
US 2021/0254079 A1 Aug. 19, 2021

(30) Foreign Application Priority Data

May 24, 2018 (JP) .................................. 2018-099704
Sep. 10, 2018 (JP) .................................. 2018-168591

(51) Int. Cl.
*C12N 15/67* (2006.01)
*C12N 15/66* (2006.01)
*C12N 15/85* (2006.01)

(52) U.S. Cl.
CPC ............. *C12N 15/67* (2013.01); *C12N 15/66* (2013.01); *C12N 15/85* (2013.01); *C12Y 105/01003* (2013.01)

(58) Field of Classification Search
CPC ........ C12N 15/67; C12N 15/66; C12N 15/85; C12N 2800/107; C12N 2830/46; C12N 9/003; C12N 15/68; C12Y 105/01003; C07K 14/70521; C07K 2317/14; C07K 2319/30; C07K 16/32; C07K 2317/24; C07K 16/4291; C07K 16/00; C12P 21/02; C12P 21/00; C12Q 1/04
See application file for complete search history.

(56) References Cited

U.S. PATENT DOCUMENTS

| | | | |
|---|---|---|---|
| 2003/0166890 A1* | 9/2003 | Crombie | C12N 15/85 536/23.1 |
| 2004/0161817 A1 | 8/2004 | Benton et al. | |
| 2006/0141577 A1 | 6/2006 | Otte et al. | |
| 2012/0122083 A1 | 5/2012 | Tahara et al. | |

FOREIGN PATENT DOCUMENTS

| | | | |
|---|---|---|---|
| JP | 2004-535189 | 11/2004 | |
| JP | 2008-518613 | 6/2008 | |
| JP | 2010-42033 | 2/2010 | |
| JP | 5704753 | 4/2015 | |
| JP | 5704753 B2 * | 4/2015 | ............. C12N 15/85 |

OTHER PUBLICATIONS

JP_5704753_B2 English Translation (Year: 2015).*
Extended European Search Report dated Feb. 21, 2022 in corresponding European Patent Application No. 19806394.3.
Jing Aileen et al: "Investigation of Post-Translational Strategies to Enhance Recombinant Human Bone Morphogenetic Protein-2 Production in Mammalian Cell Culture", Thesis, Jan. 1, 2014(Jan. 1, 2014), pp. ii-xviii, 1-196, XP055776686.
Benton T et al: "The Use of UCOE Vectors in Combination With a Preadapted Serum Free, Suspension Cell Line Allows for Rapid Production of Large Quantities of Protein", Cytotechnology, Springer Netherlands, Dordrecht, vol. 38, No. 1-03, Jan. 1, 2002(Jan. 1, 2002), pp. 43-46, XP008053158.

(Continued)

Primary Examiner — Neil P Hammell
Assistant Examiner — Morgan T Lindgren Baltzell
(74) Attorney, Agent, or Firm — Wenderoth, Lind & Ponack, L.L.P.

(57) ABSTRACT

The present invention provides mammalian cell expression vectors that impart to mammalian host cells an ability to produce high levels of foreign gene-derived proteins. A ubiquitously acting chromatin opening element (UCOE) is introduced into an expression vector that has a plasmid DNA integrated into a transcriptional hot spot on the chromosome of a dihydrofolate reductase gene-deficient host cell so that it allows for selection of strains that grow in hypoxanthine-thymidine (hereinafter denoted as HT)-free medium, whereby transformants will produce a protein of interest in increased amounts.

20 Claims, 14 Drawing Sheets

Specification includes a Sequence Listing.

(56) References Cited

OTHER PUBLICATIONS

Ayyappan R Nair et al: "Effect of different UCOE-promoter combinations in creation of engineered cell lines for the production of Factor VIII", BMC Research Notes, Biomed Central Ltd, GB, vol. 4, No. 1, Jun. 10, 2011 (Jun. 10, 2011), p. 178, XP021104275.
Betts Zeynep et al: "Assessment of UCOE on Recombinant EPO Production and Expression Stability in Amplified Chinese Hamster Ovary Cells", Molecular Biotechnology, vol. 57, No. 9 Jun. 19, 2015 (Jun. 19, 2015), pp. 846-858, XP055889696.
International Search Report (ISR) dated Jun. 18, 2019 in International (PCT) Application No. PCT/JP2019/018899.
English Translation of International Preliminary Report on Patentability dated Sep. 2, 2020 in PCT Application No. PCT/JP2019/018899.

\* cited by examiner

Fig. 1. pDC62c5-U533

Fig. 2. pDC62c5-U533-OMLH

Fig. 3. pDC61-OMLH

Fig. 4. pNC32c-U533-OMLH

Fig. 5. UCOE-Hu-P2-OMLH

Fig. 8. pDC62cs-US33 with only one site for foreign gene insertion

Fig. 11. pDC62c5-U533-TRLH

VECTOR INCLUDING A TRANSLATION-IMPAIRED DIHYDROFOLATE REDUCTASE GENE CASSETTE AND UBIQUITOUSLY ACTING CHROMATIN OPENING ELEMENT

TECHNICAL FIELD

The present invention relates to novel vectors and use thereof. More specifically, the present invention relates to mammalian cell expression vectors that impart to mammalian host cells an ability to produce high levels of foreign gene-derived proteins. The expression vectors of the present invention are particularly suitable for production of mammalian proteins that rarely exhibit adequate activity upon genetic recombination using *E. coli* or yeast as host and which require glycosylation and folding that are unique to mammals.

BACKGROUND ART

A large number of vectors have been developed for producing recombinant proteins and the expression levels of proteins are high in expression systems where bacteria typified by *E. coli*, eukaryotic microorganisms typified by yeast, and insect cells are used as host. However, in the case of expressing proteins that are unique to mammals, they may not form a normal three-dimensional structure and, most of the time, present a problem with post-translational modifications such as glycosylation. Thus, it is necessary to establish expression systems that use mammalian cells as host, but in most cases, the expression level is generally low. As for animal cells which are in a higher form of life than insect cells, expression systems involving recombinant virus vectors are also used but removing recombinant virus vectors from the expressed proteins is a very cumbersome process and the risk of the virus vectors themselves cannot be denied.

Cases of recombinant protein production using a mammalian cell as host include tissue plasminogen activator (Patent Document No. 1), erythropoietin (Patent Document No. 2 and Non-Patent Documents Nos. 1-3), IFN-γ (Non-Patent Document No. 4), and IFN-β (Patent Document No. 3 and Non-Patent Document No. 5). Furthermore, there are many reports on recombinant production of monoclonal antibodies (Patent Documents Nos. 4-6, and Non-Patent Documents Nos. 6-8). In addition, an example of a high expression vector for mammalian cells is pNOW/CMV-AA (Patent Document No. 7). The production level of conglutinin using this vector was up to 11.8 μg/mL after four days of culture. However, it can hardly be assumed that the production level of recombinant proteins is sufficient in these cases.

The manufacture of pharmaceutical agents using mammalian cells, particularly Chinese hamster ovary cells (hereinafter, CHO cells) has been confirmed to be safe and is currently a common technique. In the manufacture of recombinant proteins using mammalian cells, a higher productivity is very important from such aspects as cost reduction and medical bill saving. To this end, it is essential to develop expression vectors for producing transformants with high-level production ability through efficient gene transfer.

To facilitate high-level production of recombinant proteins in mammalian cells, efficient gene transfer is necessary. Efficient gene transfer means high probability of obtaining clones with high-level productivity in spite of the ease with which clone selection can be achieved. Specifically, the following are meant: with respect to all transformed cells, the number of viable cell clones after drug selection is relatively small, which makes it easy to select clones with high-level productivity; what is more, in spite of the small number of cells that produce the protein of interest, the expected value for the emergence of clones with high-level productivity is high. As more cells are obtained, the time and labor that are required for selection are increased correspondingly, which leads not only to lower efficiency but also to high likelihood of overlooking clones that potentially have high-level production capacity.

High-level production capacity refers to high expression level of recombinant protein in the transformed cell clones obtained by gene transfer, and this is considered to be mainly due to the characteristics and performance of the expression vectors. It has been shown that the level of gene expression differs considerably depending on the chromosomal position (Non-Patent Document No. 9), and introduction of a gene of interest into a region on the chromosome that has high transcriptional activity (hereinafter, a transcriptional hot spot) will predictably increase the level of recombinant protein production.

Suzuki et al. have successfully developed expression vectors that have a plasmid DNA integrated into a transcriptional hot spot on the chromosome of a dihydrofolate reductase gene-deficient host cell and which have a mechanism that allows for selection as strains that grow in a hypoxanthine-thymidine (HT)-free medium (Patent Document No. 8). Being necessary for biosynthesis of nucleobases, dihydrofolate reductase (DHFR) is an enzyme essential for all organisms that use DNA as a genetic information material. Therefore, dihydrofolate reductase gene-deficient host cells cannot grow in a medium that does not contain HT which is a component of nucleic acids. When a construct into which the gene of a protein of interest and the DHFR gene have been integrated is introduced into dihydrofolate reductase gene-deficient host cells and if these cells are cultured under HT-free conditions, cells that express the protein of interest can be selected. This method, compared to the one that comprises introducing a construct incorporating the gene of a protein of interest and the neomycin phosphotransferase gene and then performing selection with G418, allows gene amplification by MTX which is a DHFR inhibitor and is therefore more suitable for obtaining strains producing the protein of interest at high levels. As a result, an expression vector enabling high-level and stable protein production could be constructed.

PRIOR ART LITERATURE

Patent Documents

Patent Document No. 1: Japanese Unexamined Patent Publication S59-183693

Patent Document No. 2: Japanese Unexamined Patent Publication 2002-45191

Patent Document No. 3: Japanese Unexamined Patent Publication H7-265084

Patent Document No. 4: Japanese Unexamined Patent Publication H7-67648

Patent Document No. 5: Japanese Unexamined Patent Publication H6-30788

Patent Document No. 6: Japanese Unexamined Patent Publication H6-217786
Patent Document No. 7: Japanese Unexamined Patent Publication H10-179169
Patent Document No. 8: Japanese Patent No. 5704753

Non-Patent Documents

Non-Patent Document No. 1: Fermentation Bioengineering, 4, p. 257, 1989
Non-Patent Document No. 2: Proc. Natl. Acad. Sci. USA, 83, p. 6465, 1986
Non-Patent Document No. 3: Biotechnology, 6, p. 67, 1988
Non-Patent Document No. 4: Proc. Natl. Acad. Sci. USA, 80, p. 4564, 1983
Non-Patent Document No. 5: Cytotechnology, 4, p. 173, 1990
Non-Patent Document No. 6: Biotechnology, 10, p. 169, 1992
Non-Patent Document No. 7: J. Immunol. Methods, 125, p. 191, 1989
Non-Patent Document No. 8: Biotechnology, 10, p. 1455, 1992
Non-Patent Document No. 9: Annu. Rev. Cell Biol., 6, p. 679, 1990

DISCLOSURE OF THE INVENTION

Problem for Solution by the Invention

It is an object of the present invention to provide expression vectors for mammalian cells which impart to mammalian host cells an ability to produce foreign gene-derived proteins at high levels. It is another object of the present invention to provide a method of preparing transformants using the above expression vectors, as well as a method of producing foreign gene-derived proteins using the above expression vectors.

Means to Solve the Problem

The present inventors introduced a ubiquitously acting chromatin opening element (UCOE) into the above-described expression vector developed by Suzuki et al. which had a plasmid DNA integrated into the transcriptional hot spot on the chromosome of a dihydrofolate reductase gene-deficient host cell and which had a mechanism that would allow for selection as strains growing in HT-free medium; as a result, the present inventors have succeeded not only in increasing the production levels of proteins of interest in transformants but also in enhancing the stability of their expression The present invention is summarized as follows.
(1) An expression vector comprising the following (a), (b) and (c):
(a) a translation-impaired dihydrofolate reductase gene cassette (translation-impaired DHFR gene cassette) comprising a region with altered codons, wherein the altered codons comprise GCA for alanine, CGA for arginine, AAU for asparagine, GAU for aspartic acid, UGU for cysteine, CAA for glutamine, GAA for glutamic acid, GGU for glycine, CAU for histidine, UUA for leucine, AAA for lysine, CCA for proline, UUU for phenylalanine, UCA for serine, ACU for threonine, UAU for tyrosine, and/or GUA for valine, and wherein the region with altered codons accounts for 30% or more of the full length of the DHFR gene from the 5' end of the DHFR gene;
(b) a gene cassette comprising a cloning site for integration of a foreign gene that is located between a transcriptionally active promoter and a stable polyadenylation signal; and
(c) a ubiquitously acting chromatin opening element (UCOE).
(2) The expression vector of (1) above, wherein the translation-impaired DHFR gene cassette of (a) uses a promoter derived from a gene of a non-mammalian cell or a promoter whose enhancer portion has been removed.
(3) The expression vector of (1) or (2) above, wherein the UCOE comprises the nucleotide sequence as shown in SEQ ID NO: 1.
(4) A method of preparing a transformant that produces a foreign gene-derived protein, which comprises integrating a foreign gene into the expression vector of any one of (1) to (3) above, and transforming a dihydrofolate reductase gene-deficient host cell with the expression vector.
(5) A method of producing a foreign gene-derived protein, which comprises the following (a) to (d):
(a) integrating a foreign gene into the expression vector of any one of (1) to (3) above;
(b) transforming a dihydrofolate reductase gene-deficient host cell with the expression vector;
(c) culturing the resultant transformant in a hypoxanthine-thymidine-free medium; and
(d) collecting the foreign gene-derived protein from the cultured transformant.
(6) The method of (5) above, wherein a chemically defined medium (CD medium) or a CD medium supplemented with non-animal-based additives is used for culturing in (c).
(7) A method of screening for a transformant that produces a foreign gene-derived protein, which comprises the following (a), (b) and (c):
(a) integrating a foreign gene into the expression vector of any one of (1) to (3) above;
(b) transforming a dihydrofolate reductase gene-deficient host cell with the expression vector; and
(c) culturing the resultant transformant in a hypoxanthine-thymidine-free medium.
(8) A foreign gene expression vector which has a foreign gene integrated into the expression vector of any one of (1) to (3) above.
(9) A host cell which has been transformed with the foreign gene expression vector of (8) above.

The present specification encompasses the contents disclosed in the specifications and/or drawings of Japanese Patent Applications No. 2018-99704 and No. 2018-168591 based on which the present patent application claims priority.

BEST MODES FOR CARRYING OUT THE INVENTION

Figure 1:
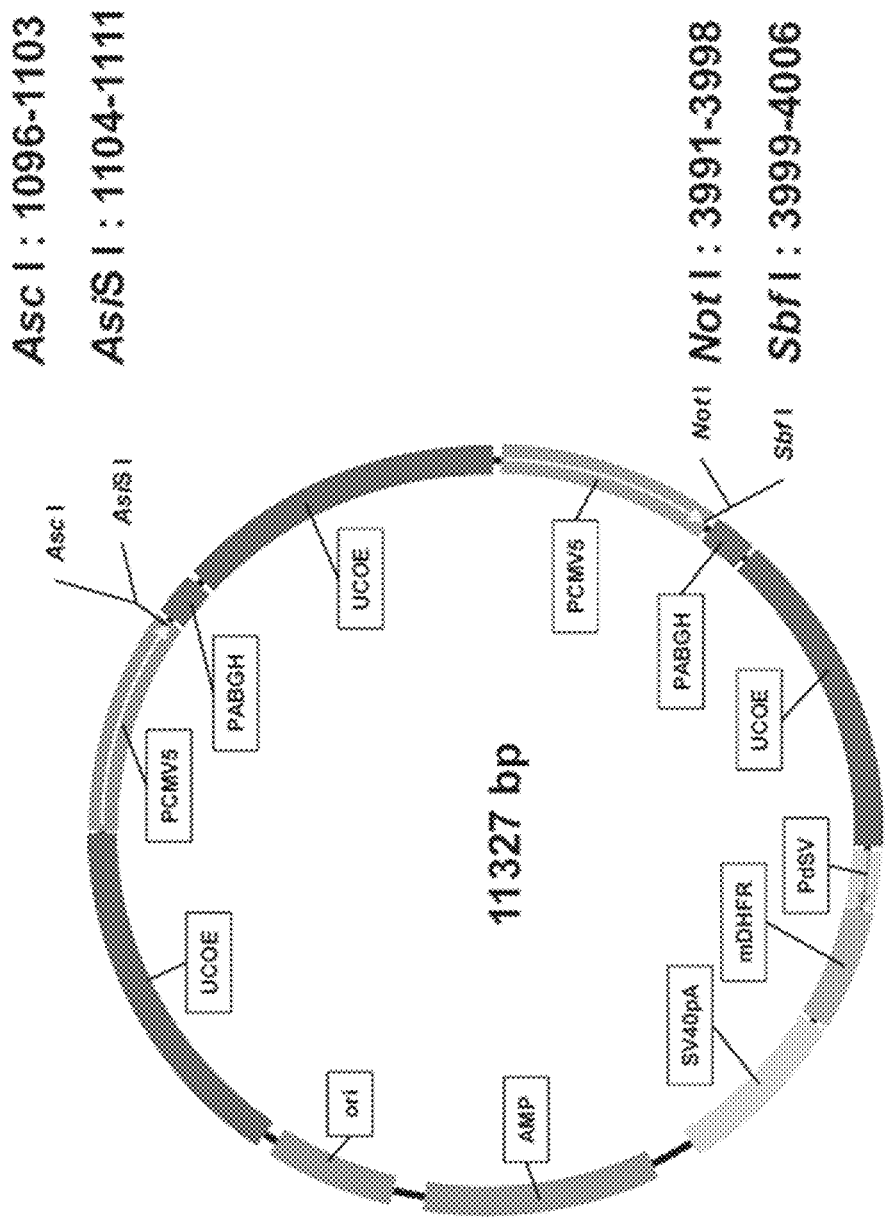
FIG. 1 This figure shows pDC62c5-U533 construct. PCMV5, or CMV5 promoter which is a fusion promoter of human cytomegalovirus promoter and adenovirus promoter (Nucleic Acid Research, 30, p. 2, 2002); PABGH, or a bovine growth hormone gene polyadenylation signal; UCOE, or a ubiquitously acting chromatin opening element; PdSV, or an enhancer-deleted simian virus 40 promoter; mDHFR, or a translation-impaired dihydrofolate reductase gene; SV40 pA, or a simian virus 40 polyadenylation signal; AMP, or a selection marker in E. coli (β-lactamase gene); ori, or a pUC plasmid-derived origin of replication. AscI, AsiSI, NotI and SbfI each represent a restriction enzyme cleavage site.

The present inventors altered the codons of the DHFR gene to those which would be least frequently used in mammals so as to extremely attenuate the expressabililty of DHFR, whereby even transformants were rendered difficult to survive under selection in HT-free media unless the plasmid gene to be incorporated was introduced into a position with extremely high expressability on the chromosome of dihydrofolate reductase gene-deficient host cells. Further, the present inventors introduced a ubiquitously acting chromatin opening element (UCOE) into the plasmid gene, whereby the production level of a protein of interest in the resultant transformant was increased while at the same time, the stability of its expression was enhanced.

Specifically, the present invention provides expression vectors for inducing high-level production of genetically recombined proteins in mammalian host cells.

The expression vector of the present invention is constructed by comprising the following (a), (b) and (c) on a backbone vector:

(a) a translation-impaired dihydrofolate reductase gene cassette whose expression is weakened by altering codons to those which are least frequently used in mammals (a translation-impaired DHFR gene cassette);

(b) a gene cassette comprising a cloning site for integration of a foreign gene that is located between a promoter and a polyadenylation signal; and (c) a ubiquitously acting chromatin opening element (UCOE).

In the present invention, a promoter as a component of a DHFR gene cassette (cistron) in which the codons of the DHFR gene have been altered to those which are least frequently used in mammals to lower the ability to induce the expression of DHFR is used so that the mechanism of DHFR expression in the host cell transformed through gene transfer is considerably impaired. As used herein, the term "gene cassette" refers to a unit for expressing a protein through transcription/translation that comprises a promoter, a structural gene, and a polyadenylation signal (polyA) as the basic components, and DNA sequences that are either associated with any of these components or of any other types may also be included as insertion sequences. The DHFR gene cassettes of the present invention are defined as "translation-impaired DHFR gene cassette" because unlike those in which the promoter is simply attenuated, they allow for specific acquisition of strains that can grow in HT-free media and which have the plasmid gene introduced into a transcriptional hot spot.

In the present invention, "the codons which are least frequently used in mammals" refers to preferably, for example, the codons which are least frequently used in humans. The codons which are least frequently used in humans include the codons disclosed in Kim et al. (Gene, 199, p. 293, 1997). Specific examples of such codons are GCA for alanine, CGA for arginine, AAU for asparagine, GAU for aspartic acid, UGU for cysteine, CAA for glutamine, GAA for glutamic acid, GGU for glycine, CAU for histidine, UUA for leucine, AAA for lysine, CCA for proline, UUU for phenylalanine, UCA for serine, ACU for threonine, UAU for tyrosine, and/or GUA for valine, to which the codon candidates are by no means limited.

In the present invention, "expression is weakened" if gene expression has been weakened at the transcription and/or translation stage, and specifically, this can be achieved by altering the codons to the above-described "codons which are least frequently used in mammals".

In the above-described "translation-impaired DHFR gene cassette", the region with altered codons is not particularly limited. Preferably, codons in a region corresponding to 30% or more (for example, 40% or more, 50% or more, 60% or more, 70% or more, 80% or more, 90% or more, 95% or more, or 100%) of the full length of the gene cassette are altered. The range of the codon-altered region may be determined arbitrarily by considering other conditions of the vector.

As the promoter in the above-described "translation-impaired DHFR gene cassette", those which are derived from the promoter of a protein gene that is usually difficult to be expressed in mammalian cells (e.g., promoter derived from a gene of non-mammalian cells) or a normal promoter from which the enhancer has been deleted may be used. More specifically, the SV40 virus antigen promoter from which the enhancer region has been removed (Mol. Cell Biol., 6, p. 2593, 1986) or promoters that are comparably very low in the ability to express are preferably used.

Integration of plasmid DNA into a transcriptional hot spot on the dihydrofolate reductase gene-deficient host cell chromosome can be eventually accomplished by selection in HT-free media according to the properties of the DHFR gene cassette, but expression per se of the foreign gene-derived protein at the transcriptional hot spot on the chromosome need be strongly induced. To this end, the promoter and polyadenylation signal (hereinafter, called polyA) in the cloning site (hereinafter, referred to as CS) where the protein gene is to be integrated may be selected from those having the strongest ability to induce expression. Examples of the promoters include, but are not limited to, human cytomegalovirus immediate early (hCMV MIE: Cell, 41, p. 521, 1985) promoter, CMV5 promoter which is a fusion promoter of human cytomegalovirus promoter and adenovirus promoter (Nucleic Acid Research, 30, p. 2, 2002), and β-actin promoter (Proc. Natl. Acad. Sci. USA, 84, p. 4831, 1987); and examples of polyA include, but are not limited to, bovine growth hormone-derived polyA sequence (DNA, 5, p. 115, 1986). The cloning site is composed of restriction enzyme cleavage sites. Examples of restriction enzyme cleavage site include, but are not limited to, Asc I, AsiS I, Acc65I, BamHI, BclI, BsaI, BsiWI, BstBI, BstEI, Bsu36I, DraIII, EagI, FseI, KpnI, MboI, Nhe I, Not I, PacI, RsrII, SalI, Sbf I, SexAI, SgfI and XcmI. Herein, a DNA fragment carrying this cloning site for integrating the protein gene of interest is called a "gene expression cassette".

UCOE is a DNA element present in close proximity to ubiquitously highly expressed genes; UCOE has such an ability that by creating an open chromatin environment, the likelihood that a gene introduced in the vicinity is transcribed into messenger RNA is maximized to eventually maximize the amount in which the protein encoded by the introduced gene is expressed. Furthermore, UCOE has anti-silencing activity based on its ability to inhibit methylation of the DNA in promoter region, so that it inhibits lowered transcriptional activity of the introduced gene due to long term subculture, which eventually inhibits a decrease in the amount of expression of the protein encoded by the introduced gene. Consequently, one may expect that by introducing UCOE into the expression vector of the present invention, the production level of a protein of interest in the resultant transformant will be increased while at the same time, the stability of its expression will be enhanced.

The nucleotide sequence of UCOE introduced into the expression vector in an Example described later is shown in SEQ ID NO: 1. The nucleotide sequence shown in SEQ ID NO: 1 may have mutations, e.g. substitution, deletion or insertion of nucleotides, introduced thereinto as long as the object of the present invention is achieved. The number of UCOEs to be introduced into the expression vector may be one or more. UCOEs may be suitably introduced in such positions that the gene cassette to be expressed is sandwiched therebetween.

The expression vector of the present invention may carry a selection marker which is either a drug resistance gene (e.g., ampicillin resistance gene, kanamycin resistance gene, chloramphenicol resistance gene, etc.) or an origin of replication (e.g., pUC-derived origin of replication, ColE1-derived origin of replication, p15A-derived origin of replication, pSC101-derived origin of replication, etc.).

The expression vectors of the present invention are exemplified by the expression vector specifically described in Examples (pDC62c5-U533), to which they are by no means limited.

Furthermore, the present invention provides a method for producing transformants that produce foreign gene-derived proteins, which comprises integrating a foreign gene into the above-described expression vector and transforming dihydrofolate reductase gene-deficient host cells using the expression vector. The transformants may have an ability to produce foreign gene-derived proteins at high levels and an ability to grow in HT-free media.

To describe a specific method that may be employed, a foreign gene encoding a protein to be expressed is integrated into the cloning site (hereinafter, referred to as CS) of an expression vector of the present invention; then, dihydrofolate reductase gene-deficient host cells are transformed with the expression vector by making use of a transfection method (examples of the transfection method referred to herein include methods well known to those skilled in the art such as lipofectin method, electroporation, calcium phosphate method, and microinjection); and then transformants are selected by resistance in HT-free media to thereby obtain those transformants which have high productivity for the protein of interest. For example, when pDC62c5-U533 is used, a foreign gene cDNA may be inserted between Asc I and Sfb I. When the foreign gene is an antibody gene, antibody light chain cDNA may be inserted between Asc I and AsiS I, and antibody heavy chain cDNA between Not I and Sbf I, of pDC62c5-U533. In pDC62c5-U533, Asc I and AsiS I, as well as Not I and Sbf I provide cloning sites. Consider, for example, the case of pDC62c5-U533 that has only one site for insertion of a foreign gene; a foreign gene cDNA may be inserted between Asc I and AsiS I. In pDC62c5-U533 which has only one site for insertion of a foreign gene, Asc I and AsiS I provide a cloning site. Kozak is preferably added to a foreign gene before it is integrated into the expression vector of the present invention. Kozak is preferably optimized, with the sequence of the optimized Kozak being shown in SEQ ID NO: 2. Kozak may be suitably added upstream of the initiation codon of the foreign gene cDNA.

The present invention also provides a foreign gene expression vector which has a foreign gene integrated into the expression vector of the present invention.

In the present invention, host cells are not particularly limited as long as they are cells suitable for expressing foreign gene-derived proteins. Preferably, dihydrofolate reductase gene-deficient mammalian cells, and more preferably, dihydrofolate reductase gene-deficient Chinese hamster ovary cells (CHO cells) may be enumerated.

Many of the transformed cells surviving the selection in an HT-free medium have already achieved a relatively high level of protein expression, but to select from these cells such transformants that have an even higher level of production ability, the level of protein expression may be measured.

The present invention also provides a host cell transformed with the foreign gene expression vector of the present invention.

Furthermore, the present invention provides a method for producing a foreign gene-derived protein, which comprises the following (a) to (d):
(a) integrating a foreign gene into an expression vector of the present invention;
(b) transforming a dihydrofolate reductase gene-deficient host cell with the expression vector;
(c) culturing the resultant transformant in an HT-free medium; and
(d) collecting the foreign gene-derived protein from the cultured transformant.

In (c) above of the present invention, transformants (colonies) showing highly efficient protein expression can be selected by culturing in an HT-free medium. The selected transformants may be continuously cultured in the same medium, or they may be cultured after being transferred to another medium such as a medium for large-scale expression.

In the present invention, media for culturing or adapting transformants are not particularly limited, but they are preferably exemplified by a serum-free medium, more preferably a CD medium which may optionally be supplemented with non-animal-based additives (e.g., salts, amino acids, saccharides, vitamins, recombinant insulin, recombinant transferrin, etc.)

When collecting foreign gene-derived proteins from transformants that have been cultured in the present invention, the proteins may be purified by methods known to those skilled in the art (filtration, centrifugation, column purification, and so forth). It is also possible to express the foreign gene-derived proteins as fusion proteins with other proteins for such purposes as facilitating purification.

Furthermore, the present invention provides a method of screening for transformants that produce a foreign gene-derived protein, which comprises the following (a) to (c):
(a) integrating a foreign gene into an expression vector of the present invention;
(b) transforming a dihydrofolate reductase gene-deficient host cell with the expression vector; and
(c) culturing the resultant transformant in an HT-free medium.

All prior art documents cited herein are incorporated herein by reference.

EXAMPLE

Hereinbelow, Examples of the present invention will be described.

[Example 1] Preparation of pDC62c5-U533

A backbone vector pDC6 (Japanese Patent No. 5704753) was modified to construct pDC62c5-U533, a vector of the present invention. The entire nucleotide sequence of the backbone vector pDC62c5-U533 is shown in SEQ ID NO: 3. The vector pDC62c5-U533 carries a translation-impaired DHFR gene introduced in the region of 6067-6630, with the DHFR nucleotide sequence being such that codons in the range of 180 nucleotides from the 5' end have been altered to those which are least frequently used in mammals (FIG. 1). Further, a UCOE has been introduced in the regions of 1339-2889, 4234-5784 and 9771-11321. The nucleotide sequence of UCOE is shown in SEQ ID NO: 1.

[Example 2] Preparation of pDC62c5-U533-OMLH

Figure 2:
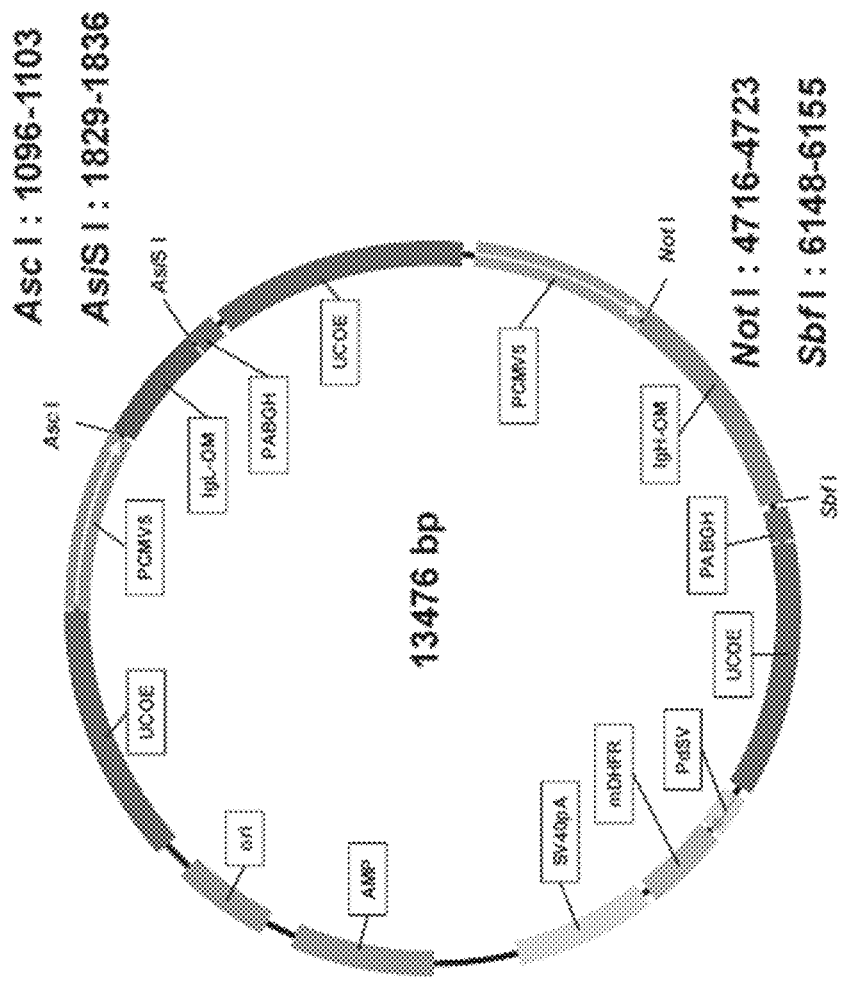
FIG. 2 This figure shows pDC62c5-U533-OMLH construct. PCMV5, or CMV5 promoter which is a fusion promoter of human cytomegalovirus promoter and adenovirus promoter (Nucleic Acid Research, 30, p. 2, 2002); IgL-OM, or Omalizumab light chain cDNA; PABGH, or a bovine growth hormone gene polyadenylation signal; UCOE, or a ubiquitously acting chromatin opening element; IgH-OM, or Omalizumab heavy chain cDNA; PdSV, or an enhancer-deleted simian virus 40 promoter; mDHFR, or a translation-impaired dihydrofolate reductase gene; SV40 pA, or a simian virus 40 polyadenylation signal; AMP, or a selection marker in *E. coli* (β-lactamase gene); ori, or a pUC plasmid-derived origin of replication. AscI, AsiSI, NotI and SbfI each represent a restriction enzyme cleavage site.

The nucleotide sequences No. 1098 to No. 1108 of pDC62c5-U533 were substituted with a cDNA encoding the light chain of a human omalizumab (OMLH) (having an optimized Kozak added upstream of the initiation codon) as shown in SEQ ID NO: 4, and, further, the nucleotide sequences No. 3993 to No. 4004 of pDC62c5-U533 were substituted with a cDNA encoding the heavy chain of the human omalizumab (OMLH) (having an optimized Kozak added upstream of the initiation codon) as shown in SEQ ID NO: 5, whereby pDC62c5-U533-OMLH (FIG. 2) was constructed. The sequence of the optimized Kozak is shown in SEQ ID NO: 2.

Prior to gene transfer, the vector was linearized with a restriction enzyme ClaI.

[Example 3] Transfection of pDC62c5-U533-OMLH into CHO Cells, Selection, Productivity Test and Expression Stability Test 18 µg of pDC62c5-U533-OMLH was transfected into 15,000,000 CHO cells (CHO DG44 cells) in 125 ml culture flasks (Erlenmeyer Flask, Baffled, 125 ml, Vent Cap, cat #431405, Corning) using the Lipofectin method (with Free-Style MAX Reagent, Life Technologies).

The method of transfection was in accordance with the manufacturer's instructions for use. Following 48 hours after transfection, the number of cells was counted, and then the cells were diluted with CD OptiCHO medium (Life Technologies) supplemented with 4 mM GlutaMAX-I (Life Technologies). In a 96-well microtiter plate, mixing with 12,000 cells/well of non-transfected cells was conducted at a concentration of 4,000 transfected cells/well. The mixed cells were then seeded in 10 plates (960 wells) and cultured in the presence of 8% carbon dioxide gas at 37° C. for approximately three weeks. From the viable cells, 35 HT-free medium resistant clones were randomly selected. In a fresh 96-well microtiter plate, mixing with 12,000 cells/well of non-transfected cells was conducted at a concentration of 16,000 transfected cells/well. The mixed cells were then seeded in 10 plates (960 wells) and cultured in the presence of 8% carbon dioxide gas at 37° C. for approximately three weeks. From the viable cells, 71 HT-free medium resistant clones were randomly selected to thereby obtain a total of 106 clones. The thus obtained HT-free medium resistant clones were transferred to a 24-well plate together with CD OptiCHO medium (Life Technologies) supplemented with 4 mM GlutaMAX-I (Life Technologies), and cultured until cells occupied ⅓ or more of the base area of each well. The cells grown in the 24-well plate were transferred to a 6-well plate together with CD OptiCHO medium (Life Technologies) supplemented with 4 mM GlutaMAX-I (Life Technologies), and cultured until cells occupied ⅓ or more of the base area of each well.

Figure 6:
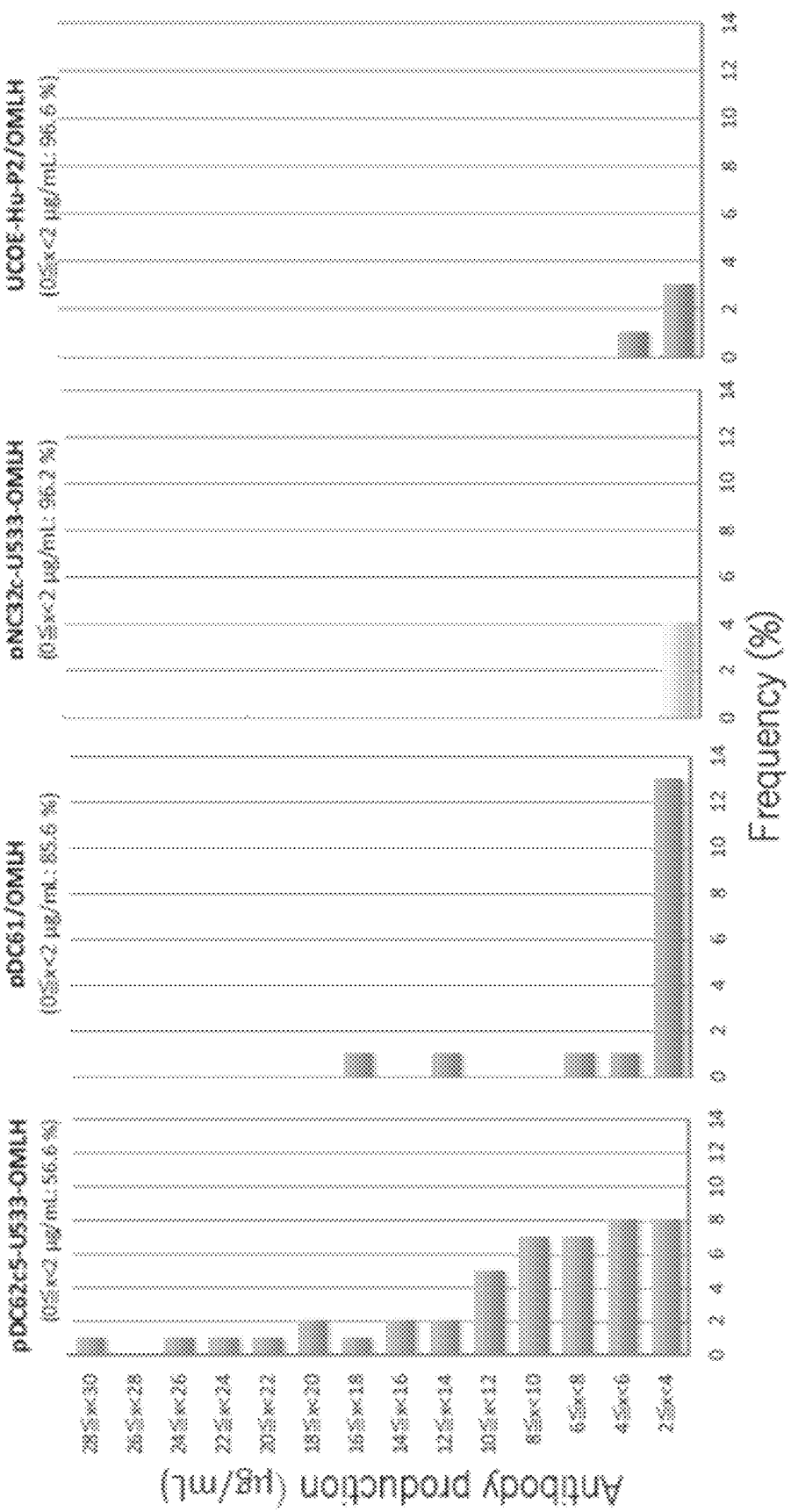
FIG. 6 This figure shows distribution of the expression level of an antibody produced by CHO cells transfected with pDC62c5-U533-OMLH (expression vector of the present invention), pDC61-OMLH (conventional vector), pNC32c-U533-OMLH (control vector) or pUCOE-Hu-P2/OMLH (vector manufactured by Millipore) (data obtained by 3-day culture).

Each clone (1 ml) was placed in a sterile tube and centrifuged at 300×g for 7 min. The supernatant was discarded, and the cells were suspended in 0.55 ml of a fresh medium (CD OptiCHO medium (Life Technologies) supplemented with 4 mM GlutaMAX-I (Life Technologies)), and cell counting was done. After the cells were diluted with a medium to give a viable cell density of $2\times10^5$ cells/ml, 0.4 ml of the dilution was transferred to a fresh 24-well plate and subjected to rotary shaking culture (125 rpm) in the presence of 8% carbon dioxide gas at 37° C. for 72 hrs. After culture, cell counting was done, followed by centrifugation at 9300×g for 2 min and collection of the supernatant. Subsequently, IgG concentration in the culture supernatant was measured by ELISA. As a result, the IgG yield from the clone of maximum productivity was 28.5 μg/ml/3 days, with 16 out of the 106 clones (15.1%) producing 10 μg/ml or more of IgG (FIG. 6).

Figure 7:
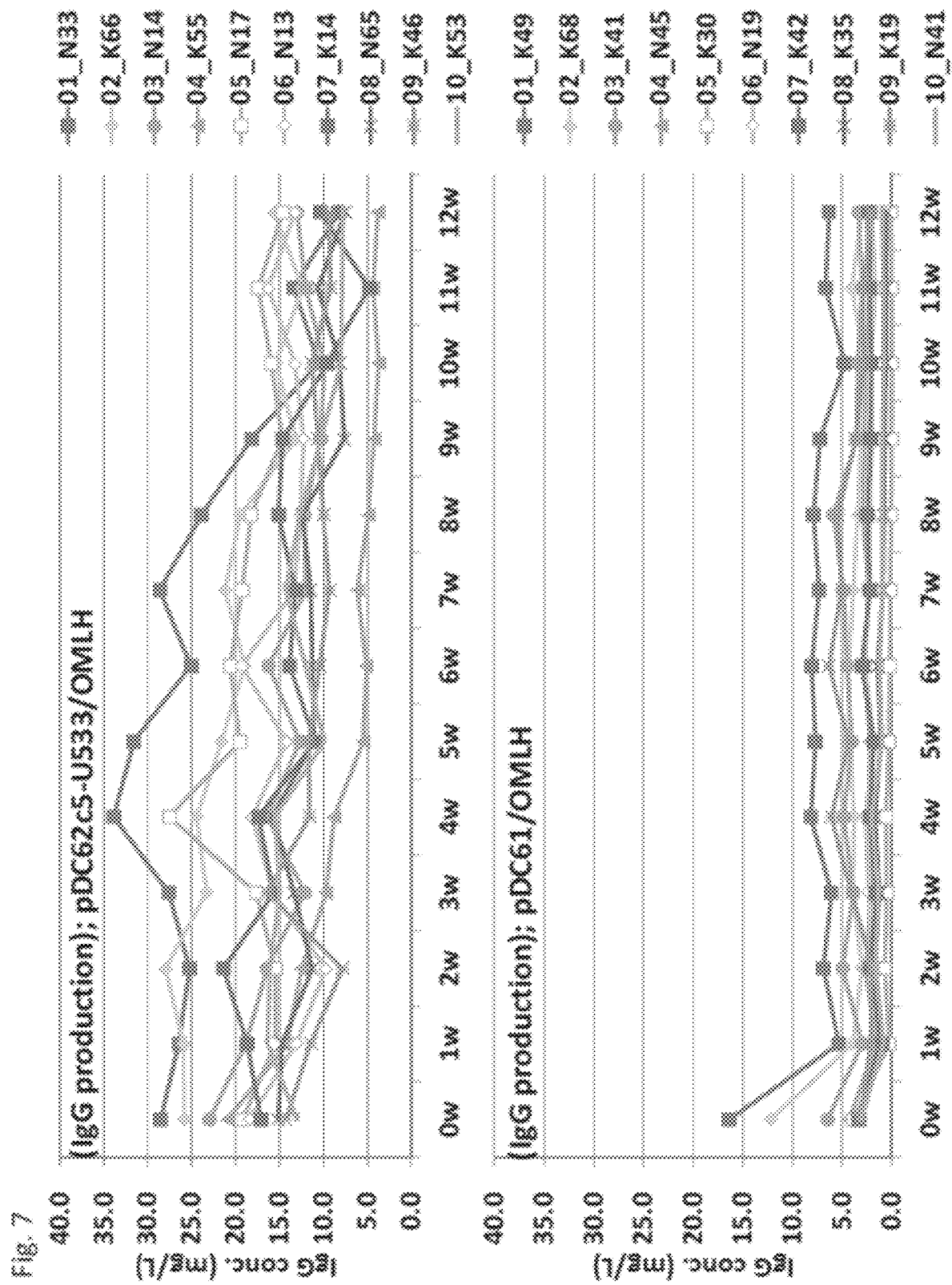
FIG. 7 This figure shows changes in the level of an antibody produced by CHO cells transfected with pDC62c5-U533-OMLH (expression vector of the present invention) or pDC61-OMLH (conventional vector) (over 1 to 12 weeks from the start of culture).

Next, top 10 clones in terms of IgG yield were selected and subjected to an expression stability test. In the expression stability test, subculture was started from a frozen stock of each clone. In subculture, cells were diluted to give a density of $2\times10^5$ cells/ml and subjected to rotary shaking culture for 3 to 4 days. The resultant cells were diluted again to give a density of $2\times10^5$ cells/ml. These operations were carried out repeatedly. At days 0, 7, 14, 21, 28, 35, 42, 49, 56, 63, 72, 79 and 86 from the start of rotary shaking culture, cells were diluted to give a density of $2\times10^5$ cells/ml and 0.4 ml of the dilution was subjected to rotary shaking culture (125 rpm) on a 24-well plate for 72 hrs. The supernatant was collected and measured for IgG yield by ELISA. IgG yields from the 10 clones were 28.5-13.0 mg/L at week 0 and 15.6-3.8 mg/L at week 12. As regards the expression stability of pDC62c5-U533-OMLH-transfected cells, 7 out of the 10 clones retained 70% or more of IgG production capacity until week 8 as relative to the value before preparation of the frozen stock; 2 clones retained 50% to less than 70% of IgG production capacity; and 1 clone retained less than 50% of IgG production capacity. At week 12, 2 clones retained 70% or more of IgG production capacity; 5 clones retained 50% to less than 70% of IgG production capacity; and 3 clones retained less than 50% of IgG production capacity (FIG. 7).

[Example 4] Preparation of pDC61

The nucleotide sequences No. 3182 to No. 5843 of pDC6 (Japanese Patent No. 5704753) were substituted with the sequence shown in SEQ ID NO: 7 to thereby construct pDC61. The entire nucleotide sequence of the backbone vector pDC61 is shown in SEQ ID NO: 6.

[Example 5] Preparation of pDC61/OMLH

Figure 3:
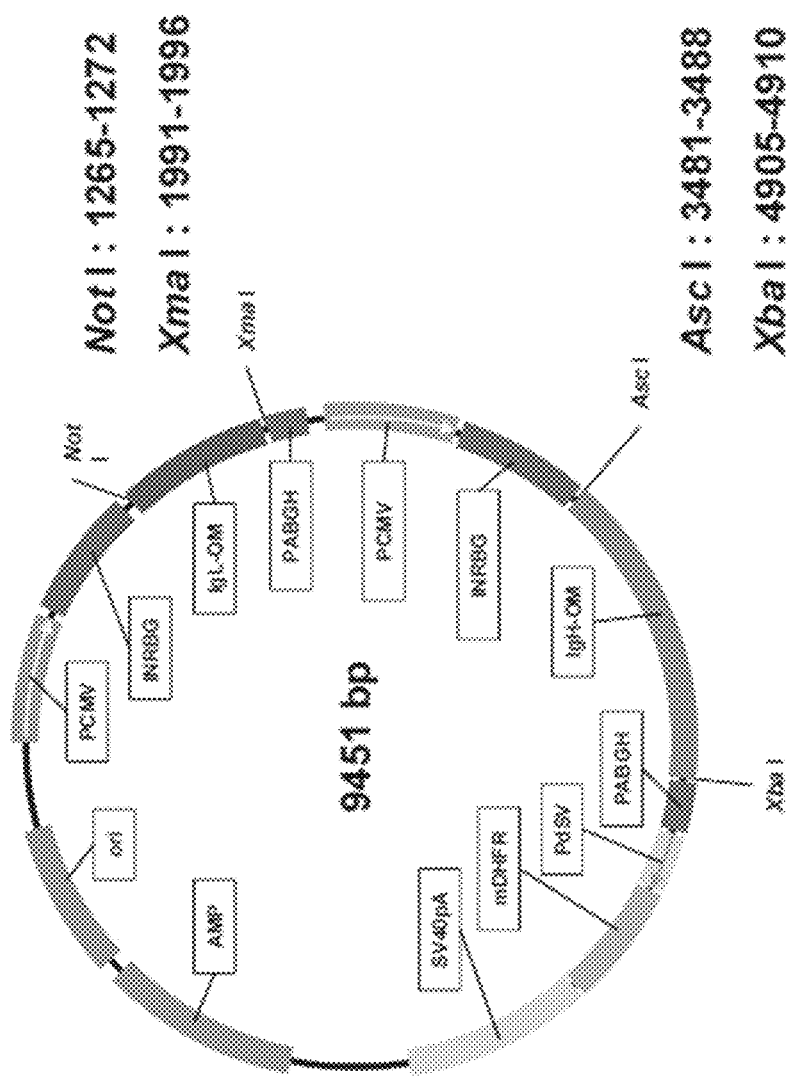
FIG. 3 This figure shows pDC61-OMLH construct. PCMV, or a human cytomegalovirus promoter (Nucleic Acid Research, 30, p. 2, 2002); INRBG, or a rabbit β-globin gene intron sequence; IgL-OM, or Omalizumab light chain cDNA; PABGH, or a bovine growth hormone gene polyadenylation signal; IgH-OM, or Omalizumab heavy chain cDNA; PdSV, or an enhancer-deleted simian virus 40 promoter; mDHFR, or a translation-impaired dihydrofolate reductase gene; SV40 pA, or a simian virus 40 polyadenylation signal; AMP, or a selection marker in *E. coli* (β-lactamase gene); ori, or a pUC plasmid-derived origin of replication. AscI, AsiSI, NotI and SbfI each represent a restriction enzyme cleavage site.

The nucleotide sequences No. 1267 to No. 1273 of pDC61 were substituted with a cDNA encoding the light chain of a human omalizumab (OMLH) as shown in SEQ ID NO: 8 and the nucleotide sequences No. 2765 to No. 2771 of pDC61 were substituted with a cDNA encoding the heavy chain of the human omalizumab (OMLH) as shown in SEQ ID NO: 9, whereby pDC61/OMLH (FIG. 3) was constructed.

Prior to gene transfer, the vector was linearized with a restriction enzyme ClaI.

[Example 6] Transfection of pDC61/OMLH into CHO Cells, Selection, Productivity Test and Expression Stability Test 18 μg of pDC61/OMLH was transfected into 15,000,000 CHO cells (CHO DG44 cells) in 125 ml culture flasks (Erlenmeyer Flask, Baffled, 125 ml, Vent Cap, cat #431405, Corning) using the Lipofectin method (with FreeStyle MAX Reagent, Life Technologies). The method of transfection was in accordance with the manufacturer's instructions for use. Following 48 hours after transfection, the number of cells was counted, and then the cells were diluted with CD OptiCHO medium (Life Technologies) supplemented with 4 mM GlutaMAX-I (Life Technologies). In a 96-well microtiter plate, mixing with 12,000 cells/well of non-transfected cells was conducted at a concentration of 40,000 transfected cells/well. The mixed cells were then seeded in 10 plates (960 wells) and cultured in the presence of 8% carbon dioxide gas at 37° C. for approximately three weeks. From the viable cells, 118 HT-free medium resistant clones were randomly selected. The thus obtained HT-free medium resistant clones were transferred to a 24-well plate together with CD OptiCHO medium (Life Technologies) supplemented with 4 mM GlutaMAX-I (Life Technologies), and cultured until cells occupied ⅓ or more of the base area of each well. The cells grown in the 24-well plate were transferred to a 6-well plate together with CD OptiCHO medium (Life Technologies) supplemented with 4 mM GlutaMAX-I (Life Technologies), and cultured until cells occupied ⅓ or more of the base area of each well. Each clone (1 ml) was placed in a sterile tube and centrifuged at 300 ×g for 7 min. The supernatant was discarded, and the cells were suspended in 0.55 ml of a fresh medium (CD OptiCHO medium (Life Technologies) supplemented with 4 mM GlutaMAX-I (Life Technologies)), and cell counting was done. After the cells were diluted with a medium to give a viable cell density of $2\times10^5$ cells/ml, 0.4 ml of the dilution was transferred to a fresh 24-well plate and subjected to rotary shaking culture (125 rpm) in the presence of 8% carbon dioxide gas at 37° C. for 72 hrs. After culture, cell counting was done, followed by centrifugation at 9300×g for 2 min and collection of the supernatant. Subsequently, IgG concentration in the culture supernatant was measured by ELISA. As a result, the IgG yield from the clone of maximum productivity was 16.4 µg/ml/3 days, with 2 out of the 118 clones (1.7%) producing 10 µg/ml or more of IgG (FIG. 6).

Next, top 10 clones in terms of IgG yield were selected and subjected to an expression stability test. In the expression stability test, subculture was started from a frozen stock of each clone. In subculture, cells were diluted to give a density of 2×10^5 cells/ml and subjected to rotary shaking culture for 3 to 4 days. The resultant cells were diluted to give a density of 2×10^5 cells/ml again. These operations were carried out repeatedly. At days 0, 7, 14, 21, 28, 35, 42, 49, 56, 63, 72, 79 and 86 from the start of rotary shaking culture, cells were diluted to give a density of 2×10^5 cells/ml and 0.4 ml of the dilution was subjected to rotary shaking culture (125 rpm) on a 24-well plate for 72 hrs. The supernatant was collected and measured for IgG yield by ELISA. The IgG yields of the 10 clones were 16.4-3.1 mg/L at week 0 and 6.3-0.1 mg/L at week 12. As regards the expression stability of pDC61/OMLH-transfected cells, 3 out of the 10 clones retained 70% or more of IgG production capacity until week 8 as relative to the value before preparation of the frozen stock; 2 clones retained 50% to less than 70% of IgG production capacity; and 5 clones retained less than 50% of IgG production capacity. At week 12, no clones retained 70% or more of IgG production capacity; 5 clones retained 50% to less than 70% of IgG production capacity; and 5 clones retained less than 50% of IgG production capacity.

[Example 7] Preparation of pNC32c-U533

The backbone vector pDC61 (prepared in Example 4) was modified to construct pNC32c-U533, a vector of the present invention. The entire nucleotide sequence of the backbone vector pNC32c-U533 is shown in SEQ ID NO: 10. The vector pNC32c-U533 has a neomycin phosphotransferase gene introduced in the region of nucleotide sequences No. 5196 to No. 5990. It also has a UCOE introduced in the region of nucleotide sequences No. 867 to No. 2417, the region of No. 3291 to No. 4841 and the region of No. 9130 to No. 10680. The nucleotide sequence of UCOE is shown in SEQ ID NO: 1.

[Example 8] Preparation of pNC32c-U533-OMLH

Figure 4:
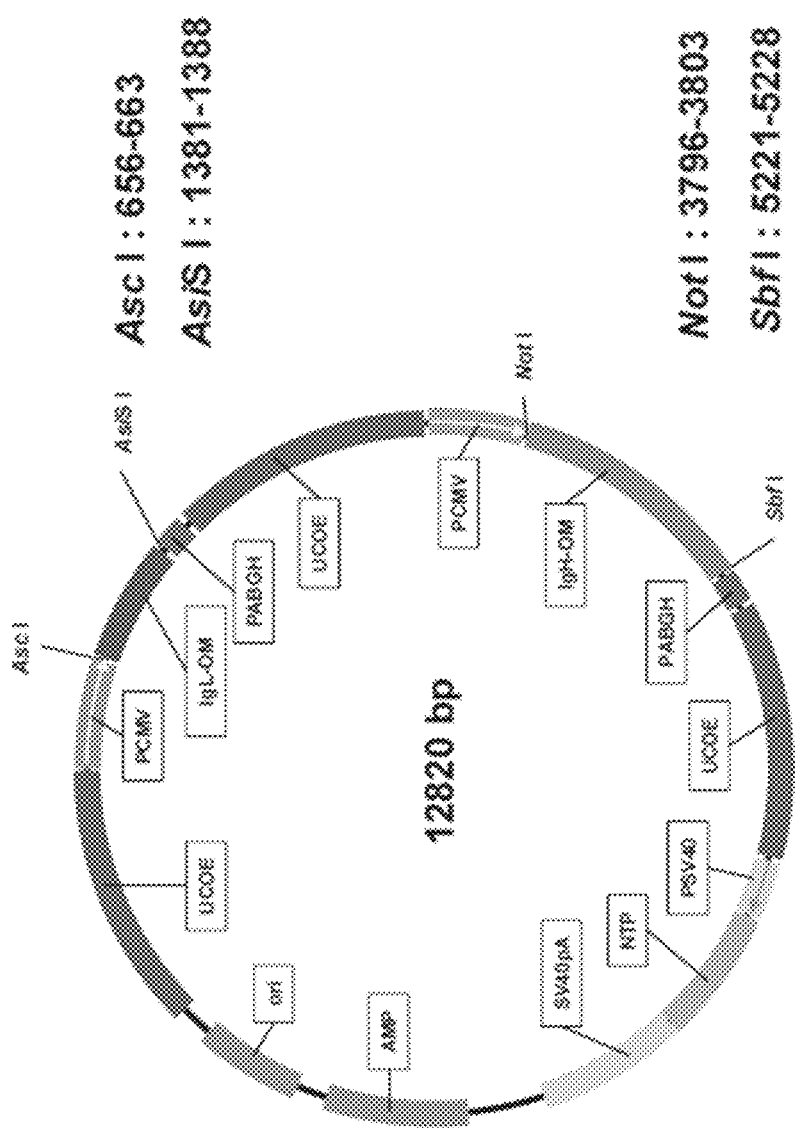
FIG. 4 This figure shows pNC32c-U533-OMLH construct. PCMV, or a human cytomegalovirus promoter (Nucleic Acid Research, 30, p. 2, 2002); IgL-OM, or Omalizumab light chain cDNA; SV40 pA, or a simian virus 40 polyadenylation signal; UCOE, or a ubiquitously acting chromatin opening element; IgH-OM, or Omalizumab heavy chain cDNA; PSV40, or a simian virus 40 promoter; NTP, or a neomycin phosphotransferase gene; SV40 pA, or a simian virus 40 polyadenylation signal; AMP, or a selection marker in *E. coli* (β-lactamase gene); ori, or a pUC plasmid-derived origin of replication. AscI, AsiSI, NotI and SbfI each represent a restriction enzyme cleavage site.

The nucleotide sequences No. 658 to No. 668 of pNC32c-U533 were substituted with a cDNA encoding the light chain of a human omalizumab (OMLH) as shown in SEQ ID NO: 11 and the nucleotide sequences No. 3081 to No. 3092 of pNC32c-U533 were substituted with a cDNA encoding the heavy chain of the human omalizumab (OMLH) as shown in SEQ ID NO: 12, whereby pNC32c-U533-OMLH (FIG. 4) was constructed.

Prior to gene transfer, the vector was linearized with a restriction enzyme ClaI.

[Example 9] Transfection of pNC32c-U533-OMLH into CHO Cells, Selection and Productivity Test 18 µg of pNC32c-U533-OMLH was transfected into 15,000,000 CHO cells (CHO DG44 cells) in 125 ml culture flasks (Erlenmeyer Flask, Baffled, 125 ml, Vent Cap, cat #431405, Corning) using the Lipofectin method (with Free-Style MAX Reagent, Life Technologies). The method of transfection was in accordance with the manufacturer's instructions for use. Following 48 hours after transfection, the number of cells was counted, and then the cells were diluted with CD OptiCHO medium (Life Technologies) supplemented with 4 mM GlutaMAX-I (Life Technologies), 400 µg/ml G418 sulfate (Wako) and 1×HT Supplement (Life Technologies). In a 96-well microtiter plate, mixing with 12,000 cells/well of non-transfected cells was conducted at a concentration of 800 transfected cells/well. The mixed cells were then seeded in 10 plates (960 wells) and cultured in the presence of 8% carbon dioxide gas at 37° C. for approximately three weeks. From the viable cells, 108 clones with G418 resistance were randomly selected. The thus obtained G418 resistant clones were transferred to a 24-well plate together with CD OptiCHO medium (Life Technologies) supplemented with 4 mM GlutaMAX-I (Life Technologies), 400 µg/ml G418 sulfate (Wako) and 1×HT Supplement (Life Technologies), and cultured until cells occupied ⅓ or more of the base area of each well. The cells grown in the 24-well plate were transferred to a 6-well plate together with CD OptiCHO medium (Life Technologies) supplemented with 4 mM GlutaMAX-I (Life Technologies), 400 µg/ml G418 sulfate (Wako) and 1×HT Supplement (Life Technologies), and cultured until cells occupied ⅓ or more of the base area of each well. Each clone (1 ml) was placed in a sterile tube and centrifuged at 300×g for 7 min. The supernatant was discarded, and the cells were suspended in 0.55 ml of a fresh medium (CD OptiCHO medium (Life Technologies) supplemented with 4 mM GlutaMAX-I (Life Technologies), 400 µg/ml G418 sulfate (Wako) and 1×HT Supplement (Life Technologies)), and cell counting was done. After the cells were diluted with a medium to give a viable cell density of 2×10^5 cells/ml, 0.4 ml of the dilution was transferred to a fresh 24-well plate and subjected to rotary shaking culture (125 rpm) in the presence of 8% carbon dioxide gas at 37° C. for 72 hrs.

After culture, cell counting was done, followed by centrifugation at 9300×g for 2 min and collection of the supernatant. Subsequently, IgG concentration in the culture supernatant was measured by ELISA. As a result, the IgG yield from the clone of maximum productivity was 2.6 µg/ml/3 days, with 0 out of 105 clones producing 10 µg/ml or more of IgG.

[Example 10] Preparation of UCOE-Hu-P2/OMLH

The nucleotide sequences No. 5309 to No. 5311 of a commercially available vector UCOE® Expression Vector—Human 4 kb Puro Set (Merck, cat #5.04867.0001) were substituted with the sequence shown in SEQ ID NO: 13, whereby a recognition site for restriction enzyme BstBI was created (UCOE-Hu-P2).

Figure 5:
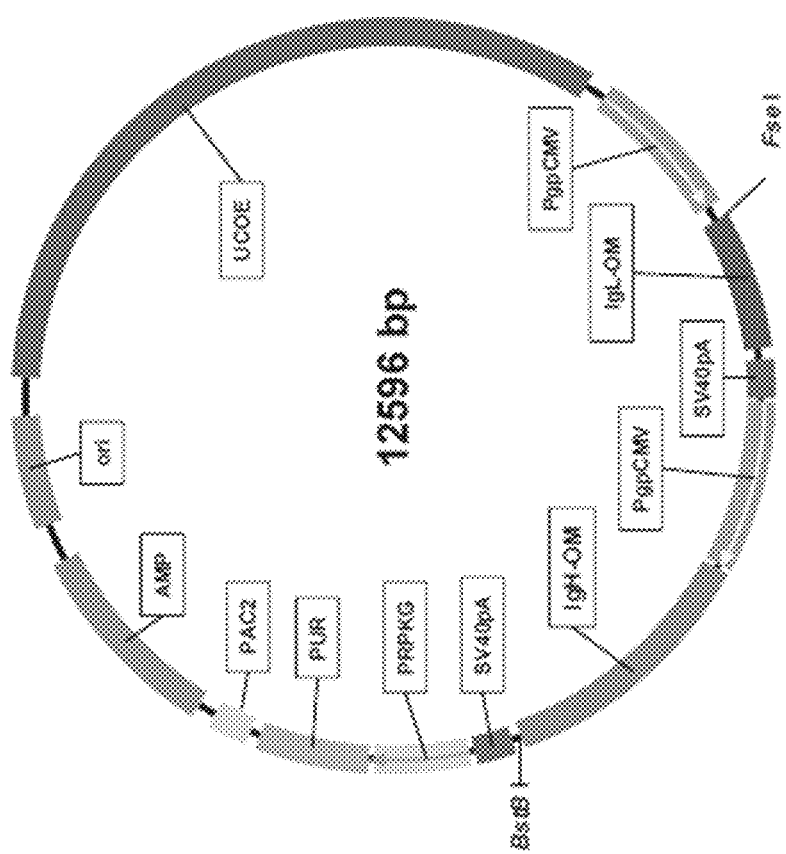
FIG. 5 This figure shows pUCOE-Hu-P2-OMLH construct. UCOE, or a ubiquitously acting chromatin opening element; PgpCMV, or a guinea pig cytomegalovirus promoter (Nucleic Acid Research, 30, p. 2, 2002); IgL-OM, or Omalizumab light chain cDNA; SV40 pA, or a simian virus 40 polyadenylation signal; IgH-OM, or Omalizumab heavy chain cDNA; PPGK, or a mouse phosphoglycerate kinase promoter; PUR, or a puromycin N-acetyltransferase gene; PAC2, or a complement factor 2 gene polyadenylation signal; AMP, or a selection marker in *E. coli* (β-lactamase gene); ori, or a pUC plasmid-derived origin of replication. AscI, AsiSI, NotI and SbfI each represent a restriction enzyme cleavage site.

Using FseI recognition site and BstBI recognition site on UCOE-Hu-P2, the sequence shown in SEQ ID NO: 14 comprising a cDNA encoding human omalizumab light chain (OML) as linked to a simian virus 40 polyadenylation signal (SV40 pA), a guinea pig cytomegalovirus promoter (PgpCMV) and a cDNA encoding human omalizumab heavy chain (OMR) was inserted into UCOE-Hu-P2 to thereby construct UCOE-Hu-P2/OMLH (FIG. 5).

Prior to gene transfer, the vector was linearized with restriction enzyme HindIII.

[Example 11] Transfection of UCOE-Hu-P2/OMLH into CHO Cells, Selection and Productivity Test 18 µg of UCOE-Hu-P2/OMLH was transfected into 15,000,000 CHO cells (CHO DG44 cells) in 125 ml culture flasks (Erlenmeyer Flask, Baffled, 125 ml, Vent Cap, cat #431405, Corning) using the Lipofectin method (with FreeStyle MAX Reagent, Life Technologies). The method of transfection was in accordance with the manufacturer's instructions for use. Following 48 hours after transfection, the number of cells was counted, and then the cells were diluted with CD OptiCHO medium (Life Technologies) supplemented with 4 mM GlutaMAX-I (Life Technologies), 100 µg/ml puromycin dihydrochloride (Thermo Fisher Scientific) and 1×HT Supplement (Life Technologies).

In a 96-well microtiter plate, mixing with 12,000 cells/well of non-transfected cells was conducted at a concentration of 4,000 transfected cells/well. The mixed cells were then seeded in 10 plates (960 wells) and cultured in the presence of 8% carbon dioxide gas at 37° C. for approximately three weeks. From the viable cells, 33 puromycin resistant clones were randomly selected. In a 96-well microtiter plate, mixing with 12,000 cells/well of non-transfected cells was conducted at a concentration of 16,000 transfected cells/well. The mixed cells were then seeded in 10 plates (960 wells) and cultured in the presence of 8% carbon dioxide gas at 37° C. for approximately three weeks. From the viable cells, 84 puromycin resistant clones were randomly selected to thereby obtain a total of 117 clones. The thus obtained puromycin resistant clones were transferred to a 24-well plate together with CD OptiCHO medium (Life Technologies) supplemented with 4 mM GlutaMAX-I (Life Technologies), 100 µg/ml puromycin dihydrochloride (Thermo Fisher Scientific) and 1×HT Supplement (Life Technologies), and cultured until cells occupied ⅓ or more of the base area of each well. The cells grown in the 24-well plate were transferred to a 6-well plate together with CD OptiCHO medium (Life Technologies) supplemented with 4 mM GlutaMAX-I (Life Technologies), 100 µg/ml puromycin dihydrochloride (Thermo Fisher Scientific) and 1×HT Supplement (Life Technologies), and cultured until cells occupied ⅓ or more of the base area of each well. Each clone (1 ml) was placed in a sterile tube and centrifuged at 300×g for 7 min. The supernatant was discarded, and the cells were suspended in 0.55 ml of a fresh medium (CD OptiCHO medium (Life Technologies) supplemented with 4 mM GlutaMAX-I (Life Technologies), 100 µg/ml puromycin dihydrochloride (Thermo Fisher Scientific) and 1×HT Supplement (Life Technologies)), and cell counting was done. After the cells were diluted with a medium to give a viable cell density of 2×10^5 cells/ml, 0.4 ml of the dilution was transferred to a fresh 24-well plate and subjected to rotary shaking culture (125 rpm) in the presence of 8% carbon dioxide gas at 37° C. for 72 hrs. After culture, cell counting was done, followed by centrifugation at 9300×g for 2 min and collection of the supernatant. Subsequently, IgG concentration in the culture supernatant was measured by ELISA. As a result, the IgG yield from the clone of maximum productivity was 4.7 µg/ml/3 days, with 0 out of the 117 clones producing 10 µg/ml or more of IgG.

[Example 12] Expression of Canine CTLA-4-Ig Using pDC62c5-U533

A vector pDC62c5-U533 having only one site for foreign gene insertion (between AscI and AsisSI) was prepared by a method well known to those skilled in the art. Briefly, the region of the nucleotide sequences No. 2896 to No. 5784 (nucleotide sequences encoding PCMV5, PABGH and UCOE) was deleted from the pDC62c5-U533 prepared in Example 1.

Figure 8:
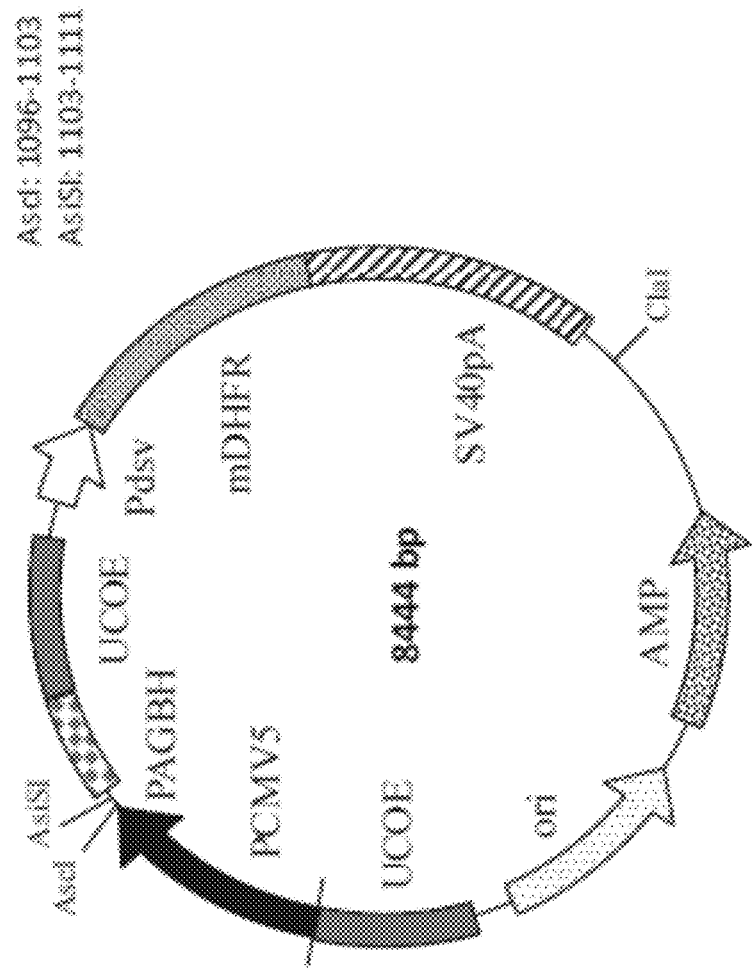
FIG. 8 This figure shows pDC62c5-U533 construct that has only one site for foreign gene insertion. PCMV5, or CMV5 promoter which is a fusion promoter of human cytomegalovirus promoter and adenovirus promoter (Nucleic Acid Research, 30, p. 2, 2002); PABGH, or a bovine growth hormone gene polyadenylation signal; UCOE, or a ubiquitously acting chromatin opening element; PdSV, or an enhancer-deleted simian virus 40 promoter; mDHFR, or a translation-impaired dihydrofolate reductase gene; SV40 pA, or a simian virus 40 polyadenylation signal; AMP, or a selection marker in *E. coli* (β-lactamase gene); ori, or a pUC plasmid-derived origin of replication. AscI, AsiSI and ClaI each represent a restriction enzyme cleavage site.
Figure 9:
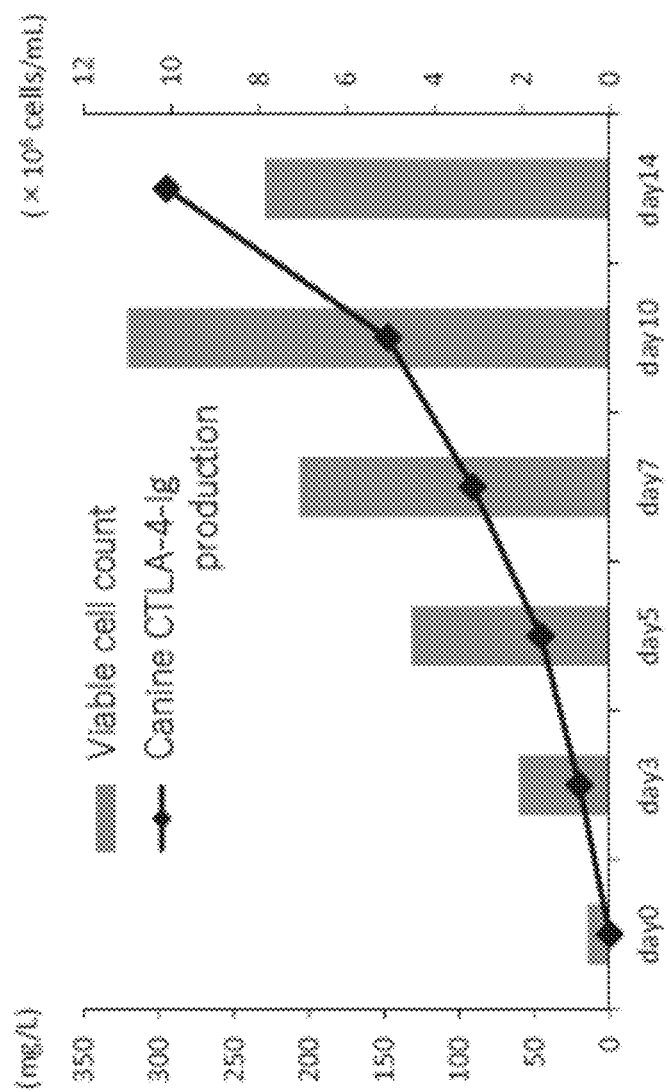
FIG. 9 Expression of canine CTLA-4-Ig by a high expression CHO cell line established with pDC62c5-U533 vector. Canine CTLA-4-Ig expression and viable cell count are shown for each of the indicated days during 14-day culture.

Gene sequences for canine CTLA-4 and canine IgG-D have already been registered at The National Center for Biotechnology Information (NCBI) (GenBank accession numbers; NM_001003106.1 and AF354267.1). An amino acid sequence having a putative extracellular region of canine CTLA-4 connected to the hinge as well as CH2 and CH3 regions of canine IgG-D was prepared and codon optimization for CHO cells was performed [SEQ ID NO: 15 (amino acid sequence) and SEQ ID NO: 16 (nucleotide sequence after codon optimization)]. Subsequently, gene synthesis was performed in such a manner that AscI restriction enzyme recognition sequence, Kozak sequence, canine CTLA-4-Ig sequence, and AsiSI restriction enzyme recognition sequence would be located in this order. Using restriction enzyme recognition sites, the synthesized genetic strand was integrated into the pDC62c5-U533 having only one site for foreign gene insertion (SEQ ID NO: 17; FIG. 8) at the cloning site (nucleotide sequences No. 1098 to No. 1108; AscI and AsiSI restriction enzyme recognition sequences between PRCMV5 and PABGH) in such a manner that the above-described sequences would be located in the above-described order, whereby a canine CTLA-4-Ig expression vector was constructed. This expression vector was linearized with restriction enzyme ClaI and then used to transfect CHO DG44 cells (CHO-DG44 (dhfr–/–)) (dihydrofolate reductase gene deficient cells) using Lipofectamine LTX (Thermo Fisher Scientific). Following 48 hours after transfection, the medium was exchanged with thymidine- and hypoxanthine-free Opti-CHO medium (Life Technologies) supplemented with 4 mM GlutaMAX-I (Life Technologies) for selection of transformants. As a result, stably expressing clones were obtained. Further, cloning of cells was performed by limiting dilution method and clones of high expression yield were selected by dot blotting and 3-day shaking culture test. The established CHO-DG44 cell clones capable of high-yield expression of canine CTLA-4-Ig were adapted to Dynamis medium (Life Technologies) supplemented with 4 mM GlutaMAX-I (Life Technologies) and cultured under shaking (125 rpm, 37° C., 8% $CO_2$) at a density of 5×10^5 cells/ml, with a liquid volume of 30 ml, in 125 ml culture flasks (Corning) for 14 days. At days 3, 5, 7 and 10 of culture, EfficientFeed B+(Life Technologies) tripled in concentration was added to the medium at 3.3% v/v. Further, at days 3, 5 and 7 of culture, 45% glucose in solution (Kanto Chemical Co., Inc.) was added to the medium to give final concentrations of 4, 4 and 6 g/L, respectively. As a result, approximately 300 mg/L of canine CTLA-4-Ig recombinant protein was expressed in the culture supernatant at day 14 (FIG. 9). The concentration of canine CTLA-4-Ig in the culture supernatant was quantified by sandwich ELISA using a goat anti-canine IgG1 polyclonal antibody (Bethyl Laboratories) and the number of viable cells were counted by trypan blue staining without including dead cells.

The canine CTLA-4-Ig produced was purified from the culture supernatant using Ab-Capcher ExTra (protein A mutant; ProteNova). For binding to resin, the open column method was used. As an equilibrating buffer and a washing buffer, phosphate-buffered physiological saline (PBS; pH 7.4) was used. As an elution buffer, 0.1 M Glycine-HCl was used. As a neutralization buffer, 1 M Tris-HCl was used. Using PD-MidiTrap G-25 (GE Healthcare), buffer replacement with PBS was performed. Purified canine CTLA-4-Ig was passed through a 0.2 µm filter and stored at 4° C. until use in subsequent experiments. Protein concentrations were quantified with Pierce BCA Protein Assay Kit (Thermo Fisher Scientific) and used in the subsequent experiments.

Figure 10:
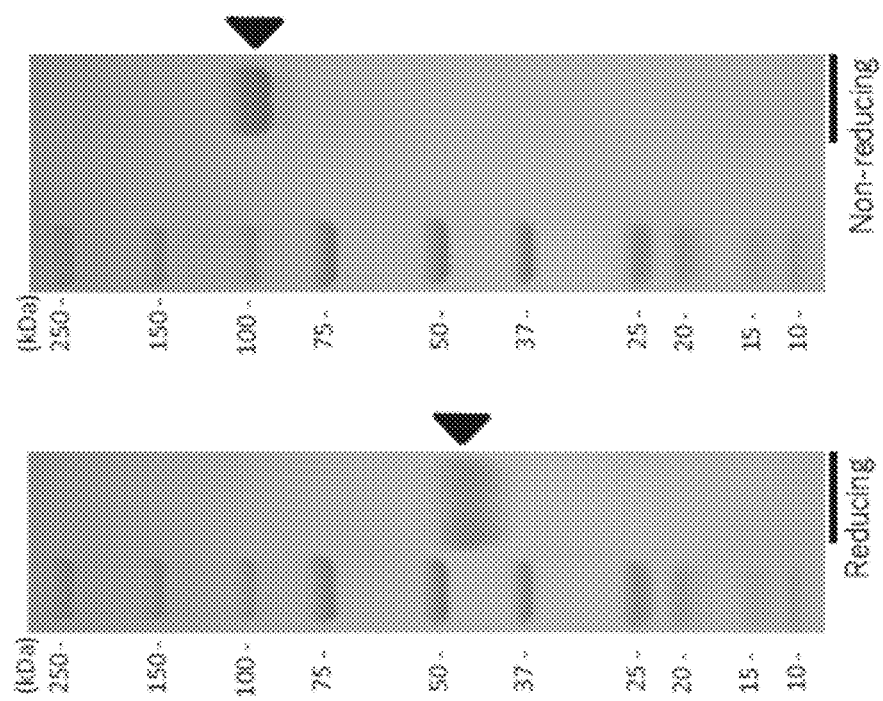
FIG. 10 SDS-PAGE images of canine CTLA-4-Ig purified from culture supernatant. Canine CTLA-4-Ig was electrophoresed under reducing and non-reducing conditions, and visualized by CBB staining. A single band was observed at around 45 kDa under reducing conditions and at around 90 kDa under non-reducing conditions. The detection of contamination bands was almost zero.

In order to check for the purity of the purified canine CTLA-4-Ig, Ig proteins were detected by SDS-PAGE and CBB staining. Using SuperSep Ace 5-20% gradient gel (Wako), the canine CTLA-4-Ig was electrophoresed under both reducing and non-reducing conditions. After staining with Quick-CBB kit (Wako), decoloring was performed in distilled water. A band was observed at positions corresponding to molecular weights of around 45 kDa (under reducing conditions) and around 90 kDa (under non-reducing conditions.) The molecular weight of canine CTLA-4-Ig as calculated from its amino acid sequence was approx. 79 kDa for dimer and approx. 39.5 kDa for monomer. The emergence of bands at positions corresponding to the larger molecular weights was assumed to result from glycosylation and other effects. Bands of seemingly contaminant proteins were hardly visible (FIG. 10).

[Example 13] Preparation of pDC62c5-U533-TRLH

Figure 11:
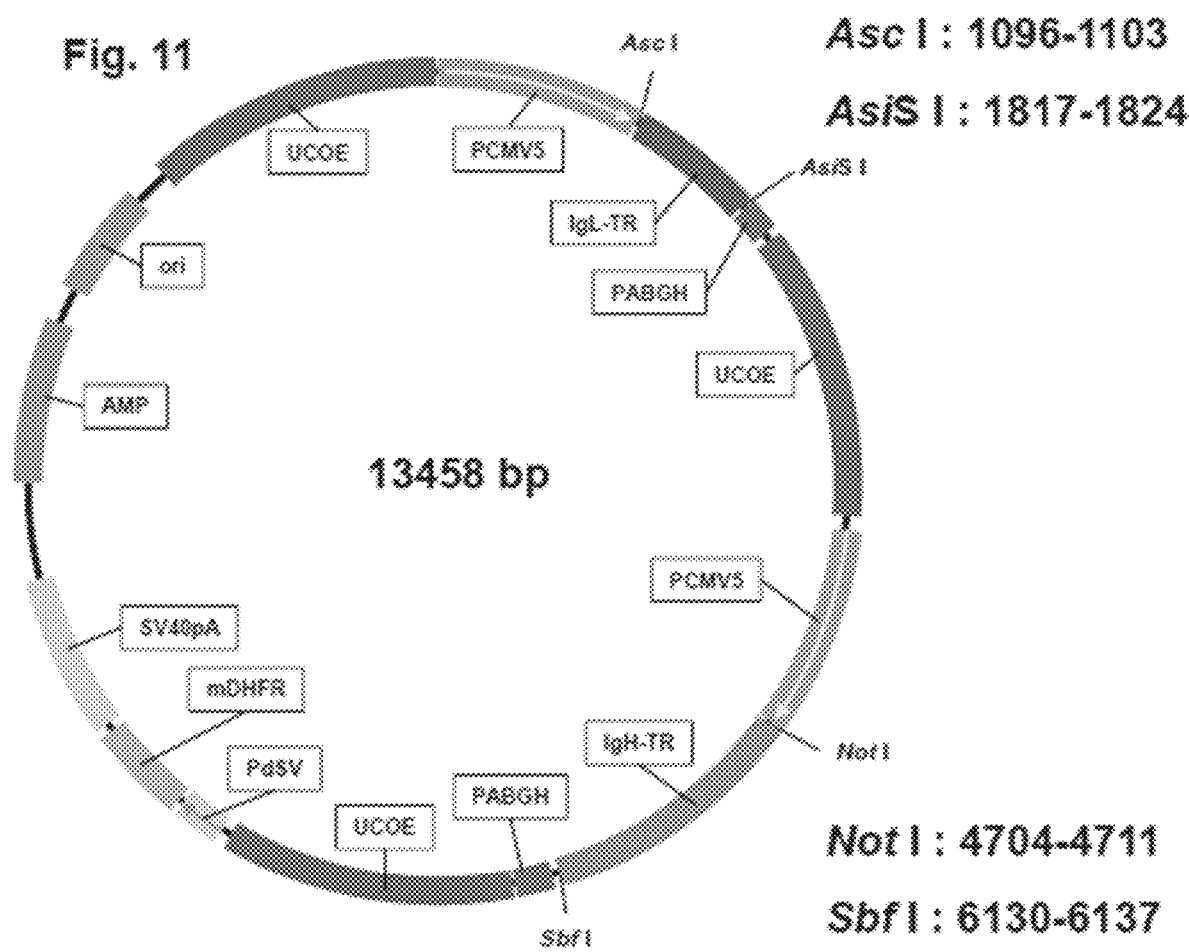
FIG. 11 This figure shows pDC62c5-U533-TRLH construct.

The nucleotide sequences No. 1098 to No. 1108 of pDC62c5-U533 were substituted with a cDNA encoding the light chain of a human trastuzumab (TRLH) (having an optimized Kozak added upstream of the initiation codon) as shown in SEQ ID NO: 18 and the nucleotide sequences No. 3993 to No. 4004 of pDC62c5-U533 were substituted with a cDNA encoding the heavy chain of the human trastuzumab (TRLH) (having the optimized Kozak added upstream of the initiation codon) as shown in SEQ ID NO: 19, whereby pDC62c5-U533-TRLH (FIG. 11) was constructed. The sequence of the optimized Kozak is shown in SEQ ID NO: 2.

Prior to gene transfer, the vector was linearized with a restriction enzyme ClaI.

[Example 14] Transfection of pDC62c5-U533-TRLH into CHO Cells, Selection, Productivity Test and Expression Stability Test 18 μg of pDC62c5-U533-TRLH was transfected into 15,000,000 CHO cells (CHO DG44 cells) in 125 ml culture flasks (Erlenmeyer Flask, Baffled, 125 ml, Vent Cap, cat #431405, Corning) using the Lipofectin method (with Free-Style MAX Reagent, Life Technologies).

The method of transfection was in accordance with the manufacturer's instructions for use. Following 48 hours after transfection, the number of cells was counted, and then the cells were diluted with CD OptiCHO medium (Life Technologies) supplemented with 4 mM GlutaMAX-I (Life Technologies). In a 96-well microtiter plate, mixing with 12,000 cells/well of non-transfected cells was conducted at a concentration of 400 transfected cells/well. The mixed cells were then seeded in 12 plates (1152 wells) and cultured in the presence of 8% carbon dioxide gas at 37° C. for approximately three weeks. From the viable cells, 188 HT-free medium resistant clones were randomly selected. The thus obtained HT-free medium resistant clones were transferred to a 24-well plate together with CD OptiCHO medium (Life Technologies) supplemented with 4 mM GlutaMAX-I (Life Technologies), and cultured therein.

Each clone (0.6 ml) was placed in a sterile tube and centrifuged at 300×g for 7 min. The supernatant was discarded, and the cells were suspended in 0.3 ml of a fresh medium (CD OptiCHO medium (Life Technologies) supplemented with 4 mM GlutaMAX-I (Life Technologies)), and cell counting was done. After the cells were diluted with a medium to give a viable cell density of 2×10^5 cells/ml, 0.4 ml of the dilution was transferred to a fresh 24-well plate and subjected to rotary shaking culture (125 rpm) in the presence of 8% carbon dioxide gas at 37° C. for 72 hrs. After culture, cell counting was done, followed by centrifugation at 9300×g for 2 min and collection of the supernatant.

Figure 12:
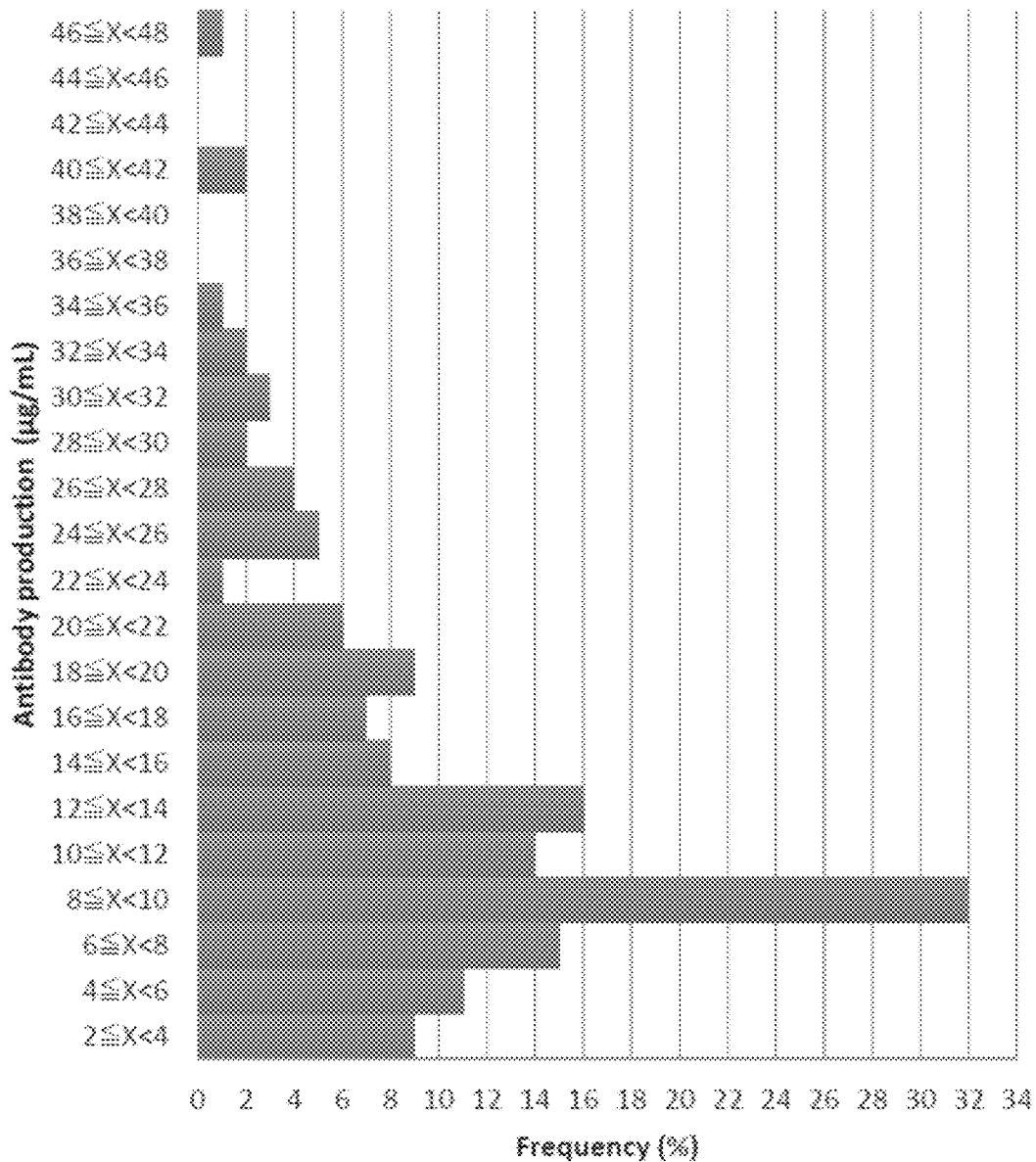
FIG. 12 This figure shows distribution of the expression level of an antibody produced by CHO cells transfected with pDC62c5-U533-TRLH (expression vector of the present invention) (data obtained by 3-day culture).

Subsequently, IgG concentration in the culture supernatant was measured by ELISA. As a result, the IgG yield from the clone of maximum production was 47.8 μg/ml/3 days, with 81 out of the 188 clones (43.1%) producing 10 μg/ml or more of IgG (FIG. 12).

Figure 13:
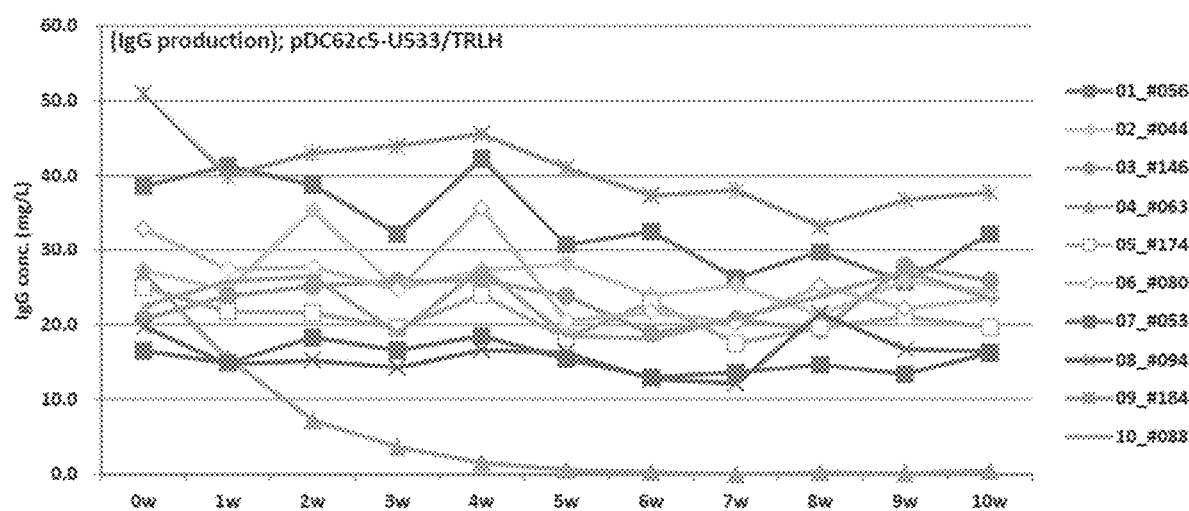
FIG. 13 This figure shows changes in the level of an antibody produced by CHO cells transfected with pDC62c5-U533-TRLH (expression vector of the present invention) (for 0 to 10 weeks from the start of culture in productivity test).

Next, top 10 clones in terms of IgG yield were selected and subjected to an expression stability test. In the expression stability test, subculture was started from a frozen stock of each clone. For adaptation culture, CD OptiCHO medium (Life Technologies) supplemented with 4 mM GlutaMAX-I (Life Technologies) and Dynamis medium (Life Technologies) supplemented with 4 mM GlutaMAX-I (Life Technologies) were used. As passaging progressed, the ratio of the latter medium was increased from 75:25 through 50:50 to 25:75, whereby the cells were adapted. After adaptation, an expression stability test was conducted. In subculture during the test period, cells were diluted using Dynamis medium (Life Technologies) supplemented with 4 mM GlutaMAX-I (Life Technologies) to give a density of 2 or 1.5×10^5 cells/ml and thereafter subjected to rotary shaking culture for 3 to 4 days. The resultant cells were diluted again to give a density of 2 or 1.5×10^5 cells/ml, and these operations were carried out repeatedly. At days 0, 7, 14, 21, 28, 35, 42, 49, 56, 63 and 70 from the start of test culture, cells were diluted to give a density of 2×10^5 cells/ml and 0.4 ml of the dilution was subjected to rotary shaking culture (125 rpm) on a 24-well plate for 72 hrs. The culture supernatant was collected and measured for IgG yield therein by ELISA. IgG yields from the 10 clones were 50.9-16.5 mg/L at week 0 and 37.0-0.5 mg/L at week 10. As regards the expression stability of pDC62c5-U533-TRLH-transfected cells, 8 out of the 10 clones retained 70% or more of IgG production capacity until week 8 as relative to the production capacity before preparation of the frozen stock; 1 clone retained 50% to less than 70% of IgG production capacity; and 1 clone retained less than 50% of IgG production capacity. At week 10, 9 clones retained 70% or more of IgG production capacity; and 1 clone retained less than 50% of IgG production capacity (FIG. 13).

Figure 14:
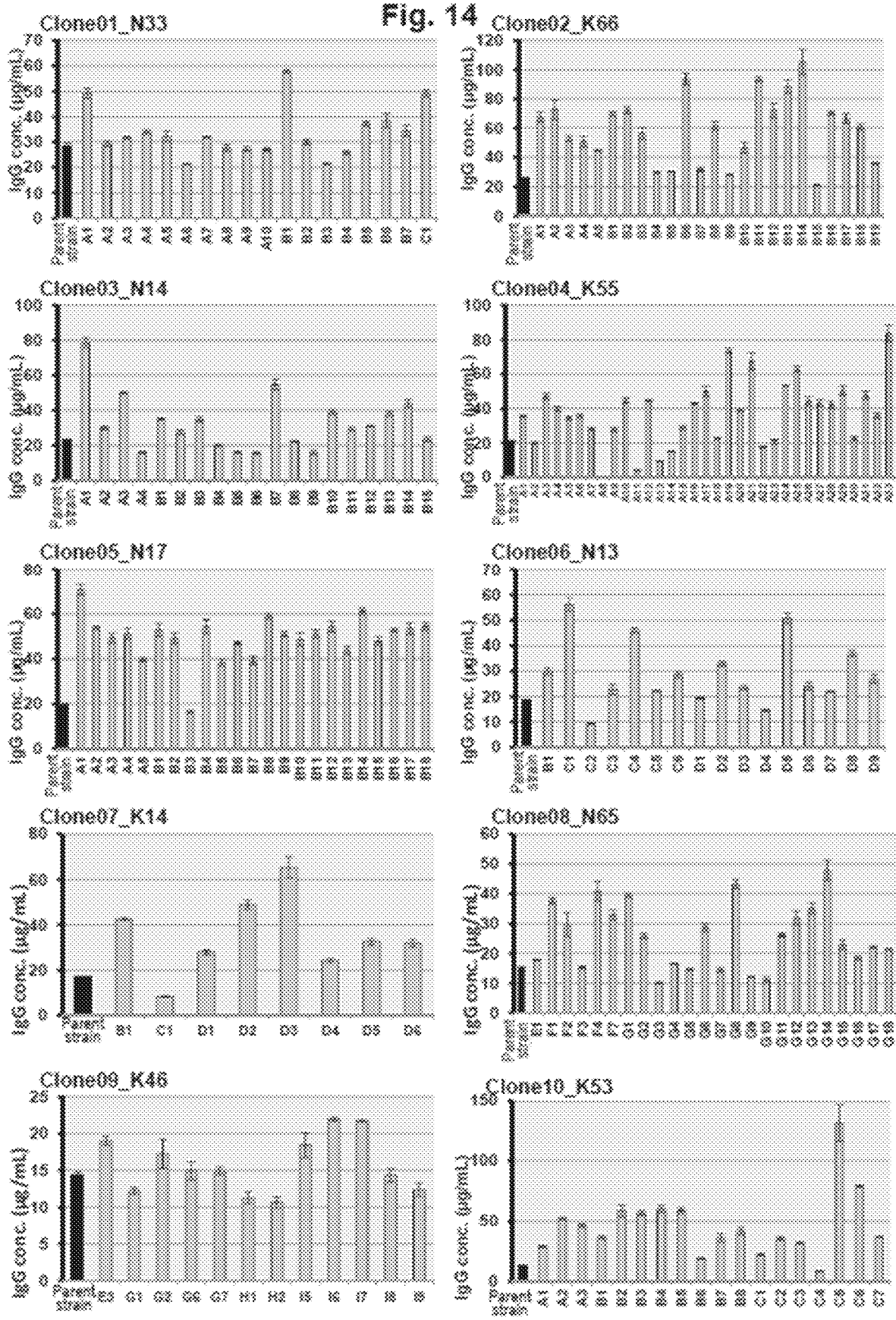
FIG. 14 This figure shows levels of an antibody as produced by cell strains obtained by culturing each of those clones in the presence of 60 nM MTX which had been obtained from the plates seeded with CHO cells (Clone01-10) transfected with pDC62c5-U533-OMLH (expression vector of the present invention) (data obtained by 3-day culture).

[Example 15] MTX Selection and Productivity Test of pDC62c5-U533-OMLH-Transfected CHO Cells As for the top 10 clones in terms of IgG yield (Clone01-10) that were obtained in Example 3, subculture from the frozen stock of each clone was performed for 2 or 3 passages. Then, cells were diluted with CD OptiCHO medium (Life Technologies) supplemented with 4 mM GlutaMAX-I (Life Technologies) and 60 nM MTX (Wako). For each clone, mixing with 12,000 cells/well of non-transfected cells was conducted at densities of 1, 3, 10, 30, 100, 300, 1000, 3000 and 10000 transfected cells/well in a 96-well microtiter plate. The mixed cells were then seeded in 10 plates (960 wells) (2 plates for each density) and cultured in the presence of 8% carbon dioxide gas at 37° C. for 3 to 4 weeks. MTX resistant clones were randomly selected from the viable cells. The resultant clones were transferred to a 24-well plate and cultured until cells occupied more than ⅓ of the base area in each well. As regards the cells grown in the 24-well plate, 0.5 ml of each clone was placed in a sterile tube and centrifuged at 300×g for 7 min. The supernatant was discarded and the cells were suspended in 0.3 ml of a fresh medium (CD OptiCHO medium (Life Technologies)

supplemented with 4 mM GlutaMAX-I (Life Technologies) and 60 nM MTX (Wako)), and cell counting was done. After the cells were diluted with a medium to give a viable cell density of 2×10^5 cells/ml, 0.4 ml of the dilution was transferred to a fresh 24-well plate and subjected to rotary shaking culture (125 rpm) in the presence of 8% carbon dioxide gas at 37° C. for 72 hrs. After culture, cell counting was done, followed by centrifugation at 9300×g for 2 min and collection of the supernatant. Subsequently, IgG concentration in the culture supernatant was measured by ELISA (FIG. 14).

As regards Clone01, 18 clones were obtained from the plates seeded at densities of 1, 3 and 10 cells/well, following 29 to 32 days after seeding. The IgG yield from the clone of maximum production was 58.0 μg/ml/3 days, which was twice the value for the parent strain (28.5 μg/ml/3 days).

As regards Clone02, 24 clones were obtained from the plates seeded at densities of 1 and 3 cells/well, following 22 to 32 days after seeding. The IgG yield from the clone of maximum production was 105.5 μg/ml/3 days, which was 4.1 times the value for the parent strain (25.8 μg/ml/3 days).

As regards Clone03, 19 clones were obtained from the plates seeded at densities of 1 and 3 cells/well, following 22 to 32 days after seeding. The IgG yield from the clone of maximum production was 78.7 μg/ml/3 days, which was 3.4 times the value for the parent strain (23.0 μg/ml/3 days).

As regards Clone04, 33 clones were obtained from the plate seeded at a density of 1 cell/well, following 22 to 32 days after seeding. The IgG yield from the clone of maximum production was 83.7 μg/ml/3 days, which was 4.0 times the value for the parent strain (20.9 μg/ml/3 days).

As regards Clone05, 23 clones were obtained from the plates seeded at densities of 1 and 3 cells/well, following 27 to 39 days after seeding. The IgG yield from the clone of maximum production was 71.0 μg/ml/3 days, which was 3.7 times the value for the parent strain (19.2 μg/ml/3 days).

As regards Clone06, 16 clones were obtained from the plates seeded at densities of 3, 10 and 30 cells/well, following 26 to 39 days after seeding. The IgG yield from the clone of maximum production was 56.2 μg/ml/3 days, which was 3.0 times the value for the parent strain (18.4 μg/ml/3 days).

As regards Clone07, 8 clones were obtained from the plates seeded at densities of 3, 10 and 30 cells/well, following 29 to 39 days after seeding. The IgG yield from the clone of maximum production was 65.3 μg/ml/3 days, which was 3.8 times the value for the parent strain (17.1 μg/ml/3 days).

As regards Clone08, 24 clones were obtained from the plates seeded at densities of 100, 300 and 1000 cells/well, following 27 to 41 days after seeding. The IgG yield from the clone of maximum production was 47.9 μg/ml/3 days, which was 3.1 times the value for the parent strain (15.1 μg/ml/3 days).

As regards Clone09, 12 clones were obtained from the plates seeded at densities of 100, 1000, 3000 and 10000 cells/well, following 26 to 41 days after seeding. The IgG yield from the clone of maximum production was 21.9 μg/ml/3 days, which was 1.5 times the value for the parent strain (14.3 μg/ml/3 days).

As regards Clone10, 18 clones were obtained from the plates seeded at densities of 1, 3 and 10 cells/well, following 22 to 39 days after seeding. The IgG yield from the clone of maximum production was 131.4 μg/ml/3 days, which was 10.1 times the value for the parent strain (13.0 μg/ml/3 days).

All publications, patents and patent applications cited herein are incorporated herein by reference in their entirety.

INDUSTRIAL APPLICABILITY

According to the present invention, it is possible to provide expression vectors that enable production of foreign gene-derived proteins at high levels using dihydrofolate reductase gene deficient mammal cells as host. With the expression vector of the present invention, it is also possible to produce those proteins which have post-translational modifications inherent in mammals, as well as high biological activity. Therefore, it is possible to greatly reduce the production cost of proteinaceous useful substances such as biopharmaceuticals.

Furthermore, since the method of producing proteins by the present invention does not use virus or other microorganisms, highly safe protein production is possible.

SEQUENCE LISTING FREE TEXT

Nucleotide sequences of UCOE.

<SEQ ID NO: 1>

```
GGCCCTCCGCGCCTACAGCTCAAGCCACATCCGAAGGGGGAGGGAGCCGGGAGCTGCGCGCGGGGCCGCCGGGGGG
AGGGGTGGCACCGCCCACGCCGGGCGGCCACGAAGGGCGGGGCAGCGGGCGCGCGCGCGGCGGGGGGAGGGGCC
GGCGCCGCGCCCGCTGGGAATTGGGGCCCTAGGGGGAGGGCGGAGGCGCCGACGACCGCGGCACTTACCGTTCGCG
GCGTGGCGCCCGGTGGTCCCCAAGGGGAGGGAAGGGGGAGGCGGGGCGAGGACAGTGACCGGAGTCTCCTCAGCG
GTGGCTTTTCTGCTTGGCAGCCTCAGCGGCTGGCGCCAAAACCGGACTCCGCCCACTTCCTCGCCCGCCGGTGCGAG
GGTGTGGAATCCTCCAGACGCTGGGGGAGGGGGAGTTGGGAGCTTAAAAACTAGTACCCCTTTGGGACCACTTTCAG
CAGCGAACTCTCCTGTACACCAGGGGTCAGTTCCACAGACGCGGGCCAGGGGTGGGTCATTGCGGCGTGAACAATAA
TTTGACTAGAAGTTGATTCGGGTGTTTCCGGAAGGGGCCGAGTCAATCCGCCGAGTTGGGGCACGGAAAACAAAAAG
GGAAGGCTACTAAGATTTTTCTGGCGGGGGTTATCATTGGCGTAACTGCAGGGACCACCTCCCGGGTTGAGGGGGCT
GGATCTCCAGGCTGCGGATTAAGCCCCTCCCGTCGGCGTTAATTTCAAACTGCGCGACGTTTCTCACCTGCCTTCGCC
AAGGCAGGGGCCGGGACCCTATTCCAAGAGGTAGTAACTAGCAGGACTCTAGCCTTCCGCAATTCATTGAGCGCATTT
ACGGAAGTAACGTCGGGTACTGTCTCTGGCCGCAAGGGTGGGAGGAGTACGCATTTGGCGTAAGGTGGGCGTAGAG
CCTTCCCGCCATTGGCGGCGGATAGGGCGTTTACGCGACGGCCTGACGTAGCGGAAGACGCCTTAGTGGGGGGAAG
GTTCTAGAAAAGCGGCGGCAGCGGCTCTAGCGGCAGTAGCAGCAGCGCCGGGTCCCGTGCGGAGGTGCTCCTCGCA
GAGTTGTTTCTCCAGCAGCGGCAGTTCTCACTACAGCGCCAGGACGAGTCCGGTTCGTGTTCGTCCGCGGAGATCTCT
CTCATCTCGCTCGGCTGCGGGAAATCGGGCTGAAGCGACTGAGTCCGCGATGGAGGTAACGGGTTTGAAATCAATGA
GTTATTGAAAAGGGCATGGCGAGGCCGTTGGCGCCTCAGTGGAAGTCGGCCAGCCGCCTCCGTGGGAGAGAGGCAG
GAAATCGGACCAATTCAGTAGCAGTGGGGCTTAAGGTTTATGAACGGGGTCTTGAGCGGAGGCCTGAGCGTACAAAC
AGCTTCCCCACCCTCAGCCTCCCGCGCCATTTCCCTTCACTGGGGGTGGGGATGGGGAGCTTTCACATGGCGGAC
GCTGCCCCGCTGGGGTGAAAGTGGGGCGCGGAGGCGGGACTTCTTATTCCCTTTCTAAAGCACGCTGCTTCGGGGGC
CACGGCGTCTCCTCGGA
```

SEQUENCE LISTING FREE TEXT

This sequence shows an optimized Kozak sequence. In this sequence, ATG is the initiation codon.
<SEQ ID NO: 2>
CCGCCGCCACCATGG Entire sequence of pDC62c5-U533.
<SEQ ID NO: 3>
CGATGTACGGGCCAGATATACGCGTTGACATTGATTATTGACTAGTCGCGTTACATAACTTACGGTAAATGGCCCGCCT
GGCTGACCGCCCAACGACCCCCGCCCATTGACGTCAATAATGACGTATGTTCCCATAGTAACGCCAATAGGGACTTTC
CATTGACGTCAATGGGTGGAGTATTTACGGTAAACTGCCCACTTGGCAGTACATCAAGTGTATCATATGCCAAGTCCGC
CCCCTATTGACGTCAATGACGGTAAATGGCCCGCCTGGCATTATGCCCAGTACATGACCTTACGGGACTTTCCTACTTG
GCAGTACATCTACGTATTAGTCATCGCTATTACCATGGTGATGCGGTTTTGGCAGTACACCAATGGGCGTGGATAGCGG
TTTGACTCACGGGGATTTCCAAGTCTCCACCCCATTGACGTCAATGGGAGTTTGTTTTGGCACCAAAATCAACGGGAC
TTTCCAAAATGTCGTAATAACCCCGCCCCGTTGACGCAAATGGGCGGTAGGCGTGTACGGTGGGAGGTCTATATAAGC
AGAGCTCGTTTAGTGAACCGTCAGATCCTCACTCTCTTCCGCATCGCTGTCTGCGAGGGCCAGCTGTTGGGCTCGCGG
TTGAGGACAAACTCTTCGCGGTCTTTCCAGTACTCTTGGATCGGAAACCCGTCGGCCTCCGAACGGTACTCCGCCACC
GAGGGACCTGAGCGAGTCCGCATCGACCGGATCGGAAAACCTCTCGAGAAAGGCGTCTAACCAGTCACAGTCGCAAG
GTAGGCTGAGCACCGTGGCGGGCGGCAGCGGGTGGCGGTCGGGGTTGTTTCTGGCGGAGGTGCTGCTGATGATGTA
ATTAAAGTAGGCGGTCTTGAGACGGCGGATGGTCGAGGTGAGGTGTGGCAGGCTTGAGATCCAGCTGTTGGGGTGAG
TACTCCCTCTCAAAAGCGGGCATGACTTCTGCGCTAAGATTGTCAGTTTCCAAAAACGAGGAGGATTTGATATTCACCT
GGCCCGATCTGGCCATACACTTGAGTGACAATGACATCCACTTTGCCTTTCTCTCCACAGGTGTCCACTCCCAGGTCC
AAGGCGCGCCGCGATCGCGCCTCGACTGTGCCTTCTAGTTGCCAGCCATCTGTTGTTTGCCCCTCCCCCGTGCCTTCC
TTGACCCTGGAAGGTGCCACTCCCACTGTCCTTTCCTAATAAAATGAGGAAATTGCATCGCATTGTCTGAGTAGGTGTC
ATTCTATTCTGGGGGGTGGGGTGGGGCAGGACAGCAAGGGGGAGGATTGGGAAGACAATAGCAGGCATGCTGGGGA
GGATCTCCGCGGGGCCCTCCGCGCCTACAGCTCAAGCCACATCCGAAGGGGGAGGGAGCCGGGAGCTGCGCGCGGG
GCCGCCGGGGGAGGGGTGGCACCGCCCACGCCGGGCGGCCACGAAGGGCGGGGCAGCGGGCGCGCGCGCGGCGG
GGGGAGGGGCCGGCGCCGCGCCCGCTGGGAATTGGGGCCCTAGGGGGCCGGGCCCGACGACCCGACCGCCGGCAC
TTACCGTTCGCGGCGTGGCGCCCGGTGGTCCCCAAGGGGAGGGAAGGGGGAGGCGGGGCGAGGACAGTGACCGGA
GTCTCCTCAGCGGTGGCTTTTCTGCTTGGCAGCCTCAGCGGCTGGCGCCAAAACCGGACTCCGCCCACTTCCTCGCC
CGCCGGTGCGAGGGTGTGGAATCCTCCAGACGCTGGGGAGGGGGAGTTGGGAGCTTAAAAACTAGTACCCCTTTGG
GACCACTTTCAGCAGCGAACTCTCCTGTACACCAGGGGTCAGTTCCACAGACGCGGGCCAGGGTGGGTCATTGCGGCG
CGTGAACAATAATTTGACTAGAAGTTGATTCGGGTGTTTCCGGAAGGGGCCGAGTCAATCCGCCGAGTTGGGGCACG
GAAAACAAAAGGGAAGGCTACTAAGATTTTTCTGGCGGGGTTATCATTGGCGTAACTGCAGGGACCACCTCCCGGG
TTGAGGGGGCTGGATCTCCAGGCTGCGGATTAAGCCCCTCCCGTCGGCGTTAATTTCAAACTGCGCGACGTTTCTCAC
CTGCCTTCGCCAAGGCAGGGGCCGGGACCCTATTCCAAGAGGTAGTAACTAGCAGGACTCTAGCCTTCCGCAATTCAT
TGAGCGCATTTACGGAAGTAACGTCGGGTACTGTCTCTGGCCGCAAGGGTGGGAGGAGTACGCATTTGGCGTAAGGT
GGGGCGTAGAGCCTTCCCGCCATTGGCGGCGGATAGGGCGTTTACGCGACGGCCTGACGTAGCGGAAGACGCCTTAG
TGGGGGGAAGGTTCTAGAAAAGCGGCGGCAGCGGCTCTAGCGGCAGTAGCAGCAGCGCCGGGTCCCGTGCGGAGG
TGCTCCTCGCAGAGTTGTTTCTCCAGCAGCGGCAGTTCTCACTACAGCGCCAGGACGAGTCCGGTTCGTGTTCGTCCG
CGGAGATCTCTCTCATCTCGCTCGGCTGCGGGAAATCGGGCTGAAGCGACTGAGTCCGCGATGGAGGTAACGGGTTT
GAAATCAATGAGTTATTGAAAAGGGCATGGCGAGGCCGTTGGCGCCTCAGTGGAAGTCGGCCAGCCGCCTCCGTGGG
AGAGAGGCAGGAAATCGGACCAATTCAGTAGCAGTGGGGCTTAAGGTTTATGAACGGGGTCTTGAGCGGAGGCCTGA
GCGTACAAACAGCTTCCCCACCCTCAGCCTCCCGGCGCCATTTCCCTTCACTGGGGGTGGGGATGGGGAGCTTTCA
CATGGCGGACGCTGCCCCGCTGGGGTGAAAGTGGGGCGCGGAGGCGGACTTCTTATTCCCTTTCTAAAGCACGCTG
CTTCGGGGGCCACGGCGTCTCCTCGGAGAATTCCGATGTACGGGCCAGATATACGCGTTGACATTGATTATTGACTAG
TCGCGTTACATAACTTACGGTAAATGGCCCGCCTGGCTGACCGCCCAACGACCCCCGCCCATTGACGTCAATAATGAC
GTATGTTCCCATAGTAACGCCAATAGGGACTTTCCATTGACGTCAATGGGTGGAGTATTTACGGTAAACTGCCCACTTG
GCAGTACATCAAGTGTATCATATGCCAAGTCCGCCTATTGACGTCAATGACGGTAAATGGCCCGCCTGGCATTATG
CCCAGTACATGACCTTACGGGACTTTCCTACTTGGCAGTACATCTACGTATTAGTCATCGCTATTACCATGGTGATGCG
GTTTTGGCAGTACACCAATGGGCGTGGATAGCGGTTTGACTCACGGGGATTTCCAAGTCTCCACCCCATTGACGTCAA
TGGGAGTTTGTTTTGGCACCAAAATCAACGGGACTTTCCAAAATGTCGTAATAACCCCGCCCCGTTGACGCAAATGGG
CGGTAGGCGTGTACGGTGGGAGGTCTATATAAGCAGAGCTCGTTTAGTGAACCGTCAGATCCTCACTCTCTTCCGCAT
CGCTGTCTGCGAGGGCCAGCTGTTGGGCTCGCGGTTGAGGACAAACTCTTCGCGGTCTTTCCAGTACTCTTGGATCG
GAAACCCGTCGGCCTCCGAACGGTACTCCGCCACCGAGGGACCTGAGCGAGTCCGCATCGACCGGATCGGAAAACCT
CTCGAGAAAGGCGTCTAACCAGTCACAGTCGCAAGGTAGGCTGAGCACCGTGGCGGGCGGCAGCGGGTGGCGGTCG
GGGTTGTTTCTGGCGGAGGTGCTGCTGATGATGTAATTAAAGTAGGCGGTCTTGAGACGGCGGATGGTCGAGGTGAG
GTGTGGCAGGCTTGAGATCCAGCTGTTGGGGTGAGTACTCCCTCTCAAAAGCGGGCATGACTTCTGCGCTAAGATTGT
CAGTTTCCAAAAACGAGGAGGATTTGATATTCACCTGGCCCGATCTGGCCATACACTTGAGTGACAATGACATCCACTT
TGCCTTTCTCTCCACAGGTGTCCACTCCCAGGTCCAAGCGGCCGCCCTGCAGGGCCTCGACTGTGCCTTCTAGTTGCC
AGCCATCTGTTGTTTGCCCCTCCCCCGTGCCTTCCTTGACCCTGGAAGGTGCCACTCCCACTGTCCTTTCCTAATAAAA
TGAGGAAATTGCATCGCATTGTCTGAGTAGGTGTCATTCTATTCTGGGGGGTGGGGTGGGGCAGGACAGCAAGGGGG
AGGATTGGGAAGACAATAGCAGGCATGCTGGGGAGGATCCGCGGGGCCCTCCGCGCCTACAGCTCAAGCCACATC
CGAAGGGGAGGGAGCCGGGAGCTGCGCGCGGGGCCGCGGGGGAGGGGTGGCACCGCCCACGCCGGGCGGCCA
CGAAGGGCGGGGCAGCGGGCGCGCGCGCGGCGGGGGAGGGGCCGGCGCCGCGCCCGCTGGGAATTGGGGCCCTA
GGGGGCCGGGCCCGACGACCCGACCACTTACCGTTCGCGGCGTGGCGCCCGGTGGTCCCCAAGGGGAGG
GAAGGGGGAGGCGGGGCGAGGACAGTGACCGGAGTCTCCTCAGCGGTGGCTTTTCTGCTTGGCAGCCTCAGCGGCT
GGCGCCAAAACCGGACTCCGCCCACTTCCTCGCCCGCCGGTGCGAGGGTGTGGAATCCTCCAGACGCTGGGGAGG
GGGAGTTGGGAGCTTAAAAACTAGTACCCCTTTGGGACCACTTTCAGCAGCGAACTCTCCTGTACACCAGGGGTCAGT
TCCACAGACGCGGGCCAGGGTGGGTCATTGCGGCGTGAACAATAATTTGACTAGAAGTTGATTCGGGTGTTTCCGG
AAGGGGCCGAGTCAATCCGCCGAGTTGGGGCACGGAAAACAAAAGGGAAGGCTACTAAGATTTTTCTGGCGGGGGT
TATCATTGGCGTAACTGCAGGGACCACCTCCCGGGTTGAGGGGCTGGATCTCCAGGCTGCGGATTAAGCCCCTCCC
GTCGGCGTTAATTTCAAACTGCGCGACGTTTCTCACCTGCCTTCGCCAAGGCAGGGGCCGGGACCCTATTCCAAGAGG
TAGTAACTAGCAGGACTCTAGCCTTCCGCAATTCATTGAGCGCATTTACGGAAGTAACGTCGGGTACTGTCTCTGGCC
GCAAGGGTGGGAGGAGTACGCATTTGGCGTAAGGTGGGCGTAGAGCCTTCCCGCCATTGGCGGCGGATAGGGCGTT
TACGCGACGGCCTGACGTAGCGGAAGACGCCTTAGTGGGGGGAAGGTTCTAGAAAAGCGGCGGCAGCGGCTCTAG
CGGCAGTAGCAGCAGCGCCGGGTCCCGTGCGGAGGTGCTCCTCGCAGAGTTGTTTCTCCAGCAGCGGCAGTTCTCAC

SEQUENCE LISTING FREE TEXT

```
TACAGCGCCAGGACGAGTCCGGTTCGTGTTCGTCCGCGGAGATCTCTCTCATCTCGCTCGGCTGCGGGAAATCGGGC
TGAAGCGACTGAGTCCGCGATGGAGGTAACGGGTTTGAAATCAATGAGTTATTGAAAAGGGCATGGCGAGGCCGTTG
GCGCCTCAGTGGAAGTCGGCCAGCCGCCTCCGTGGGAGAGAGGCAGGAAATCGGACCAATTCAGTAGCAGTGGGGC
TTAAGGTTTATGAACGGGGTCTTGAGCGGAGGCCTGAGCGTACAAACAGCTTCCCCACCCTCAGCCTCCCGGCGCCAT
TTCCCTTCACTGGGGGTGGGGGATGGGGAGCTTTCACATGGCGGACGCTGCCCCGCTGGGGTGAAAGTGGGGCGCG
GAGGCGGGACTTCTTATTCCCTTTCTAAAGCACGCTGCTTCGGGGGCCACGGCGTCTCCTCGGAACCGGTTGTGGAAT
GTGTGTCAGTTAGGGTGTGGAAAGTCCCCAGGCTCCCCAGCAGGCAGAAGTATGCAAAGCATGCATCTCAATTAGTCA
GCAACCATAGTCCCGCCCCTAACTCCGCCCATCCCGCCCCTAACTCCGCCCAGTTCCGCCCATTCTCCGCCCCATGGC
TGACTAATTTTTTTATTTATGCAGAGGCCGAGGCCGCCTCGGCCTCTGAGCTATTCCAGAAGTAGTGAGGAGGCTTTT
TTGGAGGCCTAGGCTTTTGCAAAAAAGCTGCAGATGGTACGACCATTAAATTGTATTGTAGCAGTATCACAAATATGG
GTATTGGTAAAAATGGTGATTTACCATGGCCACCATTACGAAATGAATTTAAATATTTTCAACGAATGACTACTACTTCA
TCAGTAGAAGGTAAACAAAATTTAGTAATTATGGGTCGAAAAACTTGGTTTTCAATTCCTGAGAAGAATCGACCTTTAA
AGGACAGAATTAATATAGTTCTCAGTAGAGAACTCAAAGAACCACCACGAGGAGCTCATTTTCTTGCCAAAAGTTTGG
ATGATGCCTTAAGACTTATTGAACAACCGGAATTGGCAAGTAAAGTAGACATGGTTTGGATAGTCGGAGGCAGTTCTG
TTTACCAGGAAGCCATGAATCAACCAGGCCACCTCAGACTCTTTGTGACAAGGATCATGCAGGAATTTGAAAGTGACA
CGTTTTTCCCAGAAATTGATTTGGGGAAATATAAACTTCTCCCAGAATACCCAGGCGTCCTCTCTGAGGTCCAGGAGG
AAAAAGGCATCAAGTATAAGTTTGAAGTCTACGAGAAGAAAGACTAAAGATCCGTGACATAATTGGACAAACTACCTAC
AGAGATTTAAAGCTCTAAGGTAAATATAAAATTTTTAAGTGTATAATGTGTTAAACTACT-
GATTCTAATTGTTTGTGTATT
TTAGATTCCAACCTATGGAACTGATGAATGGGAGCAGTGGTGGAATGCCTTTAATGAGGAAAACCTGTTTTGCTCAGA
AGAAATGCCATCTAGTGATGATGAGGCTACTGCTGACTCTCAACATTCTACTCCTCCAAAAAAGAAGAGAAAGGTAGA
AGACCCCAAGGACTTTCCTTCAGAATTGCTAAGTTTTTTGAGTCATGCTGTGTTTAGTAATAGAACTCTTGCTTGCTTT
GCTATTTACACCACAAAGGAAAAAGCTGCACTGCTATACAAGAAAATTATGGAAAAATATTCTGTAACCTTTATAAGTAG
GCATAACAGTTATAATCATAACATACTGTTTTTTCTTACTCCACACAGGCAT-
AGAGTGTCTGCTATTAATAACTATGCTCA
AAAATTGTGTACCTTTAGCTTTTTAATTTGTAAAGGGGTTAATAAGGAATATTTGATGTATAGTGCCTTGACTAGAGATC
ATAATCAGCCATACCACATTTGTAGAGGTTTTACTTGCTTTAAAAAACCTCCCACACCTCCCCCTGAACCTGAAACATA
AAATGAATGCAATTGTTGTTGTTAACTTGTTTATTGCAGCTTATAATGGTTACAAATAAAGCAATAGCATCACAAATTTC
ACAAATAAAGCATTTTTTTCACTGCATTCTAGTTGTGGTTTGTCCAAACTCATCAATGTATCTTATCATGTCTGGGCCCA
TCGATGCCGACGTAGCGCCTGATGCGGTATTTTCTCCTTACGCATCGTGCGGTATTTCACACCGCATATGGTGCACTC
TCAGTACAATCTGCTCTGATGCCGCATAGTTAAGCCAGCCCCGACACCCGCCAACACCCGCTGACGCGCCCTGACGGG
CTTGTCTGCTCCCGGCATCCGCTTACAGACAAGCTGTGACCGTCTCCGGGAGCTGCATGTGTCAGAGGTTTTCACCGT
CATCACCGAAACGCGCGAGACGAAAGGGCCTCGTGATACGCCTATTTTTATAGGTTAATGTCATGATAATAATGGTTTC
TTAGACGTCAGGTGGCACTTTTCGGGGAAATGTGCGCGGAACCCCTATTTGTTTATTTTTCTAAATACATTCAAATATGT
ATCCGCTCATGAGACAATAACCCTGATAAATGCTTCAATAATATTGAAAAAGGAAGATGTAGAATTCAACATTTCCGT
GTCGCCCTTATTCCCTTTTTTGCGGCATTTTGCCTTCCTGTTTTTGCTCACCCAGAAACGCTGGTGAAAGTAAAAGATG
CTGAAGATCAGTTGGGTGCACGAGTGGGTTACATCGAACTGGATCTCAACAGCGGTAAGATCCTTGAGAGTTTTCGCC
CCGAAGAACGTTTTCCAATGATGAGCACTTTTAAAGTTCTGCTATGTGGCGCGGTATTATCCCGTATTGACGCCGGGCA
AGAGCAACTCGGTCGCCGCATACACTATTCTCAGAATGACTTGGTTGAGTACTCACCAGTCACAGAAAAGCATCTTAC
GGATGGCATGACAGTAAGAGAATTATGCAGTGCTGCCATAACCATGAGTGATAACACTGCGGCCAACTTACTTCTGAC
AACGATCGGAGGACCGAAGGAGCTAACCGCTTTTTTGCACAACATGGGGGATCATGTAACTCGCCTTGATCGTTGGGA
ACCGGAGCTGAATGAAGCCATACCAAACGACGAGCGTGACACCACGATGCCTGTAGCAATGGCAACAACGTTGCGCA
AACTATTAACTGGCGAACTACTTACTCTAGCTTCCCGGCAACAATTAATAGACTGGATGGAGGCGGATAAAGTTGCAGG
ACCACTTCTGCGCTCGGCCCTTCCGGCTGGCTGGTTTATTGCTGATAAATCTGGAGCCGGTGAGCGTGGGTCTCGCGG
TATCATTGCAGCACTGGGGCCAGATGGTAAGCCCTCCCGTATCGTAGTTATCTACACGACGGGGAGTCAGGCAACTAT
GGATGAACGAAATAGACAGATCGCTGAGATAGGTGCCTCACTGATTAAGCATTGGTAACTGTCAGACCAAGTTTACTC
ATATATACTTTAGATTGATTTAAAACTTCATTTTTAATTTAAAAGGATCTAGGTGAA-
GATCCTTTTTGATAATCTCATGAC
CAAAATCCCTTAACGTGAGTTTTCGTTCCACTGAGCGTCAGACCCCGTAGAAAAGATCAAAGGATCTTCTTGAGATCCT
TTTTTTCTGCGCGTAATCTGCTGCTTGCAAACAAAAAAACCACCGCTACCAGCGGTGGTTTGTTTGCCGGATCAAGAG
CTACCAACTCTTTTTCCGAAGGTAACTGGCTTCAGCAGAGCGCAGATACCAAATACTGTTCTTCTAGTGTAGCCGTAGT
TAGGCCACCACTTCAAGAACTCTGTAGCACCGCCTACATACCTCGCTCTGCTAATCCTGTTACCAGTGGCTGCTGCCAG
TGGCGATAAGTCGTGTCTTACCGGGTTGGACTCAAGACGATAGTTACCGGATAAGGCGCAGCGGTCGGGCTGAACGG
GGGGTTCGTGCACACAGCCCAGCTTGGAGCGAACGACCTACACCGAACTGAGATACCTACAGCGTGAGCTATGAGAA
AGCGCCACGCTTCCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACTTGAGCGTCGATTTT
TGTGATGCTCGTCAGGGGGGCGGAGCCTATGGAAAAACGCCAGCAACGCGGCCTTTTTACGGTTCCTGGCCTTTTGCT
GGCCTTTTGCTCACATGTTCTTTCCTGCGTTATCCCCTGATTCTGTGGATAACCGTATTACCGCCTTTGAGTGAGCTGA
TACCGCTCGCCGCAGCCGAACGACCGAGCGCAGCGAGTCAGTGAGCGAGGAAGCGGAAGAGCGCCCAATACGCAAA
CCGCCTCTCCCCGCGCGTTGGCCGATTCATTAATGCAGCTGGCCCTCGTGATACGCCTAAGCTCAAGCCACATCCGAAGG
GGGAGGGAGCCGGGAGCTGCGCGCGGGGCCGCCGGGGGAGGGTGGCACCGCCCACGCCGGGCGGCCACGAAGG
GCGGGGCAGCGGGCGCGCGCGGCGGGGGAGGGCCGGCGCCGCGCCCGCTGGGAATTGGGGCCCTAGGGGGA
GGGCGGAGGCGCCGACGACCGCGGCACTTACCGTTCGCGGCGTGCGCCCGGTGGTCCCCAAGGGGAGGGAAGGG
GGAGGCGGGGCGAGGACAGTGACCGGAGTCTCCTCAGCGGTGGCTTTTCTGCTTGGCAGCCTCAGCGGCTGGCGCC
AAAACCGGACTCCGCCCACTTCCTCGCCCGCCGGTGCGAGGGTGTGGAATCCTCCAGACGCTGGGGAGGGGAGT
TGGGAGCTTAAAACTAGTACCCCTTTGGGACCACTTTCAGCAGCGAACTCTCCTGTACACCAGGGGTCAGTTCCACA
GACGCGGGCCAGGGGTGGGTCATTGCGGCGTGAACAATAATTTGACTAGAAGTTGATTCGGGTGTTTCCGGAAGGGG
CCGAGTCAATCCGCCGAGTTGGGGCACGAAAAACAAAAAGGGAAGGCTACTAAGATTTTTCTGGCGGGGGTTATCATT
GGCGTAACTGCAGGGACCACCTCCCGGGTTGAGGGGGCTGGATCTCCAGGCTGCGGATTAAGCCCCTCCCGTCGGCG
TTAATTTCAAACTGCGCGACGTTTCTCACCTGCCTTCGCCAAGGCAGGGGCCGGGACCCTATTCAAGAGGTAGTAAC
TAGCAGGACTCTAGCCTTCCGCAATTCATTGAGCGCATTTACGGAAGTAACGTCGGGTACTGTCTCTGGCCGCAAGGG
TGGGAGGAGTACGCATTTGGCGTAAGGTGGGGCGTAGAGCCTTCCCGCCATTGGCGGCGATAGGGCGTTTACGCGA
CGGCCTGACGTAGCGGAAGACGCCTTAGTGGGGGGAAGGTTCTAGAAAAGCGGCGGCAGCGGCTCTAGCGGCAGT
AGCAGCAGCGCCGGGTCCCGTGCGGAGGTGCTCCTCGCAGAGTTGTTTCTCCAGCAGCGGCAGTTCTCACTACAGCG
CCAGGACGAGTCCGGTTCGTGTTCGTCCGCGGAGATCTCTCTCATCTCGCTCGGCTGCGGGAAATCGGGCTGAAGCG
ACTGAGTCCGCGATGGAGGTAACGGGTTTGAAATCAATGAGTTATTGAAAAGGGCATGGCGAGGCCGTTGGCGCCTC
AGTGGAAGTCGGCCAGCCGCCTCCGTGGGAGAGAGGCAGGAAATCGGACCAATTCAGTAGCAGTGGGGCTTAAGGTT
TATGAACGGGGTCTTGAGCGGAGGCCTGAGCGTACAAACAGCTTCCCCACCCTCAGCCTCCCGGCGCCATTTCCCTTC
```

SEQUENCE LISTING FREE TEXT

```
ACTGGGGGTGGGGGATGGGGAGCTTTCACATGGCGGACGCTGCCCCGCTGGGGTGAAAGTGGGGCGCGGAGGCGGG
ACTTCTTATTCCCTTTCTAAAGCACGCTGCTTCGGGGGCCACGGCGTCTCCTCGGAAAGCTT
```

Nucleotide sequence of antibody (OMLH) light chain gene cDNA to which an optimized Kozak has been added upstream of the initiation codon.
<SEQ ID NO: 4>

```
CGCGCCCCGCCGCCACCATGGGTTGGTCTTGTATCATCTTATTTTTAGTTGCTACTGCTACTGGTGTTCATTCTGATATA
CAGCTCACCCAAAGCCCATCATCTCTGTCTGCAAGCGTCGGCGACAGGGTGACCATTACCTGTCGCGCAAGCCAAAGC
GTTGACTACGACGGCGACAGCTACATGAACTGGTACCAGCAGAAGCCCGGCAAGGCTCCTAAGCTGCTGATCTATGCC
GCCTCCTACCTTGAATCTGGAGTGCCTTCTCGTTTTTCCGGCTCAGGGTCCGGAACTGATTTTACCCTGACCATTTCCT
CCCTCCAGCCCGAGGATTTTGCCACTTACTACTGTCAGCAGTCCCACGAGGACCCATATACATTCGGACAAGGTACAA
AGGTAGAAATCAAGCGTACGGTGGCTGCCCCATCCGTGTTCATATTTCCTCCTAGCGACGAACAACTCAAGTCCGGTA
CCGCCAGCGTGGTCTGCCTGTTGAACAATTTTTATCAAGAGAAGCTAAGGTCCAGTGGAAGGTTGACAACGCCCTTC
AGTCCGGAAATAGCCAAGAGAGCGTCACCGAACAGGACTCCAAGGACAGTACATACTCACTGAGCTCTACACTGACCC
TTTCTAAGGCCGACTACGAGAAGCACAAGGTCTACGCATGCGAAGTGACCCATCAGGGACTCAGTAGCCCTGTAACAA
AGAGTTTTAATCGAGGCGAGTGCTAAGCGAT
```

Nucleotide sequence of antibody (OMLH) heavy chain gene cDNA to which an optimized
Kozak has been added upstream of the initiation codon.
<SEQ ID NO: 5>

```
GGCCGCCCGCCGCCACCATGGAATTTGGTTTATCTTGGGTTTTTTTAGTTGCTTATTAAGAGGTGTTCAATGTGAGGT
GCAGTTGGTCGAATCCGGCGGCGGACTCGTGCAACCAGGCGGAACTTTGCGGCTGTCCTGCGCAGTGTCTGGTTACA
GCATCACCTCCGGGTATAGCTGGAACTGGATCCGCCAGGCTCCTGGAAAGGGGCTTGAGTGGGTGGCTTCCATTACCT
ACGACGGCTCCACTAACTATAACCCGAGCGTCAAAGGCAGAATCACCATCTCTCGGGACGACTCAAAGAATACCTTCT
ACCTGCAGATGAACTCACTGAGGGCCGAAGATACCGCAGTTTACTACTGCGCCAGGGGGTCCCACTATTTCGGCCACT
GGCACTTCGCCGTGTGGGGACAGGGCACACTCGTGACCGTTAGTAGCGCTAGCACCAAAGGCCCCTCTGTGTTCCCA
CTTGCTCCCTCCAGTAAATCTACCTCCGGAGGAACCGCAGCCCTCGGCTGCCTGGTGAAGGATTACTTCCCAGAGCCC
GTCACCGTCTCTTGGAACTCCGGAGCCTTGACTAGCGGAGTGCACACTTTCCCTGCTGTATTGCAGTCCAGCGGCTTG
TATTCACTGAGTAGCGTCGTCACCGTGCCTTCAAGCAGCCTCGGGACACAGACATACATATGTAATGTCAACCATAAGC
CATCAAACACTAAAGTTGATAAAAAGGTGGAACCTAAGAGTTGCGATAAGACCCATACCTGTCCTCCTTGCCCTGCTCC
TGAGCTGCTGGGAGGCCCTAGCGTGTTTCTGTTCCCCCCCAAGCCCAAAGATACACTGATGATTTCCCGCACACCTGA
AGTAACATGTGTCGTGGTTGATGTGAGTCACGAGGATCCAGAGGTCAAGTTTAATTGGTACGtGGACGGAGTGGAGGT
GCACAACGCTAAGACTAAGCCTCGGGAGGAACAGTACAACAGCACATACCGCGTGGTCAGCGTTTTGACTGTGCTGC
ATCAAGACTGGCTCAATGGAAAGGAATACAAGTGCAAGGTCTCTAATAAAGCCCTCCCCGCTCCTATTGAGAAGACTAT
TTCTAAAGCCAAGGGCCAGCCTCGCGAACCTCAGGTATATACTTTGCCACCAAGAGACACTGATGATTTCCCGCAACCTGA
GGTCTCACTCACTTGCCTCGTCAAAGGGTTTTACCCTTCTGACATCGCTGTCGAATGGGAAAGTAATGGTCAGCAGA
AAACAATTACAAGACTACTCCACCAGTGCTCGATTCTGATGGAAGTTTCTTTCTCTACAGTAAGCTCACTGTGGACAAA
TCTCGCTGGCAGCAGGGTAACGTATTCTCATGCTCCGTGATGCATGAAGCCCTCCACAACCATTACACCCAGAAGAGC
CTGTCTCTGAGCCCAGGCAAGTAACCTGCA
```

Entire sequence of pDC61.
<SEQ ID NO: 6>

```
CGATGTACGGGCCAGATATACGCGTTGACATTGATTATTGACTAGTTATTAATAGTAATCAATTACGGGGTCATTAGTTC
ATAGCCCATATATGGAGTTCCGCGTTACATAACTTACGGTAAATGGCCCGCCTGGCTGACCGCCCAACGACCCCCGCC
CATTGACGTCAATAATGACGTATGTTCCCATAGTAACGCCAATAGGGACTTTCCATTGACGTCAATGGGTGGAGTATTT
ACGGTAAACTGCCCACTTGGCAGTACATCAAGTGTATCATATGCCAAGTACGCCCCCTATTGACGTCAATGACGGTAAA
TGGCCCGCCTGGCATTATGCCCAGTACATGACCTTATGGGACTTTCCTACTTGGCAGTACATCTACGTATTAGTCATCG
CTATTACCATGGTGATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATGTCGTAACAACTCCG
CCCCATTGACGCAAATGGGCGGTAGGCGTGTACGGTGGGAGGTCTATATAAGCAGAGCTCTCTGGCTAACTAGAGAAC
CCACTGTTAACTGGCTTATCGAAATTGTCGAGGAGAACTTCAGGGTGAGTTTGGGGACCCTTGATTGTTCTTTCTTTTT
CGCTATTGTAAAATTCATGTTATATGGAGGGGGCAAAGTTTTCAGGGTGTTGTTTAGAATGGGAAGATGTCCCTTGTAT
CACCATGGACCCTCATGATAATTTGTTTCTTTCACTTTCTACTCTGTTGACAACCAT-
TGTCTCCTCTTATTTTCTTTTCA
TTTTCTGTAACTTTTTCGTTAAACTTTAGCTTGCATTTGTAACGAATTTTTAAATT-
CACTTTTGTTTATTTGTCAGATTGT
AAGTACTTTCTCTAATCACTTTTTTTTCAAGGCAATCAGGGTATATTATATTGTACTTCAGCACAGTTTTAGAGAACAAT
TGTTATAATTAAATGATAAGGTAGAATATTTCTGCATATAAATTCTGGCTGGCGTGGAAATATTCTTATTGGTAGAAACA
ACTACATCCTGGTCATCATCCTGCCTTTCTCTTTATGGTTACAATGATATACACTGTTTGAGATGAGGATAAAATACTCT
GAGTCCAAACCGGGCCCCTCTGCTAACCATGTTCATGCCTTCTTCTTTTTCCTACAGCTCCTGGGCAACGTGCTGGCC
GCCGCCCCGGGGCCTCGACTGTGCCTTCTAGTTGCCAGCCATCTGTTGTTTGCCCCTCCCCCGTGCCTTCCTTGACCC
TGGAAGGTGCCACTCCCACTGTCCTTTCCTAATAAAATGAGGAAATTGCATCGCATTGTCTGAGTAGGTGTCATTCTAT
TCTGGGGGGTGGGGTGGGGCAGGACAGCAAGGGGGAGGATTGGGAAGACAATAGCAGGCATGCTGGGGACTCGAGC
GATGTACGGGCCAGATATACGCGTTGACATTGATTATTGACTAGTTATTAATAGTAATCAATTACGGGGTCATTAGTTCA
TAGCCCATATATGGAGTTCCGCGTTACATAACTTACGGTAAATGGCCCGCCTGGCTGACCGCCCAACGACCCCCGCC
ATTGACGTCAATAATGACGTATGTTCCCATAGTAACGCCAATAGGGACTTTCCATTGACGTCAATGGGTGGAGTATTTA
CGGTAAACTGCCCACTTGGCAGTACATCAAGTGTATCATATGCCAAGTACGCCCCCTATTGACGTCAATGACGGTAAAT
GGCCCGCCTGGCATTATGCCCAGTACATGACCTTATGGGACTTTCCTACTTGGCAGTACATCTACGTATTAGTCATCGC
TATTACCATGGTGATGCGGTTTTGGCAGTACATCAATGGGCGTGGATAGCGGTTTGACTCACGGGGATTTCCAAGTCT
CCACCCCATTGACGTCAATGGGAGTTTGTTTTGGCACCAAAATCAACGGGACTTTCCAAAATGTCGTAACAACTCCGC
CCCATTGACGCAAATGGGCGGTAGGCGTGTACGGTGGGAGGTCTATATAAGCAGAGCTCTCTGGCTAACTAGAGAACC
CACTGTTAACTGGCTTATCGAAATTGTCGAGGAGAACTTCAGGGTGAGTTTGGGGACCCTTGATTGTTCTTTCTTTTTC
GCTATTGTAAAATTCATGTTATATGGAGGGGGCAAAGTTTTCAGGGTGTTGTTTAGAATGGGAAGATGTCCCTTGTATC
ACCATGGACCCTCATGATAATTTGTTTCTTTCACTTTCTACTCTGTTGACAACCAT-
TGTCTCCTCTTATTTTCTTTTCAT
TTTCTGTAACTTTTTCGTTAAACTTTAGCTTGCATTTGTAACGAATTTTTAAATT-
CACTTTTGTTTATTTGTCAGATTGTA
```

```
AGTACTTTCTCTAATCACTTTTTTTTCAAGGCAATCAGGGTATATTATATTGTACTTCAGCACAGTTTTAGAGAACAATT
GTTATAATTAAATGATAAGGTAGAATATTTCTGCATATAAATTCTGGCTGGCGTGGAAATATTCTTATTGGTAGAAACAA
CTACATCCTGGTCATCATCCTGCCTTTCTCTTTATGGTTACAATGATATACACTGTTTGAGATGAGGATAAAATACTCTG
AGTCCAAACCGGGCCCCTCTGCTAACCATGTTCATGCCTTCTTCTTTTTCCTACAGCTCCTGGGCAACGTGCTGGCGC
GCCTCTAGAGCCTCGACTGTGCCTTCAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGTCTGAGTAGGTGTCATTCTATTC
TGGGGGGTGGGGTGGGGCAGGACAGCAAGGGGGAGGATTGGGAAGACAATAGCAGGCATGCTGGGGAGGATCTCCG
CGGTGTGGAATGTGTGTCAGTTAGGGTGTGGAAAGTCCCCAGGCTCCCCAGCAGGCAGAAGTATGCAAAGCATGCAT
CTCAATTAGTCAGCAACCATAGTCCCGCCCCTAACTCCGCCCATCCCGCCCCTAACTCCGCCCAGTTCCGCCCATTCTC
CGCCCCATGGCTGACTAATTTTTTTATTTATGCAGAGGCCGAGGCCGCCTCGGCCTCTGAGCTATTCCAGAAGTAGTG
AGGAGGCTTTTTGGAGGCCTAGGCTTTTGCAAAAAAGCTGCAGATGGTACGACCATTAAATTGTATTGTAGCAGTATC
ACAAAATATGGGTATTGGTAAAAATGGTGATTTACCATGGCCACCATTACGAAATGAATTTAAATATTTTCAACGAATGA
CTACTACTTCATCAGTAGAAGGTAAACAAAATTTAGTAATTATGGGTCGAAAAACTTGGTTTTCAATTCCTGAGAAGAA
TCGACCTTTAAAGGACAGAATTAATATAGTTCTCAGTAGAGAACTCAAAGAACCACCACGAGGAGCTCATTTTCTTGCC
AAAAGTTTGGATGATGCCTTAAGACTTATTGAACAACCGGAATTGGCAAGTAAAGTAGACATGGTTTGGATAGTCGGA
GGCAGTTCTGTTTACCAGGAAGCCATGAATCAACCAGGCCACCTCAGACTCTTTGTGACAAGGATCATGCAGGAATTT
GAAAGTGACACGTTTTTCCCAGAAATTGATTTGGGGAAATATAAACTTCTCCCAGAATACCCAGGCGTCCTCTCTGAGG
TCCAGGAGGAAAAAGGCATCAAGTATAAGTTTGAAGTCTACGAGAAGAAAGACTAAAGATCCGTGACATAATTGGACA
AACTACCTACAGAGATTTAAAGCTCTAAGGTAAATATAAAATTTT-
TAAGTGTATAATGTGTTAAACTACTGATTCTAATTG
TTTGTGTATTTTAGATTCCAACCTATGGAACTGATGAATGGGAGCAGTGGTGGAATGCCTTTAATGAGGAAAACCTGTT
TTGCTCAGAAGAAATGCCATCTAGTGATGATGAGGCTACTGCTGACTCTCAACATTCTACTCCTCCAAAAAGAAGAGA
AAGGTAGAAGACCCCAAGGACTTTCCTTCAGAATTGCTAAGTTTTTTGAGTCATGCTGTGTTTAGTAATAGAACTCTTG
CTTGCTTTGCTATTTACACCACAAAGGAAAAAGCTGCACTGCTATACAAGAAAATTATGGAAAAATATTCTGTAACCTTT
ATAAGTAGGCATAACAGTTATAATCATAACATACTGTTTTTCTTACTCCACACAGGCATAGAGTGTCTGCTATTAATAA
CTATGCTCAAAAATTGTGTACCTTTAGCTTTTTAATTTGTAAAGGGGTTAATAAGGAATATTTGATGTATAGTGCCTTGA
CTAGAGATCATAATCAGCCATACCACATTTGTAGAGGTTTTACTTGCTTTAAAAAACCTCCCACACCTCCCCCTGAACC
TGAAACATAAAATGAATGCAATTGTTGTTAACTTGTTTATTGCAGCTTATAATGGTTACAAATAAAGCAATAGCATC
ACAAATTTCACAAATAAAGCATTTTTTTCACTGCATTCTAGTTGTGGTTTGTCCAAACTCATCAATGTATCTTATCATGT
CTGGGCCCATCGATGAATTCACTGGCCGTCGTTTTACAACGTCGTGACTGGGAAAACCCTGGCGTTACCCAACTTAAT
CGCCTTGCAGCACATCCCCCTTTCGCCAGCTGGCGTAATAGCGAAGAGGCCCGCACCGATCGCCCTTCCCAACAGTTG
CGCAGCCTGAATGGCGAATGGCGCCTGATGCGGTATTTTCTCCTTACGCATCTGTGCGGTATTTCACACCGCATATGGT
GCACTCTCAGTACAATCTGCTCTGATGCCGCATAGTTAAGCCAGCCCCGACACCCGCCAACACCCGCTGACGCGCCCT
GACGGGCTTGTCTGCTCCCGGCATCCGCTTACAGACAAGCTGTGACCGTCTCCGGGAGCTGCATGTGTCAGAGGTTTT
CACCGTCATCACCGAAACGCGCGAGACGAAAGGGCCTCGTGATACGCCTATTTTTATAGGTTAATGTCATGATAATAAT
GGTTTCTTAGACGTCAGGTGGCACTTTTCGGGGAAATGTGCGCGGAACCCCTATTTGTTTATTTTTCTAAATACATTCA
AATATGTATCCGCTCATGAGACAATAACCCTGATAAATGCTTCAATAATATTGAAAAAGGAAGAGTATGAGTATTCAACA
TTTCCGTGTCGCCCTTATTCCCTTTTTTGCGGCATTTTGCCTTCCTGTTTTTGCTCACCCAGAAACGCTGGTGAAAGTA
AAAGATGCTGAAGATCAGTTGGGTGCACGAGTGGGTTACATCGAACTGGATCTCAACAGCGGTAAGATCCTTGAGAGT
TTTCGCCCCGAAGAACGTTTTCCAATGATGAGCACTTTTAAAGTTCTGCTATGTGGCGCGGTATTATCCCGTATTGACG
CCGGGCAAGAGCAACTCGGTCGCCGCATACACTATTCTCAGAATGACTTGGTTGAGTACTCACCAGTCACAGAAAAGC
ATCTTACGGATGGCATGACAGTAAGAGAATTATGCAGTGCTGCCATAACCATGAGTGATAACACTGCGGCCAACTTACT
TCTGACAACGATCGGAGGACCGAAGGAGCTAACCGCTTTTTTGCACAACATGGGGGATCATGTAACTCGCCTTGATCG
TTGGGAACCGGAGCTGAATGAAGCCATACCAAACGACGAGCGTGACACCACGATGCCTGTAGCAATGGCAACAACGT
TGCGCAAACTATTAACTGGCGAACTACTTACTCTAGCTTCCCGGCAACAATTAATAGACTGGATGGAGGCGGATAAAGT
TGCAGGACCACTTCTGCGCTCGGCCCTTCCGGCTGGCTGGTTTATTGCTGATAAATCTGGAGCCGGTGAGCGTGGGTC
TCGCGGTATCATTGCAGCACTGGGGCCAGATGGTAAGCCCTCCCGTATCGTAGTTATCTACACGACGGGGAGTCAGGC
AACTATGGATGAACGAAATAGACAGATCGCTGAGATAGGTGCCTCACTGATTAAGCATTGGTAACTGTCAGACCAAGTT
TACTCATATATACTTTAGATTGATTTAAAACTTCATTTTTAATTTAAAAGGATCAGGT-
GAAGATCCTTTTTGATAATCTC
ATGACCAAAATCCCTTAACGTGAGTTTTCGTTCCACTGAGCGTCAGACCCCGTAGAAAAGATCAAAGGATCTTCTTGA
GATCCTTTTTTTCTGCGCGTAATCTGCTGCTTGCAAACAAAAAAACCACCGCTACCAGCGGTGGTTTGTTTGCCGGATC
AAGAGCTACCAACTCTTTTTCCGAAGGTAACTGGCTTCAGCAGAGCGCAGATACCAAATACTGTTCTTCTAGTGTAGCC
GTAGTTAGGCCACCACTTCAAGAACTCTGTAGCACCGCCTACATACCTCGCTCTGCTAATCCTGTTACCAGTGGCTGCT
GCCAGTGGCGATAAGTCGTGTCTTACCGGGTTGGACTCAAGACGATAGTTACCGGATAAGGCGCAGCGGTCGGGCTG
AACGGGGGGTTCGTGCACACAGCCCAGCTTGGAGCGAACGACCTACACCGAACTGAGATACCTACAGCGTGAGCTAT
GAGAAAGCGCCACGCTTCCCGAAGGGAGAAAGGCGGACAGGTATCCGGTAAGCGGCAGGGTCGGAACAGGAGAGCG
CACGAGGGAGCTTCCAGGGGGAAACGCCTGGTATCTTTATAGTCCTGTCGGGTTTCGCCACCTCTGACTTGAGCGTCG
ATTTTTGTGATGCTCGTCAGGGGGCGGAGCCTATGGAAAAACGCCAGCAACGCGGCCTTTTTACGGTTCCTGGCCTT
TTGCTGGCCTTTTGCTCACATGTTCTTTCCTGCGTTATCCCCTGATTCTGTGGATAACCGTATTACCGCCTTTGAGTGA
GCTGATACCGCTCGCCGCAGCCGAACGACCGAGCGCAGCGAGTCAGTGAGCGAGGAAGCGGAAGAGCGCCCAATAC
GCAAACCGCCTCTCCCCGCGCGTTGGCCGATTCATTAATGCAGCTGGCACGACAGGTTTCCCGACTGGAAAGCGGGC
AGTGAGCGCAACGCAATTAATGTGAGTTAGCTCACTCATTAGGCACCCCAGGCTTTACACTTTATGCTTCCGGCTCGTA
TGTTGTGTGGAATTGTGAGCGGATAACAATTTCACACAGGAAACAGCTATGACCATGATTACGCCAAGCTT

A sequence that replaced a sequence within pDC6 (pDC61).
                                                                <SEQ ID NO: 7>
AATTCACTGGCCGTCGTTTTACAACGTCGTGACTGGGAAAACCCTGGCGTTACCCAACTTAATCGCCTTGCAGCACAT
CCCCCTTTCGCCAGCTGGCGTAATAGCGAAGAGGCCCGCACCGATCGCCCTTCCCAACAGTTGCGCAGCCTGAATGG
CGAATGGCGCCTGATGCGGTATTTTCTCCTTACGCATCTGTGCGGTATTTCACACCGCATATGGTGCACTCTCAGTACA
ATCTGCTCTGATGCCGCATAGTTAAGCCAGCCCCGACACCCGCCAACACCCGCTGACGCGCCCTGACGGGCTTGTCTG
CTCCCGGCATCCGCTTACAGACAAGCTGTGACCGTCTCCGGGAGCTGCATGTGTCAGAGGTTTTCACCGTCATCACCG
AAACGCGCGAGACGAAAGGGCCTCGTGATACGCCTATTTTTATAGGTTAATGTCATGATAATAATGGTTTCTTAGACGT
CAGGTGGCACTTTTCGGGGAAATGTGCGCGGAACCCCTATTTGTTTATTTTTCTAAATACATTCAAATATGTATCCGCTC
ATGAGACAATAACCCTGATAAATGCTTCAATAATATTGAAAAGGAAGAGTATGAGTATTCAACATTTCCGTGTCGCCC
TTATTCCCTTTTTTGCGGCATTTTGCCTTCCTGTTTTTGCTCACCCAGAAACGCTGGTGAAAGTAAAAGATGCTGAAGA
TCAGTTGGGTGCACGAGTGGGTTACATCGAACTGGATCTCAACAGCGGTAAGATCCTTGAGAGTTTTCGCCCCGAAGA
ACGTTTTCCAATGATGAGCACTTTTAAAGTTCTGCTATGTGGCGCGGTATTATCCCGTATTGACGCCGGGCAAGAGCAA
```

CTCGGTCGCCGCATACACTATTCTCAGAATGACTTGGTTGAGTACTCACCAGTCACAGAAAAGCATCTTACGGATGGC
ATGACAGTAAGAGAATTATGCAGTGCTGCCATAACCATGAGTGATAACACTGCGGCCAACTTACTTCTGACAACGATCG
GAGGACCGAAGGAGCTAACCGCTTTTTTGCACAACATGGGGAGTCATGTAACTCGCCTTGATCGTTGGGAACCGGAGC
TGAATGAAGCCATACCAAACGACGAGCGTGACACCACGATGCCTGTAGCAATGGCAACAACGTTGCGCAAACTATTAA
CTGGCGAACTACTTACTCTAGCTTCCCGGCAACAATTAATAGACTGGATGGAGGCGGATAAAGTTGCAGGACCACTTC
TGCGCTCGGCCCTTCCGGCTGGCTGGTTTATTGCTGATAAATCTGGAGCCGGTGAGCGTGGGTCTCGCGGTATCATTG
CAGCACTGGGGCCAGATGGTAAGCCCTCCCGTATCGTAGTTATCTACACGACGGGGAGTCAGGCAACTATGGATGAAC
GAAATAGACAGATCGCTGAGATAGGTGCCTCACTGATTAAGCATTGGTAACTGTCAGACCAAGTTTACTCATATATACT
TTAGATTGATTTAAAACTTCATTTTTAATTTAAAAGGATCTAGGTGAAGATCCTTTTTGATAATCTCATGACCAAAATCC
CTTAACGTGAGTTTTCGTTCCACTGAGCGTCAGACCCCGTAGAAAAGATCAAAGGATCTTCTTGAGATCCTTTTTTTCT
GCGCGTAATCTGCTGCTTGCAAACAAAAAAACCACCGCTACCAGCGGTGGTTTGTTTGCCGGATCAAGAGCTACCAAC
TCTTTTTCCGAAGGTAACTGGCTTCAGCAGAGCGCAGATACCAAATACTGTTCTTCTAGTGTAGCCGTAGTTAGGCCAC
CACTTCAAGAACTCTGTAGCACCGCCTACATACCTCGCTCTGCTAATCCTGTTACCAGTGGCTGCTGCCAGTGGCGATA
AGTCGTGTCTTACCGGGTTGGACTCAAGACGATAGTTACCGGATAAGGCGCAGCGGTCGGGCTGAACGGGGGGTTCG
TGCACACAGCCCAGCTTGGAGCGAACGACCTACACCGAACTGAGATACCTACAGCGTGAGCTATGAGAAAGCGCCAC
GCTTCCCGAAGGGAGAAAGGCGGACAGGTATCCGGTAAGCGGCAGGGTCGGAACAGGAGAGCGCACGAGGGAGCTT
CCAGGGGGAAACGCCTGGTATCTTTATAGTCCTGTCGGGTTTCGCCACCTCTGACTTGAGCGTCGATTTTTGTGATGC
TCGTCAGGGGGGCGGAGCCTATGGAAAAACGCCAGCAACGCGGCCTTTTTACGGTTCCTGGCCTTTTGCTGGCCTTTT
GCTCACATGTTCTTTCCTGCGTTATCCCCTGATTCTGTGGATAACCGTATTACCGCCTTTGAGTGAGCTGATACCGCTC
GCCGCAGCCGAACGACCGAGCGCAGCGAGTCAGTGAGCGAGGAAGCGGAAGAGCGCCCAATACGCAAACCGCCTCT
CCCCGCGCGTTGGCCGATTCATTAATGCAGCTGGCACGACAGGTTTCCCGACTGGAAAGCGGGCAGTGAGCGCAACG
CAATTAATGTGAGTTAGCTCACTCATTAGGCACCCCAGGCTTTACACTTTATGCTTCCGGCTCGTATGTTGTGTGGAAT
TGTGAGCGGATAACAATTTCACACAGGAAACAGCTATGACCATGATTACGCCA cDNA encoding human omalizumab (OMLH) light chain that replaced the nucleotide
sequences No. 1267 to No. 1273 of pDC61.
                                                                    <SEQ ID NO: 8>
GGCCGCCACCATGGGTTGGTCTTGTATCATCTTATTTTTAGTTGCTACTGCTACTGGTGTTCATTCTGATATACAGCTCA
CCCAAAGCCCATCATCTCTGTCTGCAAGCGTCGGCGACAGGGTGACCATTACCTGTCGCGCAAGCCAAAGCGTTGACT
ACGACGGCGACAGCTACATGAACTGGTACCAGCAGAAGCCCGGCAAGGCTCCTAAGCTGCTGATCTATGCCGCCTCCT
ACCTTGAATCTGGAGTGCCTTCTCGTTTTTCCGGCTCAGGGTCCGGAACTGATTTTACCCTGACCATTTCCTCCCTCCA
GCCCGAGGATTTTGCCACTTACTACTGTCAGCAGTCCCACGAGGACCCATATACATTCGGACAAGGTACAAAGGTAGA
AATCAAGCGTACGGTGGCTGCCCCATCCGTGTTCATATTTCCTCCTAGCGACGAACAACTCAAGTCCGGTACCGCCAG
CGTGGTCTGCCTGTTGAACAATTTTTATCAAGAGAAGCTAAGGTCCAGTGGAAGGTTGACAACGCCCTTCAGTCCGG
AAATAGCCAAGAGAGCGTCACCGAACAGGACTCCAAGGACAGTACATACTCACTGAGCTCTACACTGACCCTTTCTAA
GGCCGACTACGAGAAGCACAAGGTCTACGCATGCGAAGTGACCCATCAGGGACTCAGTAGCCCTGTAACAAAGAGTT
TTAATCGAGGCGAGTGCTAAC cDNA encoding human omalizumab (OMLH) heavy chain that replaced the nucleotide
sequences No. 2765 to No. 2771 of pDC61.
                                                                    <SEQ ID NO: 9>
CGCGCCACCATGGAATTTGGTTTATCTTGGGTTTTTTTAGTTGCTTTATTAAGAGGTGTTCAATGTGAGGTGCAGTTGG
TCGAATCCGGCGGCGGACTCGTGCAACCAGGCGGAAGTTTGCGGCTGTCCTGCGCAGTGTCTGGTTACAGCATCACC
TCCGGGTATAGCTGGAACTGGATCCGCCAGGCTCCTGGAAAGGGGCTTGAGTGGGTGGCTTCCATTACCTACGACGG
CTCCACTAACTATAACCCGAGCGTCAAAGGCAGAATCACCATCTCTCAAGACACCTCAAAGAATACCTTCTACCTGCA
GATGAACTCACTGAGGGCCGAAGATACCGCAGTTTACTACTGCGCCAGGGGGTCCCACTATTTCGGCCACTGGCACTT
CGCCGTGTGGGGACAGGGCACACTCGTGACCGTTAGTAGCGCTAGCACCAAAGGCCCCTCTGTGTTCCCACTTGCTC
CCTCCAGTAAATCTACCTCCGGAGGAACCGCAGCCCTCGGCTGCCTGGTGAAGGATTACTTCCCAGAGCCCGTCACCG
TCTCTTGGAACTCCGGAGCCTTGACTAGCGGAGTGCACACTTTCCCTGCTGTATTGCAGTCCAGCGGCTTGTATTCAC
TGAGTAGCGTCGTCACCGTGCCCTTCAAGCAGCCTCGGGACACAGACATACATATGTAATGTCAACCATAAGCCATCAA
ACACTAAAGTTGATAAAAAGGTGGAACCTAAGAGTTGCGATAAGACCCATACCTGTCCTCCTTGCCCTGCTCCTGAGC
TGCTGGGAGGCCCTAGCGTGTTTCTGTTCCCCCCCAAGCCCAAAGATACACTGATGATTTCCCGCACACCTGAAGTAA
CATGTGTCGTGGTTGATGTGAGTCACGAGGATCCAGAGGTCAAGTTTAATTGGTACGtGGACGGAGTGGAGGTGCACA
ACGCTAAGACTAAGCCTCGGGAGGAACAGTACAACAGCACATACCGCGTGGTCAGCGTTTTGACTGTGCTGCATCAAG
ACTGGCTCAATGGAAAGGAATACAAGTGCAAGGTCTCTAATAAAGCCCTCCCCGCTCCTATTGAGAAGACTATTTCTAA
AGCCAAGGGCCAGCCTCGCGAACCTCAGGTATATACTTTGCCACCCTCTCGCGAAGAAATGACAAAGAATCAGGTCTC
ACTCACTTGCCTCGTCAAAGGGTTTTACCCTTCTGACATCGCTGTCGAATGGGAAAGTAATGGTCAGCCAGAAAACAA
TTACAAGACTACTCCACCAGTGCTCGATTCTGATGGAAGTTTCTTTCTCTACAGTAAGCTCACTGTGGACAAATCTCGC
TGGCAGCAGGGTAACGTATTCTCATGCTCCGTGATGCATGAAGCCCTCCACAACATTACACCCAGAAGAGCCTGTCT
CTGAGCCCAGGCAAGTAAT Entire nucleotide sequence of backbone vector pNC32c-U533.
                                                                   <SEQ ID NO: 10>
CGATGTACGGGCCAGATATACGCGTTGACATTGATTATTGACTAGTTATTAATAGTAATCAATTACGGGGTCATTAGTTC
ATAGCCCATATATGGAGTTCCGCGTTACATAACTTACGGTAAATGGCCCGCCTGGCTGACCGCCCAACGACCCCCGCC
CATTGACGTCAATAATGACGTATGTTCCCATAGTAACGCCAATAGGGACTTTCCATTGACGTCAATGGGTGGAGTATTT
ACGGTAAACTGCCCACTTGGCAGTACATCAAGTGTATCATATGCCAAGTACGCCCCCTATTGACGTCAATGACGGTAAA
TGGCCCGCCTGGCATTATGCCCAGTACATGACCTTATGGGACTTTCCTACTTGGCAGTACATCTACGTATTAGTCATCG
CTATTACCATGGTGATGCGGTTTTGGCAGTACATCAATGGGCGTGGATAGCGGTTTGACTCACGGGGATTTCCAAGTC
TCCACCCCATTGACGTCAATGGGAGTTTGTTTTGGCACCAAAATCAACGGGACTTTCCAAAATGTCGTAACAACTCCG
CCCCATTGACGCAAATGGGCGGTAGGCGTGTACGGTGGGAGGTCTATATAAGCAGAGCTCTCTGGCTAACTAGAGAAC
CCACTGTTAACTGGCTTATCGAAATTGGCGCGCCGCGATCGCCCTCCCACACCTCCCCCTGAACCTGAAACATAAAAT
GAATGCAATTGTTGTTGTTAACTTGTTTATTGCAGCTTATAATGGTTACAAATAAAGCAATAGCATCACAAATTTCACAA
ATAAAGCATTTTTTTCACTGCATTCTAGTTGTGGTTTGTCCAAACTCATCAATGTATCTTATCATGTCTGGATCTCCGCG
GCCCTCCGCGCCTACAGCTCAAGCCACATCCGAAGGGGAGGGAGCCGGGAGCTGCGCGCGGGGCCGCCGGGGGA
GGGGTGGCACCGCCCACGCCGGGCGGCCACGAAGGGCGGGGCAGCGGGCGCGCGCGGCGGGGGAGGGCCG
GCGCCGCGCCCGCTGGGAATTGGGGCCCTAGGGGGAGGGCGGAGGCGCCGACGACCGCGGCACTTACCGTTCGCGG

| SEQUENCE LISTING FREE TEXT |
|---|
| CGTGGCGCCCGGTGGTCCCCAAGGGGAGGGAAGGGGGAGGCGGGGCGAGGACAGTGACCGGAGTCTCCTCAGCGG |
| TGGCTTTTCTGCTTGGCAGCCTCAGCGGCTGGCGCCAAAACCGGACTCCGCCCACTTCCTCGCCCGCCGGTGCGAGG |
| GTGTGGAATCCTCCAGACGCTGGGGGAGGGGGAGTTGGGAGCTTAAAAACTAGTACCCCTTTGGGACCACTTTCAGC |
| AGCGAACTCTCCTGTACACCAGGGGTCAGTTCCACAGACGCGGGCCAGGGGTGGGTCATTGCGGCGTGAACAATAAT |
| TTGACTAGAAGTTGATTCGGGTGTTTCCGGAAGGGGCCGAGTCAATCCGCCGAGTTGGGGCACGGAAAACAAAAAGG |
| GAAGGCTACTAAGATTTTTCTGGCGGGGGTTATCATTGGCGTAACTGCAGGGACCACCTCCCGGGTTGAGGGGGCTG |
| GATCTCCAGGCTGCGGATTAAGCCCCTCCCGTCGGCGTTAATTTCAAACTGCGCGACGTTTCTCACCTGCCTTCGCCA |
| AGGCAGGGGCCGGGACCCTATTCCAAGAGGTAGTAACTAGCAGGACTCTAGCCTTCCGCAATTCATTGAGCGCATTTA |
| CGGAAGTAACGTCGGGTACTGTCTCTGGCCGCAAGGGTGGGAGGAGTACGCATTTGGCGTAAGGTGGGGCGTAGAGC |
| CTTCCCGCCATTGGCGGCGGATAGGGCGTTTACGCGACGGCCTGACGTAGCGGAAGACGCCTTAGTGGGGGGAAGG |
| TTCTAGAAAAGCGGCGGCAGCGGCTCTAGCGGCAGTAGCAGCAGCGCCGGGTCCCGTGCGGAGGTGCTCCTCGCAG |
| AGTTGTTTCTCCAGCAGCGGCAGTTCTCACTACAGCGCCAGGACGAGTCCGGTTCGTGTTCGTCCGGGAGATCTCTC |
| TCATCTCGCTCGGCTGCGGGAAATCGGGCTGAAGCGACTGAGTCCGCGATGGAGGTAACGGGTTTGAAATCAATGAG |
| TTATTGAAAAGGGCATGGCGAGGCCGTTGGCGCCTCAGTGGAAGTCGGCCAGCCGCCTCCGTGGGAGAGAGGCAGG |
| AAATCGGACCAATTCAGTAGCAGTGGGGCTTAAGGTTTATGAACGGGGTCTTGAGCGGAGGCCTGAGCGTACAAACA |
| GCTTCCCCACCCTCAGCCTCCCGGCGCCATTTCCCTTCACTGGGGGTGGGGGATGGGGAGCTTTCACATGGCGGACG |
| CTGCCCCGCTGGGGTGAAAGTGGGGCGCGGAGGCGGGACTTCTTATTCCCTTTCTAAAGCACGCTGCTTCGGGGGCC |
| ACGGCGTCTCCTCGGAGAATTCCGATGTACGGGCCAGATATACGCGTTGACATTGATTATTGACTAGTTATTAATAGTA |
| ATCAATTACGGGGTCATTAGTTCATAGCCCATATATGGAGTTCCGCGTTACATAACTTACGGTAAATGGCCCGCCTGGC |
| TGACCGCCCAACGACCCCCGCCCATTGACGTCAATAATGACGTATGTTCCCATAGTAACGCCAATAGGGACTTTCCATT |
| GACGTCAATGGGTGGAGTATTTACGGTAAACTGCCCACTTGGCAGTACATCAAGTGTATCATATGCCAAGTACGCCCC |
| TATTGACGTCAATGACGGTAAATGGCCCGCCTGGCATTATGCCCAGTACATGACCTTATGGGACTTTCCTACTTGGCAG |
| TACATCTACGTATTAGTCATCGCTATTACCATGGTGATGCGGTTTTGGCAGTACATCAATGGGCGTGGATAGCGGTTTG |
| ACTCACGGGGATTTCCAAGTCTCCACCCCATTGACGTCAATGGGAGTTTGTTTTGGCACCAAAATCAACGGGACTTTC |
| CAAAATGTCGTAACAACTCCGCCCCATTGACGCAAATGGGCGGTAGGCGTGTACGGTGGGAGGTCTATATAAGCAGAG |
| CTCTCTGGCTAACTAGAGAACCCACTGTTAACTGGCTTATCGAAATTGCGGCCGCCCTGCAGGCCTCCCACACCTCCC |
| CCTGAACCTGAAACATAAAATGAATGCAATTGTTGTTGTTAACTTGTTTATTGCAGCTTATAATGGTTACAAATAAAGCA |
| ATAGCATCACAAATTTCACAAATAAAGCATTTTTTCACTGCATTCTAGTTGTGGTTTGTCCAAACTCATCAATGTATCT |
| TATCATGTCTGGACTCCGCGGGCCCTCCGCGCCTACAGCTCAAGCCACATCCGAAGGGGGAGGGAGCCGGGAGCTG |
| CGCGCGGGGCCGCGGGGGAGGGTGGCACCGCCCACGCCGGGCGGCCACGAAGGGCGGGCAGCGGGCGCGCG |
| CGCGGCGGGGGAGGGGCCGGCGCCGCGCCCGCTGGGAATTGGGGCCCTAGGGGGAGGGCGGAGGCGCCGACGAC |
| CGCGGCACTTACCGTTCGCGGCGTGGCGCCCGGTGGTCCCCAAGGGGAGGGAAGGGGGAGGCGGGCGAGGACAG |
| TGACCGGAGTCTCCTCAGCGGTGGCTTTTCTGCTTGGCAGCCTCAGCGGCTGGCGCCAAAACCGGACTCCGCCCACT |
| TCCTCGCCCGCCGGTGCGAGGGTGTGGAATCCTCCAGACGCTGGGGGAGGGGGAGTTGGGAGCTTAAAAACTAGTAC |
| CCCTTTGGGACCACTTTCAGCAGCGAACTCTCCTGTACACCAGGGGTCAGTTCCACAGACGCGGGCCAGGGGTGGGT |
| CATTGCGGCGTGAACAATAATTTGACTAGAAGTTGATTCGGGTGTTTCCGGAAGGGGCCGAGTCAATCCGCCGAGTTG |
| GGGCACGGAAAACAAAAAGGGAAGGCTACTAAGATTTTTCTGGCGGGGTTATCATTGGCGTAACTGCAGGGACCAC |
| CTCCCGGGTTGAGGGGGCTGGATCTCCAGGCTGCGGATTAAGCCCCTCCCGTCGGCGTTAATTTCAAACTGCGCGAC |
| GTTTCTCACCTGCCTTCGCCAAGGCAGGGGCCGGGACCCTATTCCAAGAGGTAGTAACTAGCAGGACTCTAGCCTTCC |
| GCAATTCATTGAGCGCATTTACGGAAGTAACGTCGGGTACTGTCTCTGGCCGCAAGGGTGGGAGGAGTACGCATTTGG |
| CGTAAGGTGGGGCGTAGAGCCTTCCCGCCATTGGCGGCGGATAGGGCGTTTACGCGACGGCCTGACGTAGCGGAAGA |
| CGCCTTAGTGGGGGGAAGGTTCTAGAAAAGCGGCGGCAGCGGCTCTAGCGGCAGTAGCAGCAGCGCCGGGTCCCG |
| TGCGGAGGTGCTCCTCGCAGAGTTGTTTCTCCAGCAGCGGCAGTTCTCACTACAGCGCCAGGACGAGTCCGGTTCGT |
| GTTCGTCCGCGAGATCTCTCTCATCTCGCTCGGCTGCGGGAAATCGGGCTGAAGCGACTGAGTCCGCGATGGAGGT |
| AACGGGTTTGAAATCAATGAGTTATTGAAAAGGGCATGGCGAGGCCGTTGGCGCCTCAGTGGAAGTCGGCCAGCCGC |
| CTCCGTGGGAGAGAGGCAGGAAATCGGACCAATTCAGTAGCAGTGGGGCTTAAGGTTTATGAACGGGGTCTTGAGCG |
| GAGGCCTGAGCGTACAAACAGCTTCCCCACCCTCAGCCTCCCGGCGCCATTTCCCTTCACTGGGGTGGGGATGGG |
| GAGCTTTCACATGGCGGACGCTGCCCCGCTGGGGTGAAAGTGGGGCGCGGAGGCGGGACTTCTTATTCCCTTTCTAA |
| AGCACGCTGCTTCGGGGGCCACGGCGTCTCCTCGGAACCGTTGGTGATGTGTGTCAGTTAGGGTGTGGAAAGTCC |
| CCAGGCTCCCCAGCAGGCAGAAGTATGCAAAGCATGCATCTCAATTAGTCAGCAACCAGGTGTGGAAAGTCCCCAGG |
| CTCCCCAGCAGGCAGAAGTATGCAAAGCATGCATCTCAATTAGTCAGCAACCATAGTCCCGCCCCTAACTCCGCCCAT |
| CCCGCCCCTAACTCCGCCCAGTTCCGCCCATTCTCCGCCCCATGGCTGACTAATTTTTTTTATTTATGCAGAGGCCGAG |
| GCCGCCTCGGCCTCTGAGCTATTCCAGAAGTAGTGAGGAGGCTTTTTTGGAGGCCTTTTGCAAAAAGCTGCA |
| GATGATTGAACAAGATGGATTGCACGCAGGTTCTCCGGCCGCTTGGGTGGAGAGGCTATTCGGCTATGACTGGGCACA |
| ACAGACAATCGGCTGCTCTGATGCCGCCGTGTTCCGGCTGTCAGCGCAGGGGCGCCCGGTTCTTTTTGTCAAGACCG |
| ACCTGTCCGGTGCCCTGAATGAACTGCAGGACGAGGCAGCGCGGCTATCGTGGCTGGCCACGACGGGCGTTCCTTGC |
| GCAGCTGTGCTCGACGTTGTCACTGAAGCGGGAAGGGACTGGCTGCTATTGGGCGAAGTGCCGGGGCAGGATCTCCT |
| GTCATCTCACCTTGCTCCTGCCGAGAAAGTATCCATCATGGCTGATGCAATGCGGCGGCTGCATACGCTTGATCCGGC |
| TACCTGCCCATTCGACCACCAAGCGAAACATCGCATCGAGCGAGCACGTACTCGGATGGAAGCCGGTCTTGTCGATCA |
| GGATGATCTGGACGAAGAGCATCAGGGGCTCGCGCCAGCCGAACTGTTCGCCAGGCTCAAGGCGCGCATGCCCGACG |
| GCGAGGATCTCGTCGTGACCCATGGCGATGCCTGCTTGCCGAATATCATGGTGGAAAATGGCCGCTTTTCTGGATTCA |
| TCGACTGTGGCCGGCTGGGTGTGGCGGACCGCTATCAGGACATAGCGTTGGCTACCCGTGATATTGCTGAAGAGCTTG |
| GCGGCGAATGGGCTGACCGCTTCCTCGTGCTTTACGGTATCGCCGCTCCCGATTCGCAGCGCATCGCCTTCTATCGCC |
| TTCTTGACGAGTTCTTCTGAGATCCGTGACATAATTGGACAAACTACCTACAGAGATTTAAAGCTCTAAGGTAAATATA |
| AAATTTTTAAGTGTATAATGTGTTAAACTACTGATTCTAATTGTTTGTGTATTTTAGAT |
| TCCAACCTATGGAACTGATGAA |
| TGGGAGCAGTGGTGGAATGCCTTTAATGAGGAAAACCTGTTTTGCTCAGAAGAAATGCCATCTAGTGATGATGAGGCT |
| ACTGCTGACTCTCAACATTCTACTCCTCCAAAAAAGAAGAGAAAGGTAGAAGACCCCAAGGACTTTCCTTCAGAATTG |
| CTAAGTTTTTTGAGTCATGCTGTGTTTAGTAATAGAACTCTTGCTTGCTTTGCTATTTACACCACAAAGGAAAAAGCTG |
| CACTGCTATACAAGAAAATTATGGAAAAATATTCTGTAACCTTTATAAGTAGGCAT |
| AACAGTTATAATCATAACATACTGT |
| TTTTTCTTACTCCACACAGGCATAGAGTGTCTGCTATTAATAACTATGCTCAAAAAT |
| TGTGTACCTTTAGCTTTTTAATTT |
| GTAAAGGGGTTAATAAGGAATATTTGATGTATAGTGCCTTGACTAGAGATCATAATCAGCCATACCACATTTGTAGAGGT |
| TTTACTTGCTTTAAAAAACCTCCCACACCTCCCCCTGAACCTGAAACATAAAATGAATGCAATTGTTGTTGTTAACTTGT |
| TTATTGCAGCTTATAATGGTTACAAATAAAGCAATAGCATCACAAATTT |
| CACAAATAAAGCATTTTTTTCACTGCATTCTA |
| GTTGTGGTTTGTCCAAACTCATCAATGTATCTTATCATGTCTGGGCCCATCGATGCCGACGTAGCGCCTGATGCGGTAT |

| SEQUENCE LISTING FREE TEXT |
|---|
| TTTCTCCTTACGCATCTGTGCGGTATTTCACACCGCATATGGTGCACTCTCAGTACAATCTGCTCTGATGCCGCATAGT
TAAGCCAGCCCCGACACCCGCCAACACCCGCTGACGCGCCCTGACGGGCTTGTCTGCTCCCGGCATCCGCTTACAGA
CAAGCTGTGACCGTCTCCGGGAGCTGCATGTGTCAGAGGTTTCACCGTCATCACCGAAACGCGCGAGACGAAAGGG
CCTCGTGATACGCCTATTTTTATAGGTTAATGTCATGATAATAATGGTTTCTTAGACGTCAGGTGGCACTTTTCGGGGAA
ATGTGCGCGGAACCCCTATTTGTTTATTTTTCTAAATACATTCAAATATGTATCCGCTCATGAGACAATAACCCTGATAA
ATGCTTCAATAATATTGAAAAAGGAAGAGTATGAGTATTCAACATTTCCGTGTCGCCCTTATTCCCTTTTTTGCGGCATT
TTGCCTTCCTGTTTTTGCTCACCCAGAAACGCTGGTGAAAGTAAAAGATGCTGAAGATCAGTTGGGTGCACGAGTGGG
TTACATCGAACTGGATCTCAACAGCGGTAAGATCCTTGAGAGTTTTCGCCCCGAAGAACGTTTTCCAATGATGAGCAC
TTTTAAAGTTCTGCTATGTGGCGCGGTATTATCCCGTATTGACGCCGGGCAAGAGCAACTCGGTCGCCGCATACACTAT
TCTCAGAATGACTTGGTTGAGTACTCACCAGTCACAGAAAAGCATCTTACGGATGGCATGACAGTAAGAGAATTATGC
AGTGCTGCCATAACCATGAGTGATAACACTGCGGCCAACTTACTTCTGACAACGATCGGAGGACCGAAGGAGCTAACC
GCTTTTTTGCACAACATGGGGGATCATGTAACTCGCCTTGATCGTTGGGAACCGGAGCTGAATGAAGCCATACCAAAC
GACGAGCGTGACACCACGATGCCTGTAGCAATGGCAACAACGTTGCGCAAACTATTAACTGGCGAACTACTTACTCTA
GCTTCCCGGCAACAATTAATAGACTGGATGGAGGCGGATAAAGTTGCAGGACCACTTCTGCGCTCGGCCCTTCCGGCT
GGCTGGTTTATTGCTGATAAATCTGGAGCCGGTGAGCGTGGGTCTCGCGGTATCATTGCAGCACTGGGGCCAGATGGT
AAGCCCTCCCGTATCGTAGTTATCTACACGACGGGGAGTCAGGCAACTATGGATGAACGAAATAGACAGATCGCTGAG
ATAGGTGCCTCACTGATTAAGCATTGGTAACTGTCAGACCAAGTTTACTCATATATACTTTAGATTGATTTAAAACTTCA
TTTTTAATTTAAAAGGATCTAGGTGAAGATCCTTTTTGATAATCTCATGACCAAAATCCCTTAACGTGAGTTTTCGTTCC
ACTGAGCGTCAGACCCCGTAGAAAAGATCAAAGGATCTTCTTGAGATCCTTTTTTTCTGCGCGTAATCTGCTGCTTGCA
AACAAAAAAACCACCGCTACCAGCGGTGGTTTGTTTGCCGGATCAAGAGCTACCAACTCTTTTTCCGAAGGTAACTGG
CTTCAGCAGAGCGCAGATACCAAATACTGTTCTTCTAGTGTAGCCGTAGTTAGGCCACCACTTCAAGAACTCTGTAGCA
CCGCCTACATACCTCGCTCTGCTAATCCTGTTACCAGTGGCTGCTGCCAGTGGCGATAAGTCGTGTCTTACCGGGTTG
GACTCAAGACGATAGTTACCGGATAAGGCGCAGCGGTCGGGCTGAACGGGGGGTTCGTGCACACAGCCCAGCTTGGA
GCGAACGACCTACACCGAACTGAGATACCTACACGTGAGCTATGAGAAAGCGCCACGCTTCCCGAAGGGAGAAAGG
CGGACAGGTATCCGGTAAGCGGCAGGGTCGGAACAGGAGAGCGCACGAGGGAGCTTCCAGGGGGAAACGCCTGGTA
TCTTTATAGTCCTGTCGGGTTTCGCCACCTCTGACTTGAGCGTCGATTTTTGTGATGCTCGTCAGGGGGCGGAGCCT
ATGGAAAAACGCCAGCAACGCGGCCTTTTTACGGTTCCTGGCCTTTTGCTGGCCTTTTGCTCACATGTTCTTTCCTGC
GTTATCCCCTGATTCTGTGGATAACCGTATTACCGCCTTTGAGTGAGCTGATACCGCTCGCCGCAGCCGAACGACCGA
GCGCAGCGAGTCAGTGAGCGAGGAAGCGGAAGAGCGCCCAATACGCAAACCGCCTCTCCCCGCGCGTTGGCCGATTC
ATTAATGCAGCTGGCACCTCCGCGCCTACAGCTCAAGCCACATCCGAAGGGGGAGGGAGCCGGGAGCTGCGCGCGG
GGCCGCCGGGGGAGGGGTGGCACCGCCCACGCCGGGCGGCCACGAAGGGCGGGGCAGCGGGCGCGCGCGCGGCG
GGGGGAGGGGCCGGCGCCGCGCCCGCTGGGAATTGGGGCCCTAGGGGAGGGGCCGAGGCGCCGACGACCGCGGCA
CTTACCGTTCGCGGCGTGGCGCCCGGTGGTCCCCAAGGGGAGGGAAGGGGGAGGCGGGCGAGGACAGTGACCGG
AGTCTCCTCAGCGGTGGCTTTTCTGCTTGGCAGCCTCAGCGGCTGGCGCAAAACCGGACTCCGCCCACTTCCTCGC
CCGCCGGTGCGAGGGTGTGGAATCCTCCAGACGCTGGGGAGGGGGAGTTGGGAGCTTAAAAACTAGTACCCCTTTG
GGACCACTTTCAGCAGCGAACTCTCCTGTACACCAGGGGTCAGTTCCACAGACGCGGGCCAGGGTGGGTCATTGCG
GCGTGAACAATAATTTGACTAGAAGTTGATTCGGTGTTTCCGGAAGGGGCCGAGTCAATCCGCCGAGTTGGGGCAC
GGAAAACAAAAAGGGAAGGCTACTAAGATTTTTCTGGCGGGGTTATCATTGGCGTAACTGCAGGGACCACCTCCCGG
GTTGAGGGGCTGGATCTCCAGGCTGCGGATTAAGCCCCTCCCGTCGGCGTTAATTTCAAACTGCGCGACGTTTCTCA
CCTGCCTTCGCCAAGGCAGGGCCGGGACCCTATTCCAAGAGGTAGTAACTAGCAGGACTCTAGCCTTCCGCAATTCA
TTGAGCGCATTTACGGAAGTAACGTCGGGTACTCTCTGGCCGCAAGGGTGGAGGATGTACGCATTTGGCGTAAGG
TGGGGCGTAGAGCCTTCCCGCCATTGGCGGCGGATAGGGCGTTTACGCGACGGCCTGACGTAGCGGAAGACGCCTTA
GTGGGGGGAAGGTTCTAGAAAAGCGGCGGCAGCGGCTCTAGCGGCAGTAGCAGCAGCGCCGGGTCCCGTGCGGAG
GTGCTCCTCGCAGAGTTGTTTCTCCAGCAGCGGCAGTTCTCACTACAGCGCCAGGACGAGTCCGGTTCGTGTTCGTCC
GCGGAGATCTCTCTCATCTCGCTCGGCTGCGGGAAATCGGGCGTACTGAGTCCGCGATGGAGGTAACGGGTT
TGAAATCAATGAGTTATTGAAAAGGGCATGGCGAGGCCGTTGCGCCTCAGTGGAAGTCGGCCAGCCGCCTCCGTGG
GAGAGAGGCAGGAAATCGGACCAATTCAGTAGCAGTGGGGCTTAAGGTTTATGAACGGGGTCTTGAGCGGAGGCCTG
AGCGTACAAACAGCTTCCCCACCCTCAGCCTCCCGGCGCCATTTCCCTTCACTGGGGGTGGGGGATGGGGAGCTTTC
ACATGGCGGACGCTGCCCCGCTGGGGTGAAAGTGGGGCGCGGAGGCGGGACTTCTTATTCCCTTTCTAAAGCACGCT
GCTTCGGGGGCCACGGCGTCTCCTCGGAAAGCTT | cDNA encoding human omalizumab (OMLH) light chain that replaced the nucleotide sequences No. 658 to No. 668 of pNC32c-U533.
<SEQ ID NO: 11>
CGCGCCACCATGGGTTGGTCTTGTATCATCTTATTTTTAGTTGCTACTGCTACTGGTGTTCATTCTGATATACAGCTCAC
CCAAAGCCCATCATCTCTGTCTGCAAGCGTCGGCGACAGGGTGACCATTACCTGTCGCGCAAGCCAAAGCGTTGACTA
CGACGGCGACAGCTACATGAACTGGTACCAGCAGAAGCCCGGCAAGGCTCCTAAGCTGCTGATCTATGCCGCCTCCTA
CCTTGAATCTGGAGTGCCTTCTCGTTTTTCCGGCTCAGGGTCCGGAACTGATTTTACCCTGACCATTTCCTCCCTCCAG
CCCGAGGATTTTGCCACTTACTACTGTCAGCAGTCCCACGAGGACCCATATACATTCGGACAAGGTACAAAGGTAGAA
ATCAAGCGTACGGTGGCTGCCCCATCCGTGTTCATATTTCCTCCTAGCGACGAACAACTCAAGTCCGGTACCGCCAGC
GTGGTCTGCCTGTTGAACAATTTTTATCCAAGAGAAGCTAAGGTCCAGTGGAAGGTTGACAACGCCCTTCAGTCCGGA
AATAGCCAAGAGAGCGTCACCGAACAGGACTCCAAGGACAGTACATACTCACTGAGCTCTACACTGACCCTTTCTAAG
GCCGACTACGAGAAGCACAAGGTCTACGCATGCGAAGTGACCCATCAGGGACTCAGTAGCCCTGTAACAAAGAGTTTT
AATCGAGGCGAGTGCTAAGCGAT cDNA encoding human omalizumab (OMLH) heavy chain that replaced the nucleotide sequences No. 3081 to No. 3092 of pNC32c-U533.
<SEQ ID NO: 12>
GGCCGCCACCATGGAATTTGGTTTATCTTGGGTTTTTTTAGTTGCTTTATTAAGAGGTGTTCAATGTGAGGTGCAGTTG
GTCGAATCCGGCGGCGGACTCGTGCAACCAGGCGGAAGTTTGCGGCTGTCCTGCGCAGTGTCTGGTTACAGCATCAC
CTCCGGGTATAGCTGGAACTGGATCCGCCAGGCTCCTGGAAAGGGCCTTGAGTGGGTGGCTTCCATTACCTACGACG
GCTCCACTAACTATAACCCGAGCGTCAAAGGCAGATCACCATCTCTCGGGACGACTCAAAGAATACCTTCTACCTGC
AGATGAACTCACTGAGGGCCGAAGATACCGCAGTTTACTACTGCGCCAGGGGGTCCCACTATTTCGGCCACTGGCACT
TCGCCGTGTGGGGACAGGGCACACTCGTGACCGTTAGTAGCGCTAGCACCAAAGGCCCCTCTGTGTTCCCACTTGCT
CCCTCCAGTAAATCTACCTCCGGAGGAACCGCAGCCCTCGGCTGCCTGGTGAAGGATTACTTCCCAGAGCCCGTCACC
GTCTCTTGGAACTCCGGAGCCTTGACTAGCGGAGTGCACACTTTCCCTGCTGTATTGCAGTCCAGCGGCTTGTATTCA
CTGAGTAGCGTCGTCACCGTGCCTTCAAGCAGCCTCGGGACACAGACATACATATGTAATGTCAACCATAAGCCATCA

SEQUENCE LISTING FREE TEXT

```
AACACTAAAGTTGATAAAAAGGTGGAACCTAAGAGTTGCGATAAGACCCATACCTGTCCTCCTTGCCCTGCTCCTGAG
CTGCTGGGAGGCCCTAGCGTGTTTCTGTTCCCCCCCAAGCCCAAAGATACACTGATGATTTCCCGCACACCTGAAGTA
ACATGTGTCGTGGTTGATGTGAGTCACGAGGATCCAGAGGTCAAGTTTAATTGGTACGCGGAGTGGAGGTGCAC
AACGCTAAGACTAAGCCTCGGGAGGAACAGTACAACAGCACATACCGCGTGGTCAGCGTTTTGACTGTGCTGCATCAA
GACTGGCTCAATGGAAAGGAATACAAGTGCAAGGTCTCTAATAAAGCCCTCCCCGCTCCTATTGAGAAGACTATTTCTA
AAGCCAAGGGCCAGCCTCGCGAACCTCAGGTATATACTTTGCCACCCTCTCGCGAAGAAATGACAAAGAATCAGGTCT
CACTCACTTGCCTCGTCAAAGGGTTTTACCCTTCTGACATCGCTGTCGAATGGGAAAGTAATGGTCAGCCAGAAAACA
ATTACAAGACTACTCCACCAGTGCTCGATTCTGATGGAAGTTTCTTTCTCTACAGTAAGCTCACTGTGGACAAATCTCG
CTGGCAGCAGGGTAACGTATTCTCATGCTCCGTGATGCATGAAGCCCTCCACAACCATTACACCCAGAAGAGCCTGTC
TCTGAGCCCAGGCAAGTAACCTGCA
```

A sequence comprising BstBI recognition site that replaced the nucleotide sequences No. 5309 to No. 5311 of UCOE-Hu-P.
<SEQ ID NO: 13>
```
CCTAGTAGTAGTAGTAGTTCGAAG
```

Sequence comprising cDNA encoding a human omalizumab light chain (OML) as linked to Simian Virus 40 polyadenylation signal (SV40pA), guinea pig cytomegalovirus promoter (PgpCMV) and cDNA encoding a human omalizumab heavy chain (OMH).
<SEQ ID NO: 14>
```
CCCACCATGGGTTGGTCTTGTATCATCTTATTTTTAGTTGCTACTGCTACTGGTGTTCATTCTGATATACAGCTCACCCA
AAGCCCATCATCTCTGTCTGCAAGCGTCGGCGACAGGGTGACCATTACCTGTCGCGCAAGCCAAAGCGTTGACTACGA
CGGCGACAGCTACATGAACTGGTACCAGCAGAAGCCCGGCAAGGCTCCTAAGCTGCTGATCTATGCCGCCTCCTACCT
TGAATCTGGAGTGCCTTCTCGTTTTTCCGGCTCAGGGTCCGGAACTGATTTTACCCTGACCATTTCCTCCCTCCAGCCC
GAGGATTTTGCCACTTACTACTGTCAGCAGTCCCACGAGGACCCATATACATTCGGACAAGGTACAAAGGTAGAAATC
AAGCGTACGGTGGCTGCCCCATCCGTGTTCATATTTCCTCCTAGCGACGAACAACTCAAGTCCGGTACCGCCAGCGTG
GTCTGCCTGTTGAACAATTTTTATCCAAGAGAAGCTAAGGTCCAGTGGAAGGTTGACAACGCCCTTCAGTCCGGAAAT
AGCCAAGAGAGCGTCACCGAACAGGACTCCAAGGACAGTACATACTCACTGAGCTCTACACTGACCCTTTCTAAGGCC
GACTACGAGAAGCACAAGGTCTACGCATGCGAAGTGACCCATCAGGGACTCAGTAGCCCTGTAACAAGAGTTTTAAT
CGAGGCGAGTGCTAAGCGATCGCGCTAGCGCGGCCACGTAGTCGACTACGTAGAGCTCGGTACCCGGGGATCCTCTA
GAGTCGACCTGCAGGCATGCAAGCTGGCCGCGACTCTAGATCATAATCAGCCATACCACATTTGTAGAGGTTTTACTTG
CTTTAAAAAACCTCCCACACCTCCCCCTGAACCTGAAACATAAAATGAATGCAATTGTTGTTGTTAACTTGTTTATTGCA
GCTTATAATGGTTACAAATAAAGCAATAGCATCACAAATTTCACAAATAAAGCATTTTTTTTCACTGCATTCTAGTTGTGG
TTTGTCCAAACTCATCAATGTATCTTAACCGGTTATGTTACTTGGCAGTGGGTCCCATGGAAAGTCCCTGGACGTGGGA
CATCTGATTAATACGTGAGGAGGTCAGCCATGTTCTTTTTGGCAAAGGACTACGGTCATTGGACGTTTGATTGGCATGG
GATAGGGTCAGCCAGAGTTAACAGTGTTCTTTTGGCAAAGGGATACGTGGAAAGTCCCGGGCCATTTACAGTAAACTG
ATACGGGGACAAAGCACAGCCATATTTAGTCATGTATTGCTTGGCAGAGGGTCTATGGAAAGTCCCTGGACGTGGGAC
GTCTGATTAATATGAAAGAAGGTCAGCCAGAGGTAGCTGTGTCCTTTTTGGCAAAGGGATACGGTTATGGGACGTTTG
ATTGGACTGGGATAGGGTCAGCCAGAGTTAACAGTGTTCTTTTGGCAAAGGAAACGTGGAAAGTCCCGGGCCATTTAC
AGTAAACTGATACTGGGACAAAGTACACCCATATTTAGTCATGTTCTTTTTGGCAAAGAGCATCTGGAAAGTCCCGGGC
AGCATTATAGTCACTTGGCAGAGGGAAAGGGTCACTCAGAGTTAAGTACATCTTTCCAGGGCCAATATTCCAGTAAATT
ACACTTAGTTTTATGCAAATCAGCCACAAAGGGGATTTTCCCGGTCAATTATGACTTTTTCCTTAGTCATGCGGTATCCA
ATTACTGCCAAATTGGCAGTACATACTAGGTGATTCACTGACATTTGGCCGTCCTCTGGAAAGTCCCTGGAAACCGCTC
AAGTACTGTATCATGGTGACTTTGCATTTTTGGAGAGCACGCCCCACTCCACCATTGGTCCACGTACCCTATGGGGGA
GTGGTTTATGAGTATATAAGGGGCTCCGGTTTAGAAGCCGGGCAGAGCGGAATTCGAGCTCCCTGCAGGTTAGTTAAG
TTAACGGCGCGCCACCATGGAATTTGGTTTATCTTGGGTTTTTTTAGTTGCTTTATTAAGAGGTGTTCAATGTGAGGTG
CAGTTGGTCGAATCCGGCGGCGGACTCGTGCAACCAGGCGGAAGTTTGCGGCTGTCCTGCGCAGTGTCTGGTTACAG
CATCACCTCCGGGTATAGCTGGAACTGGATCCGCCAGGCTCCTGGAAAGGGGCTTGAGTGGGTGGCTTCCATTACCTA
CGACGGCTCCACTAACTATAACCCGAGCGTCAAAGGCAGAATCACCATCTCTCGGGACGACTCAAAGAATACCTTCTA
CCTGCAGATGAACTCACTGAGGGCCGAAGATACCGCAGTTTACTACTGCGCCAGGGGGTCCCACTATTTCGGCCACTG
GCACTTCGCCGTGTGGGACAGGGCACACTCGTGACCGTTAGTAGCGCTAGCACCAAAGGCCCCTCTGTGTTCCCAC
TTGCTCCCTCCAGTAAATCTACCTCCGGAGGAACCGCAGCCCTCGGCTGCCTGGTGAAGGATTACTTCCCAGAGCCCG
TCACCGTCTCTTGGAACTCCGGAGCCTTGACTAGCGGAGTGCACACTTTCCCTGCTGTATTGCAGTCCAGCGGCTTGT
ATTCACTGAGTAGCGTCGTCACCGTGCCTTCAAGCAGCCTCGGGACAGACATACATATGTAATGTGAATCAACCATAAGCC
ATCAAACACTAAAGTTGATAAAAAGGTGGAACCTAAGAGTTGCGATAAGACCCATACCTGTCCTCCTTGCCCTGCTCCT
GAGCTGCTGGGAGGCCCTAGCGTGTTTCTGTTCCCCCCCAAGCCCAAAGATACACTGATGATTTCCCGCACACCTGAA
GTAACATGTGTCGTGGTTGATGTGAGTCACGAGGATCCAGAGGTCAAGTTTAATTGGTACGCGGACGGAGTGGAGGTG
CACAACGCTAAGACTAAGCCTCGGGAGGAACAGTACAACAGCACATACCGCGTGGTCAGCGTTTTGACTGTGCTGCAT
CAAGACTGGCTCAATGGAAAGGAATACAAGTGCAAGGTCTCTAATAAAGCCCTCCCCGCTCCTATTGAGAAGACTATTT
CTAAAGCCAAGGGCCAGCCTCGCGAACCTCAGGTATATACTTTGCCACCCTCTCGCGAAGAAATGACAAAGAATCAGG
TCTCACTCACTTGCCTCGTCAAAGGGTTTTACCCTTCTGACATCGCTGTCGAATGGGAAAGTAATGGTCAGCCAGAAA
ACAATTACAAGACTACTCCACCAGTGCTCGATTCTGATGGAAGTTTCTTTCTCTACAGTAAGCTCACTGTGGACAAATC
TCGCTGGCAGCAGGGTAACGTATTCTCATGCTCCGTGATGCATGAAGCCCTCCACAACCATTACACCCAGAAGAGCCT
GTCTCTGAGCCCAGGCAAGTAATCTAGATT
```

Amino acid sequence of canine CTLA-4-Ig.
<SEQ ID NO: 15>
MAGFGFRRHGAQPDLASRTWPCTALFSLLFIPVFSKGMHVAQPAVVLASSRGVASFVCEYGSSGNAAEVRVTVLRQAGS
QMTEVCAATYTVEDELAFLDDSTCTGTSSGNKVNLTIQGLRAMDTGLYICKVELMYPPPYYVGMGNGTQIYVIDPEPCP
DSDPKESTCKCISPCPVPESLGGPSVFIFPPKPKDILRITRTPEITCVVLDLGREDPEVQ-
ISWFVDGKEVHTAKTQPREQQ
FNSTYRVVSVLPIEHQDWLTGKEFKCRVNHIGLPSPIER-
TISKARGQAHQPSVYVLPPSPKELSSSDTVTLTCLIKDFFPP
EIDVEWQSNGQPEPESKYHTTAPQLDEDGSYFLYSKLSVDKSRWQQGDTFTCAVMHEALQNHYTDLSLSHSPGK

SEQUENCE LISTING FREE TEXT

Nucleotide sequence of canine CTLA-4-Ig after codon optimization.
<SEQ ID NO: 16>
ATGGCTGGATTTGGATTCAGAAGGCACGGAGCCCAGCCCGACCTGGCATCTCGCACTTGGCCCTGTACCGCACTGTTT
TCACTGCTGTTCATCCCAGTGTTCAGCAAGGGAATGCACGTGGCTCAGCCAGCTGTGGTGCTGGCTTCCAGCAGAGG
CGTGGCTTCCTTCGTGTGCGAGTACGGCTCTTCCGGCAACGCCGCTGAGGTGAGAGTGACCGTGCTGAGGCAGGCTG
GCTCCCAGATGACAGAGGTGTGCGCCGCTACCTATACAGTGGAGGACGAGCTGGCTTTCCTGGACGATAGCACCTGTA
CAGGCACCAGCTCTGGCAACAAGGTCAATCTGACCATCCAGGGCCTGCGCGCCATGGATACAGGCCTGTACATCTGTA
AGGTGGAGCTGATGTATCCCCCTCCATACTATGTGGGCATGGGCAATGGCACCCAGATCTACGTGATCGACCCCGAGC
CTTGCCCAGACTCTGATCCAAAGGAGTCGACATGCAAGTGTATCTCTCCATGTCCTGTGCCAGAGAGCCTGGGAGGAC
CTTCCGTGTTCATCTTTCCCCCTAAGCCAAAGGATATCCTGAGGATCACACGGACCCCTGAGATCACCTGCGTGGTGC
TGGACCTGGGAAGGGAGGATCCAGAGGTGCAGATCTCCTGGTTCGTGGACGGCAAGGAGGTGCATACCGCTAAGACA
CAGCCCAGAGAGCAGCAGTTTAACTCCACCTATCGCGTGGTGAGCGTGCTGCCTATCGAGCACCAGGATTGGCTGACA
GGCAAGGAGTTTAAGTGCCGGGTGAATCATATCGGCCTGCCCTCTCCTATCGAGAGGACCATCTCCAAGGCTAGGGA
CAGGCTCACCAGCCAAGCGTGTACGTGCTGCCACCCTCTCCTAAGGAGCTGTCCAGCTCTGACACAGTGACCCTGAC
ATGTCTGATCAAGGACTTCTTTCCTCCAGAGATCGACGTGGAGTGGCAGTCCAACGGCCAGCCAGAGCCCGAGAGCA
AGTATCATACCACAGCCCCCAGCTGGACGAGGATGGCTCTTACTTCCTGTATTCCAAGCTGAGCGTGGACAAGTCCA
GGTGGCAGCAGGGCGATACCTTTACATGTGCTGTGATGCACGAAGCCCTGCAGAATCATTACACCGACCTGTCACTGT
CCCACTCCCTGGCAAATAA Entire nucleotide sequence of pDC62c5-U533 that has only one site for foreign gene insertion.
<SEQ ID NO: 17>
CGATGTACGGGCCAGATATACGCGTTGACATTGATTATTGACTAGTCGCGTTACATAACTTACGGTAAATGGCCCGCCT
GGCTGACCGCCCAACGACCCCCGCCCATTGACGTCAATAATGACGTATGTTCCCATAGTAACGCCAATAGGGACTTTC
CATTGACGTCAATGGGTGGAGTATTTACGGTAAACTGCCCACTTGGCAGTACATCAAGTGTATCATATGCCAAGTCCGC
CCCCTATTGACGTCAATGACGGTAAATGGCCCGCCTGGCATTATGCCCAGTACATGACCTTACGGGACTTTCCTACTTG
GCAGTACATCTACGTATTAGTCATCGCTATTACCATGGTGATGCGGTTTTGGCAGTACACCAATGGGCGTGGATAGCGG
TTTGACTCACGGGGATTTCCAAGTCTCCACCCCATTGACGTCAATGGGAGTTTGTTTTGGCACCAAAATCAACGGGAC
TTTCCAAAATGTCGTAATAACCCCGCCCGTTGACGCAAATGGGCGGTAGGCGTGTACGGTGGGAGGTCTATATAAGC
AGAGCTCGTTTAGTGAACCGTCAGATCCTCACTCTCTTCCGCATCGCTGTCTGCGAGGGCCAGCTGTTGGGCTCGCGG
TTGAGGACAAACTCTTCGCGGTCTTTCCAGTACTCTTGGATCGGAAACCCGTCGGCCTCCGAACGGTACTCCGCCACC
GAGGGGACCTGAGCGAGTCCGCATCGACCGGATCGGAAAACCTCTCGAGAAAGGCGTCTAACCAGTCACAGTCGCAAG
GTAGGCTGAGCACCGTGGCGGGCGGCAGCGGGTGGCGGTCGGGGTTGTTTCTGGCGGAGGTGCTGCTGATGATGTA
ATTAAAGTAGGCGGTCTTGAGACGGCGGATGGTCGAGGTGAGGTGTGGCAGGCTTGAGATCCAGCTGTTGGGGTGAG
TACTCCCTCTCAAAAGCGGGCATGACTTCTGCGCTAAGATTGTCAGTTTCCAAAAACGAGGAGGATTTGATATTCACCT
GGCCCGATCTGGCCATACACTTGAGTGACAATGACATCCACTTTGCCTTTCTCTCCACAGGTGTCCACTCCCAGGTCC
AAGGCGCGCCGCGATCGCGCCTCGACTGTGCCTTCTAGTTGCCAGCCATCTGTTGTTTGCCCCTCCCCCGTGCCTTCC
TTGACCCTGGAAGGTGCCACTCCCACTGTCCTTTCCTAATAAAATGAGGAAATTGCATCGCATTGTCTGAGTAGGTGTC
ATTCTATTCTGGGGGGTGGGGTGGGGCAGGACAGCAAGGGGGAGGATTGGGAAGACAATAGCAGGCATGCTGGGGA
GGATCTCCGCGGGGCCTCCGCGCCTACAGCTCAAGCCACATCCAAGGGGGAGGGAGGCCTGAGCTGCGCGGG
GCCGCCGGGGGAGGGGTGGCACCGCCCACGCCGGGCGGCCACGAAGGGCGGGGCAGCGGCGCGCGCGGCGG
GGGGAGGGGCCGGCGCCGCGCCCGCTGGGAATTGGGGCCCTAGGGGGAGGGCGGAGGCGCCGACGACCGCGGCAC
TTACCGTTCGCGGCGTGGCGCCCGGTGGTCCCCAAGGGGAGGGAAGGGGGACGCGGGCCGAGGACAGTGACCGGA
GTCTCCTCAGCGGTGGCTTTTCTGCTTGGCAGCTCAGCGGCTGGCGCCAAAACCGGACTCCGCCCCACTTCCTCGCC
CGCCGGTGCGAGGGTGTGGAATCCTCCAGCGCTGGGGAGGGGGAGTTGGGAGCTTAAAAACTAGTACCCCTTTGG
GACCACTTTCAGCAGCGAACTCTCCTGTACACCAGGGTCAGTTCCACAGACGCGGGCCAGGGTGGTCATTGCGG
CGTGAACAATAATTTGACTAGAAGTTGATTCGGGTGTTTCCGGAAGGGGCCGAGTCAATCCGCCGAGTTGGGCACG
GAAAACAAAAAGGGAAGGCTACTAAGATTTTTCTGGCGGGGGTTATCATTGGCGTAACTGCAGGGACCCACCTCCCGGG
TTGAGGGGGCTGGATCTCCAGGCTGCGGATTAAGCCCCTCCCGTCGGCGTTAATTTCAAACTGCGCGACGTTTCTCAC
CTGCCTTCGCCAAGGCAGGGCCGGGACCCTATTCCAAGAGGTAGTAACTAGCAGGACTCTAGCCTTCCGCAATTCAT
TGAGCGCATTTACGGAAGTAACGTCGGGTACTGTCTCTGGCCGCAAGGGTGGGAGGAGTACGCATTTGGCGTAAGGT
GGGGCGTAGAGCCTTCCCGCCATTGGCGGCGGATAGGGCGTTTACGCGACGAATCTGACGTAGCGGAAGACGCCTTAG
TGGGGGGAAGGTTCTAGAAAAGCGGCGGCAGCGGCTCTAGCGGCAGTAGCAGCAGCCGGGTCCCGTGCGGAGG
TGCTCCTCGCAGAGTTGTTTCTCCAGCAGCGGCAGTTCTCACTACAGCGCCAGGACGAGTCCGGTTCGTGTTCGTCCG
CGGAGATCTCTCTCATCTCGCTCGGCTGCGGGAAATCGGGCTGAAGCGACTGAGTCCGCGATGGAGGTAACGGGTTT
GAAATCAATGAGTTATTGAAAAGGCATGGCGAGGCCGTTGGCGCCTCAGTGGAAGTCGGCCAGCCGCCTCCGTGGG
AGAGAGGCAGGAAATCGGACCAATTCAGTAGCAGTGGGGCTTAAGGTTTATGAACGGGGTCTTGAGCGGAGGCCTGA
GCGTACAAACAGCTTCCCCACCCTCAGCCTCCCGGCGCCATTTCCCTTCACTGGGGTGGGGATGGGGAGCTTTCA
CATGGCGGACGCTGCCCCGCTGGGGTGAAAGTGGGGCGCGGAGGCGGGACTTCTTATTCCCTTTCTAAAGCACGCTG
CTTCGGGGGCCACGGCGTCTCCTCGGAGAATTCaaatgggACCGGTTGTGGAATGTGTGTCAGTTAGGGTGTGGAAAGT
CCCCAGGCTCCCCAGCAGGCAGAAGTATGCAAAGCATGCATCTCAATTAGTCAGCAACCATAGTCCCGCCCCTAACTC
CGCCCATCCCGCCCCTAACTCCGCCCAGTTCCGCCCATTCTCCGCCCCATGGCTGACTAATTTTTTTTATTTATGCAGA
GGCCGAGGCCGCCTCGGCCTCTGAGCTATTCCAGAAGTAGTGAGGAGGCTTTTTTGGAGGCCTAGGCTTTTGCAAAA
AGCTGCAGATGGTACGACCATTAAATTGTATTGTAGCAGTATCACAAAATATGGGTATTGGTAAAATGGTGATTTACC
ATGGCCACCATTACGAAATGAATTTAAATATTTTCAACGAATGACTACTACTTCATCAGTAGAAGGTAAACAAAATTTAG
TAATTATGGGTCGAAAAACTTGGTTTTCAATTCCTGAGAAGAATGCGACCTTTAAAGGACAGAATTAATATAGTTCTCAG
TAGAGAACTCAAAGAACCACCACGAGGAGCTCATTTCTTGCCAAAAGTTTGGATGATGCCTAAGACTTATTGAACAA
CCGGAATTGGCAAGTAAAGTAGACATGGTTTGGATAGTCGGAGGCAGTTCTGTTTACCAGGAAGCCATGAATCAACCA
GGCCACCTCAGACTCTTTGTGACAAGGATCATGCAGGAATTTGAAAGTGACACGTTTTTCCCAGAAATTGATTTGGGG
AAATATAAACTTCTCCCAGAATACCCAGGCGTCCTCTCTGAGGTCCAGGAGGAAAAAGGCATCAAGTATAAGTTTGAA
GTCTACGAGAAGAAAGACTAAAGATCCGTGACATAATTGGACAAACTACCTACAGAGATTTAAAGCTCTAAGGTAAATA
TAAAATTTTTAAGTGTATAATGTGTTAAACTACTGATTCTAATTGTTTGTGTATTTTA-
GATTCCAACCTATGGAACTGATG
AATGGGAGCAGTGGTGGAATGCCTTTAATGAGGAAAACCTGTTTTGCTCAGAAGAAATGCCATCTAGTGATGATGAGG
CTACTGCTGACTCTCAACATTCTACTCCTCCAAAAAAGAAGAGAAAGGTAGAAGACCCCAAGGACTTTCCTTCAGAAT
TGCTAAGTTTTTTGAGTCATGCTGTGTTTAGTAATAGAACTCTTGCTTGCTTTGCTATTTACACCACAAAGGAAAAGC

```
TGCACTGCTATACAAGAAAATTATGGAAAAATATTCTGTAACCTTTATAAGTAGGCAT-
AACAGTTATAATCATAACATACT
GTTTTTTCTTACTCCACACAGGCATAGAGTGTCTGCTATTAATAACTATGCTCAAAAATTGTGTACCTTTAGCTTTTTAA
TTTGTAAAGGGGTTAATAAGGAATATTTGATGTATAGTGCCTTGACTAGAGATCATAATCAGCCATACCACATTTGTAGA
GGTTTTACTTGCTTTAAAAAACCTCCCACACCTCCCCCTGAACCTGAAACATAAAATGAATGCAATTGTTGTTGTTAAC
TTGTTTATTGCAGCTTATAATGGTTACAAATAAAGCAATAGCATCACAAATTTCACAAATAAAGCATTTTTTTCACTGCA
TTCTAGTTGTGGTTTGTCCAAACTCATCAATGTATCTTATCATGTCTGGGCCCATCGATGCCGACGTAGCGCTGATGCG
GTATTTTCTCCTTACGCATCTGTGCGGTATTTCACACCGCATATGGTGCACTCTCAGTACAATCTGCTCTGATGCCGCAT
AGTTAAGCCAGCCCCGACACCCGCCAACACCCGCTGACGCGCCTGACGGGCTTGTCTGCTCCCGGCATCCGCTTAC
AGACAAGCTGTGACCGTCTCCGGGAGCTGCATGTGTCAGAGGTTTTCACCGTCATCACCGAAACGCGCGAGACGAAA
GGGCCTCGTGATACGCCTATTTTTATAGGTTAATGTCATGATAATAATGGTTTCTTAGACGTCAGGTGGCACTTTTCGG
GGAAATGTGCGCGGAACCCCTATTTGTTTATTTTTCTAAATACATTCAAATATGTATCCGCTCATGAGACAATAACCCTG
ATAAATGCTTCAATAATATTGAAAAGGAAGAGTATGAGTATTCAACATTTCCGTGTCGCCCTTATTCCCTTTTTTGCGG
CATTTTGCCTTCCTGTTTTTGCTCACCCAGAAACGCTGGTGAAAGTAAAAGATGCTGAAGATCAGTTGGGTGCACGAG
TGGGTTACATCGAACTGGATCTCAACAGCGGTAAGATCCTTGAGAGTTTTCGCCCCGAAGAACGTTTTCCAATGATGA
GCACTTTTAAAGTTCTGCTATGTGGCGCGGTATTATCCCGTATTGACGCCGGGCAAGAGCAACTCGGTCGCCGCATAC
ACTATTCTCAGAATGACTTGGTTGAGTACTCACCAGTCACAGAAAAGCATCTTACGGATGGCATGACAGTAAGAGAATT
ATGCAGTGCTGCCATAACCATGAGTGATAACACTGCGGCCAACTTACTTCTGACAACGATCGGAGGACCGAAGGAGCT
AACCGCTTTTTTGCACAACATGGGGGATCATGTAACTCGCCTTGATCGTTGGGAACCGGAGCTGAATGAAGCCATACC
AAACGACGAGCGTGACACCACGATGCCTGTAGCAATGGCAACAACGTTGCGCAAACTATTAACTGGCGAACTACTTAC
TCTAGCTTCCCGGCAACAATTAATAGACTGGATGGAGGCGGATAAAGTTGCAGGACCACTTCTGCGCTCGGCCCTTCC
GGCTGGCTGGTTTATTGCTGATAAATCTGGAGCCGGTGAGCGTGGGTCTCGCGGTATCATTGCAGCACTGGGGCCAGA
TGGTAAGCCCTCCCGTATCGTAGTTATCTACACGACGGGGAGTCAGGCAACTATGGATGAACGAAATAGACAGATCGC
TGAGATAGGTGCCTCACTGATTAAGCATTGGTAACTGTCAGACCAAGTTTACTCATATATACTTTAGATTGATTTAAAAC
TTCATTTTTAATTTAAAAGGATCTAGGTGAAGATCCTTTTTGATAATCTCATGACCAAAATCCCTTAACGTGAGTTTTCG
TTCCACTGAGCGTCAGACCCCGTAGAAAAGATCAAAGGATCTTCTTGAGATCCTTTTTTTCTGCGCGTAATCTGCTGCT
TGCAAACAAAAAAACCACCGCTACCAGCGGTGGTTTGTTTGCCGGATCAAGAGCTACCAACTCTTTTTCCGAAGGTAA
CTGGCTTCAGCAGAGCGCAGATACCAAATACTGTTCTTCTAGTGTAGCCGTAGTTAGGCCACCACTTCAAGAACTCTGT
AGCACCGCCTACATACCTCGCTCTGCTAATCCTGTTACCAGTGGCTGCTGCCAGTGGCGATAAGTCGTGTCTTACCGG
GTTGGACTCAAGACGATAGTTACCGGATAAGGCGCAGCGGTCGGGCTGAACGGGGGGTTCGTGCACACAGCCCAGCT
TGGAGCGAACGACCTACACCGAACTGAGATACCTACAGCGTGAGCATTGAGAAAGCGCCACGCTTCCCGAAGGGAGA
AAGGCGGACAGGTATCCGGTAAGCGGCAGGGTCGGAACAGGAGAGCGCACAGGGAGCTTCCAGGGGGAAACGCCT
GGTATCTTTATAGTCCTGTCGGGTTTCGCCACCTCTGACTTGAGCGTCGATTTTTGTGATGCTCGTCAGGGGGGCGGA
GCCTATGGAAAAACGCCAGCAACGCGGCCTTTTTACGGTTCCTGGCCTTTTGCTGGCCTTTTGCTCACATGTTCTTTCC
TGCGTTATCCCCTGATTCTGTGGATAACCGTATTACCGCCTTTGAGTGAGCTGATACCGCTCGCCGCAGCCGAACGAC
CGAGCGCAGCGAGTCAGTGAGCGAGGAAGCGGAAGAGCGCCCAATACGCAAACCGCCTCTCCCCGCGCGTTGGCCG
ATTCATTAATGCAGCTGGGCCCTCCGCGCCTACAGCTCAAGCCACATCCGAAGGGGGAGGGAGCCGGGAGCTGCGCG
CGGGGCCGCCGGGGGAGGGGTGGCACCGCCCACGCCGGGCGGCCACGAAGGGCGGGGCAGCGGGCGCGCGCG
GCGGGGGGAGGGGCCGGCGCCGCGCCCGCTGGGAATTGGGGCCCTAGGGGGAGGGCGGAGGCGCCGACGACGCG
GCACTTACCGTTCGCGGCGTGCGCCCGGTGGTCCCCAAGGGGAGGGAAGGGGGAGGCGGGGCGAGGACAGTGACC
GGAGTCTCCTCAGCGGTGGCTTTTCTGCTTGGCAGCCTCAGCGGCTGGCGCCAAAACCGGACTCCGCCCACTTCCTC
GCCCGCCGGTGCGAGGGTGTGGAATCCTCCAGACGCTGGGGAGGGGGAGTTGGGAGCTTAAAAACTAGTACCCCTT
TGGGACCACTTTCAGCAGCGAACTCTCCTGTACACCAGGGGTCAGTTCCACAGACGCGGGCCAGGGGTGGGTCATTG
CGGCGTGAACAATAATTTGACTAGAAGTTGATTCGGGTGTTTCCGGAAGGGGCCAGGTCAATCCGCCGAGTTGGGGC
ACGGAAAACAAAAAGGGAAGGCTACTAAGATTTTTCTGGCGGGGGTTATCATTGGCGTAACTGCAGGGACCACCTCCC
GGGTTGAGGGGGCTGGATCTCCAGGCTGCGGATTAAGCCCCTCCCGTCGGCGTTAATTTCAAACTGCGCGACGTTTCT
CACCTGCCTTCGCCAAGGCAGGGGCCGGGACCCTATTCCAAGAGGTAGTAACTAGCAGGACTCTAGCCTTCCGCAATT
CATTGAGCGCATTTACGGAAGTAACGTCGGGTACTGTCTCTGGCCGCAAGGGTGGGAGGAGTACGCATTTGGCGTAA
GGTGGGGCGTAGAGCCTTCCCGCCATTGGCGGCGGATAGGGCGTTTACGCGACGGCCTGACGTAGCGGAAGACGCCT
TAGTGGGGGGAAGGTTCTAGAAAAGCGGCGGCAGCGGCTCTAGCGGCAGTAGCAGCAGCGCGGGTCCCGTGCGG
AGGTGCTCCTCGCAGAGTTGTTTCTCCAGCAGCGGCAGTTCTCACTACAGCGCCAGGACGAGTCCGGTTCGTGTTCG
TCCGCGGAGATCTCTCTCATCTCGCTCGGCTGCGGGAAATCGGGCTGAAGCGACTGAGTCCGCGATGGAGGTAACGG
GTTTGAAATCAATGAGTTATTGAAAAGGGCATGGCGAGGCCGTTGGCGCCTCAGTGGAAGTCGGCCAGCCGCCTCCG
TGGGAGAGAGGCAGGAAATCGGACCAATTCAGTAGCAGTGGGCCTTAAGGTTTATGAACGGGGTCTTGAGCGGAGGC
CTGAGCGTACAAACAGCTTCCCCACCCTCAGCCTCCGGCGCCATTTCCCTTCACTGGGGGTGGGGATGGGGAGCT
TTCACATGGCGGACGCTGCCCCGCTGGGGTGAAAGTGGGGCGCGGAGGCGGGACTTCTTATTCCCTTTCTAAAGCAC
GCTGCTTCGGGGGCCACGGCGTCTCCTCGGAAAGCTT
```

Nucleotide sequence of antibody (TRLH) light chain gene cDNA to which an
optimized Kozak has been added upstream of the initiation codon.
<SEQ ID NO: 18>
```
CGCGCCCCGCCGCCACCATGGGTTGGTCTTGTATCATCTTATTTTTAGTTGCTACTGCTACTGGTGTTCATTCTGATA
TACAGATGACCCAAAGCCCATCATCTCTGTCTGCAAGCGTCGGCGACAGGGTGACCATTACCTGTCGCGCAAGCCAAG
ACGTTAATACAGCAGTGGCTTGGTACCAGCAGAAGCCCGGCAAGGCTCCTAAGCTGCTGATCTATAGCGCCTCCTTTC
TTTATTCTGGAGTGCCTTCTCGTTTTTCCGGCTCAAGGTCCGGCAGTCGATTTTCACCCTGACCATTTCCTCCCTCCAGC
CCGAGGATTTTGCCACTTACTACTGTCAGCAGCACTATACCACACCACCTCACATTCGGACAAGGTACAAAGGTAGAAA
TCAAGCGTACGGTGGCTGCCCCATCCGTGTTCATATTCCTCCTAGCGACGAACAACTCAAGTCCGGTACCGCCAGCG
TGGTCTGCCTGTTGAACAATTTTTATCCAAGAGAAGCTAAGGTCCAGTGGAAGGTTGACAACGCCCTTCAGTCCGGAA
ATAGCCAAGAGACGCGTCACCGAACAGGACTCCAAGGACAGTACATACTCACTGAGCTCTACACTGACCCTTTCTAAGG
CCGACTACGAGAAGCACAAGGTCTACGCATGCGAAGTGACCCATCAGGGACTCAGTAGCCCTGTAACAAAGAGTTTTA
ATCGAGGCGAGTGCTAAGCGAT
```

Nucleotide sequence of antibody (TRLH) heavy chain gene cDNA to which an
optimized Kozak has been added upstream of the initiation codon.
<SEQ ID NO: 19>
```
GGCCGCCCGCCGCCACCATGGAATTTGGTTTATCTTGGGTTTTTTTAGTTGCTTTATTAAGAGGTGTTCAATGTGAGG
TGCAGTTGGTCGAATCCGGCGGCGGACTCGTGCAACCAGGCGGAAGTTTGCGGCTGTCCTGCGCAGCCTCTGGTTTTA
ACATCAAAGATACCTATATTCATTGGGTACGCCAGGCTCCTGGAAAGGGGCTTGAGTGGGTGGCTCGAATTTACCCAA
```

SEQUENCE LISTING FREE TEXT

```
CCAATGGCTACACTCGGTATGCCGACAGCGTCAAAGGCAGATTCACCATCTCTGCAGACACATCAAAGAATACCGCTTA
CCTGCAGATGAACTCACTGAGGGCCGAAGATACCGCAGTTTACTACTGCTCCAGGTGGGGGGGGGACGGCTTCTACGCC
ATGGATTACTGGGGACAGGGCACACTCGTGACCGTTAGTAGCGGCTAGCACCAAAGGCCCCTCTGTGTTCCCACTTGCTC
CCTCCAGTAAATCTACCTCCGGAGGAACCGCAGCCCTCGGCTGCCTGGTGAAGGATTACTTCCCAGAGCCCGTCACCGT
CTCTTGGAACTCCGGAGCCTTGACTAGCGGAGTGCACACTTTCCCTGCTGTATTGCAGTCCAGCGGCTTGTATTCACTG
AGTAGCGTCGTCACCGTGCCTTCAAGCAGCCTCGGGACAGACATACATATGTAATGTCAACCATAAGCCATCAAACA
CTAAAGTTGATAAAAAGGTGGAACCTAAGAGTTGCGATAAGACCCATACCTGTCCTCCTTGCCCTGCTCCTGAGCTGCT
GGGAGGCCCTAGCGTGTTTCTGTTCCCCCCCAAGCCCAAAGATACACTGATGATTTCCCGCACACCTGAAGTAACATGT
GTCGTGGTTGATGTGAGTCACGAGGATCCAGAGGTCAAGTTTAATTGGTACGTGGACGGAGTGGAGGTGCACAACGCTA
AGACTAAGCCTCGGGAGGAACAGTACAACAGCACATACCGCGTGGTCAGCGTTTTGACTGTGCTGCATCAAGACTGGCT
CAATGGAAAGGAATACAAGTGCAAGGTCTCTAATAAAGCCCTCCCCGCTCCTATTGAGAAGACTATTTCTAAAGCCAAG
GGCCAGCCTCGCGAACCTCAGGTATATACTTTGCCACCCTCTCGCGAAGAAATGACAAAGAATCAGGTCTCACTCACTT
GCCTCGTCAAAGGGTTTTACCCTTCTGACATCGCTGTCGAATGGGAAAGTAATGGTCAGCAGAAAACAATTACAAGAC
TACTCCACCAGTGCTCGATTCTGATGGAAGTTTCTTTCTCTACAGTAAGCTCACTGTGGACAAATCTCGCTGGCAGCAG
GGTAACGTATTCTCATGCTCCGTGATGCATGAAGCCCTCCACAACCATTACACCCAGAAGAGCCTGTCTCTGAGCCCAG
GCTAACCTGCA
```

The invention claimed is:

1. An expression vector comprising the following (a), (b) and (c):
   (a) a translation-impaired dihydrofolate reductase gene cassette (translation-impaired DHFR gene cassette) comprising a region with altered codons, wherein the altered codons comprise GCA for alanine, CGA for arginine, AAU for asparagine, GAU for aspartic acid, UGU for cysteine, CAA for glutamine, GAA for glutamic acid, GGU for glycine, CAU for histidine, UUA for leucine, AAA for lysine, CCA for proline, UUU for phenylalanine, UCA for serine, ACU for threonine, UAU for tyrosine, and/or GUA for valine, and wherein the region with altered codons accounts for 30% or more of the full length of the DHFR gene from the 5' end of the DHFR gene;
   (b) a gene cassette comprising a cloning site for integration of a foreign gene between a transcriptionally active promoter and a stable polyadenylation signal; and
   (c) a ubiquitously acting chromatin opening element (UCOE),
      wherein the UCOE comprises the nucleotide sequence as shown in SEQ ID NO: 1.

2. The expression vector of claim 1, wherein the translation-impaired DHFR gene cassette of (a) uses a promoter derived from a gene of a non-mammalian cell or a promoter whose enhancer portion has been removed.

3. A method for producing a transformant that produces a foreign gene-derived protein, which comprises integrating a foreign gene into the expression vector of claim 1, and transforming a dihydrofolate reductase gene-deficient host cell with the expression vector.

4. A method for producing a foreign gene-derived protein, which comprises the following (a) to (d):
   (a) integrating a foreign gene into the expression vector of claim 1;
   (b) transforming a dihydrofolate reductase gene-deficient host cell with the expression vector;
   (c) culturing the resultant transformant in a hypoxanthine-thymidine-free medium; and
   (d) collecting the foreign gene-derived protein from the cultured transformant.

5. The method of claim 4, wherein a chemically defined medium (CD medium) or a CD medium supplemented with non-animal-based additives is used for culturing in (c).

6. A method of screening for a transformant that produces a foreign gene-derived protein, which comprises the following (a), (b) and (c):
   (a) integrating a foreign gene into the expression vector of claim 1;
   (b) transforming a dihydrofolate reductase gene-deficient host cell with the expression vector; and
   (c) culturing the resultant transformant in a hypoxanthine-thymidine-free medium.

7. A foreign gene expression vector which has a foreign gene integrated into the expression vector of claim 1.

8. A host cell which has been transformed with the foreign gene expression vector of claim 7.

9. A method for producing a transformant that produces a foreign gene-derived protein, which comprises integrating a foreign gene into the expression vector of claim 2, and transforming a dihydrofolate reductase gene-deficient host cell with the expression vector.

10. A method for producing a foreign gene-derived protein, which comprises the following (a) to (d):
    (a) integrating a foreign gene into the expression vector of claim 2;
    (b) transforming a dihydrofolate reductase gene-deficient host cell with the expression vector;
    (c) culturing the resultant transformant in a hypoxanthine-thymidine-free medium; and
    (d) collecting the foreign gene-derived protein from the cultured transformant.

11. A method of screening for a transformant that produces a foreign gene-derived protein, which comprises the following (a), (b) and (c):
    (a) integrating a foreign gene into the expression vector of claim 2;

(b) transforming a dihydrofolate reductase gene-deficient host cell with the expression vector; and (c) culturing the resultant transformant in a hypoxanthine-thymidine-free medium.

12. A foreign gene expression vector which has a foreign gene integrated into the expression vector of claim 2.

13. The expression vector according to claim 1, wherein the expression vector comprises more than one UCOE.

14. The expression vector according to claim 13, wherein the UCOEs are introduced in such positions that the gene cassette of (b) is sandwiched therebetween.

15. The expression vector according to claim 2, wherein the expression vector comprises more than one UCOE.

16. The expression vector according to claim 15, wherein the UCOEs are introduced in such positions that the gene cassette of (b) is sandwiched therebetween.

17. A method for producing a transformant that produces a foreign gene-derived protein, which comprises integrating a foreign gene into the expression vector of claim 13, and transforming a dihydrofolate reductase gene-deficient host cell with the expression vector.

18. A method for producing a foreign gene-derived protein, which comprises the following (a) to (d):
   (a) integrating a foreign gene into the expression vector of claim 13;
   (b) transforming a dihydrofolate reductase gene-deficient host cell with the expression vector;
   (c) culturing the resultant transformant in a hypoxanthine-thymidine-free medium; and
   (d) collecting the foreign gene-derived protein from the cultured transformant.

19. A method of screening for a transformant that produces a foreign gene-derived protein, which comprises the following (a), (b) and (c):
   (a) integrating a foreign gene into the expression vector of claim 13;
   (b) transforming a dihydrofolate reductase gene-deficient host cell with the expression vector; and
   (c) culturing the resultant transformant in a hypoxanthine-thymidine-free medium.

20. A foreign gene expression vector which has a foreign gene integrated into the expression vector of claim 13.

* * * * *

SEQUENCE LISTING

<160> NUMBER OF SEQ ID NOS: 19

<210> SEQ ID NO 1
<211> LENGTH: 1551
<212> TYPE: DNA
<213> ORGANISM: Homo sapiens

<400> SEQUENCE: 1

| | | | | | |
|---|---|---|---|---|---|
| ggccctccgc | gcctacagct | caagccacat | ccgaaggggg | agggagccgg | gagctgcgcg | 60 |
| cggggccgcc | gggggagggg | gtggcaccgc | ccacgccggg | cggccacgaa | gggcggggca | 120 |
| gcgggcgcgc | gcgcggcggg | gggaggggcc | ggcgccgcgc | ccgctgggaa | ttggggccct | 180 |
| aggggagggg | cggaggcgcc | gacgaccgcg | gcacttaccg | ttcgcggcgt | ggcgccggt | 240 |
| ggtccccaag | gggagggaag | ggggaggcgg | ggcgaggaca | gtgaccggag | tctcctcagc | 300 |
| ggtggctttt | ctgcttggca | gcctcagcgg | ctggcgccaa | aaccggactc | cgcccacttc | 360 |
| ctcgcccgcc | ggtgcgaggg | tgtggaatcc | tccagacgct | gggggagggg | gagttgggag | 420 |
| cttaaaaact | agtaccccctt | tgggaccact | ttcagcagcg | aactctcctg | tacaccaggg | 480 |
| gtcagttcca | cagacgcggg | ccaggggtgg | gtcattgcgg | cgtgaacaat | aatttgacta | 540 |
| gaagttgatt | cgggtgtttc | cggaaggggc | cgagtcaatc | cgccgagttg | gggcacggaa | 600 |
| aacaaaaagg | gaaggctact | aagatttttc | tggcgggggt | tatcattggc | gtaactgcag | 660 |
| ggaccacctc | ccgggttgag | ggggctggat | ctccaggctg | cggattaagc | ccctcccgtc | 720 |
| ggcgttaatt | tcaaactgcg | cgacgtttct | cacctgcctt | cgccaaggca | ggggccggga | 780 |
| ccctattcca | agaggtagta | actagcagga | ctctagcctt | ccgcaattca | ttgagcgcat | 840 |
| ttacggaagt | aacgtcgggt | actgtctctg | gccgcaaggg | tgggaggagt | acgcatttgg | 900 |
| cgtaaggtgg | ggcgtagagc | cttcccgcca | ttggcggcgg | ataggcgtt | tacgcgacgg | 960 |
| cctgacgtag | cggaagacgc | cttagtgggg | gggaaggttc | tagaaaagcg | gcggcagcgg | 1020 |
| ctctagcggc | agtagcagca | gcgccgggtc | ccgtgcggag | gtgctcctcg | cagagttgtt | 1080 |
| tctccagcag | cggcagttct | cactacagcg | ccaggacgag | tccggttcgt | gttcgtccgc | 1140 |
| ggagatctct | ctcatctcgc | tcggctgcgg | gaaatcgggc | tgaagcgact | gagtccgcga | 1200 |
| tggaggtaac | gggtttgaaa | tcaatgagtt | attgaaaagg | gcatggcgag | gccgttggcg | 1260 |
| cctcagtgga | agtcggccag | ccgcctccgt | gggagagagg | caggaaatcg | gaccaattca | 1320 |
| gtagcagtgg | ggcttaaggt | ttatgaacgg | ggtcttgagc | ggaggcctga | gcgtacaaac | 1380 |

```
agcttcccca ccctcagcct cccggcgcca tttcccttca ctgggggtgg gggatgggga    1440
gctttcacat ggcggacgct gccccgctgg ggtgaaagtg gggcgcggag gcgggacttc    1500
ttattcccTT tctaaagcac gctgcttcgg gggccacggc gtctcctcgg a             1551
```

<210> SEQ ID NO 2
<211> LENGTH: 15
<212> TYPE: DNA
<213> ORGANISM: Artificial Sequence
<220> FEATURE:
<223> OTHER INFORMATION: Optimized Kozak sequence

<400> SEQUENCE: 2

```
ccgccgccac catgg                                                     15
```

<210> SEQ ID NO 3
<211> LENGTH: 11327
<212> TYPE: DNA
<213> ORGANISM: Artificial Sequence
<220> FEATURE:
<223> OTHER INFORMATION: pDC62c5-U533

<400> SEQUENCE: 3

```
cgatgtacgg gccagatata cgcgttgaca ttgattattg actagtcgcg ttacataact    60
tacggtaaat ggcccgcctg gctgaccgcc caacgacccc cgcccattga cgtcaataat    120
gacgtatgtt cccatagtaa cgccaatagg gactttccat tgacgtcaat gggtggagta    180
tttacggtaa actgcccact tggcagtaca tcaagtgtat catatgccaa gtccgccccc    240
tattgacgtc aatgacggta aatggcccgc ctggcattat gcccagtaca tgaccttacg    300
ggactttcct acttggcagt acatctacgt attagtcatc gctattacca tggtgatgcg    360
gttttggcag tacaccaatg ggcgtggata gcggtttgac tcacggggat ttccaagtct    420
ccaccccatt gacgtcaatg ggagtttgtt ttggcaccaa aatcaacggg actttccaaa    480
atgtcgtaat aaccccgccc cgttgacgca aatgggcggt aggcgtgtac ggtgggaggt    540
ctatataagc agagctcgtt tagtgaaccg tcagatcctc actctcttcc gcatcgctgt    600
ctgcgagggc cagctgttgg gctcgcggtt gaggacaaac tcttcgcggt ctttccagta    660
ctcttggatc ggaaacccgt cggcctccga acggtactcc gccaccgagg acctgagcg    720 agtccgcatc gaccggatcg aaaacctct cgagaaaggc gtctaaccag tcacagtcgc    780
aaggtaggct gagcaccgtg gcgggcggca gcgggtggcg gtcggggttg tttctggcgg    840
aggtgctgct gatgatgtaa ttaaagtagg cggtcttgag acggcggatg gtcgaggtga    900
ggtgtggcag gcttgagatc cagctgttgg ggtgagtact ccctctcaaa agcgggcatg    960
acttctgcgc taagattgtc agtttccaaa aacgaggagg atttgatatt cacctggccc    1020
gatctggcca tacacttgag tgacaatgac atccactttg cctttctctc cacaggtgtc    1080
cactcccagg tccaaggcgc gccgcgatcg cgcctcgact gtgccttcta gttgccagcc    1140
atctgttgtt tgcccctccc ccgtgccttc cttgaccctg gaaggtgcca ctcccactgt    1200
cctttcctaa taaaatgagg aaattgcatc gcattgtctg agtaggtgtc attctattct    1260
ggggggtggg gtggggcagg acagcaaggg ggaggattgg gaagacaata gcaggcatgc    1320
tggggaggat ctccgcgggg ccctccgcgc ctacagctca gccacatcc gaaggggag     1380 ggagccggga gctgcgcgcg gggccgccgg ggggaggggt ggcaccgccc acgccgggcg    1440
gccacgaagg gcggggcagc gggcgcgcgc gcggcggggg gaggggccgg cgccgcgccc    1500
```

```
gctgggaatt ggggccctag ggggagggcg gaggcgccga cgaccgcggc acttaccgtt    1560
cgcggcgtgg cgcccggtgg tccccaaggg gagggaaggg ggaggcgggg cgaggacagt    1620
gaccggagtc tcctcagcgg tggcttttct gcttggcagc ctcagcggct ggcgccaaaa    1680
ccggactccg cccacttcct cgcccgccgg tgcgagggtg tggaatcctc cagacgctgg    1740
gggaggggga gttgggagct taaaaactag taccccttg ggaccacttt cagcagcgaa    1800
ctctcctgta caccaggggt cagttccaca gacgcgggcc aggggtgggt cattgcggcg    1860
tgaacaataa tttgactaga agttgattcg ggtgtttccg gaagggggccg agtcaatccg    1920 ccgagttggg gcacggaaaa caaaaaggga aggctactaa gattttttctg gcggggggtta    1980 tcattggcgt aactgcaggg accacctccc gggttgaggg ggctggatct ccaggctgcg    2040
gattaagccc ctcccgtcgg cgttaatttc aaactgcgcg acgtttctca cctgccttcg    2100
ccaaggcagg ggccgggacc ctattccaag aggtagtaac tagcaggact ctagccttcc    2160
gcaattcatt gagcgcattt acggaagtaa cgtcgggtac tgtctctggc cgcaagggtg    2220
ggaggagtac gcatttggcg taaggtgggg cgtagagcct tcccgccatt ggcggcggat    2280
agggcgttta cgcgacggcc tgacgtagcg gaagacgcct tagtgggggg gaaggttcta    2340
gaaaagcggc ggcagcggct ctagcggcag tagcagcagc gccgggtccc gtgcggaggt    2400
gctcctcgca gagttgtttc tccagcagcg gcagttctca ctacagcgcc aggacgagtc    2460
cggttcgtgt tcgtccgcgg agatctctct catctcgctc ggctgcggga aatcgggctg    2520
aagcgactga gtccgcgatg gaggtaacgg gtttgaaatc aatgagttat tgaaaagggc    2580
atggcgaggc cgttggcgcc tcagtggaag tcggccagcc gcctccgtgg gagagaggca    2640
ggaaatcgga ccaattcagt agcagtgggg cttaaggttt atgaacgggg tcttgagcgg    2700
aggcctgagc gtacaaacag cttccccacc ctcagcctcc cggcgccatt tcccttcact    2760
gggggtgggg gatggggagc tttcacatgg cggacgctgc cccgctgggg tgaaagtggg    2820
gcgcggaggc gggacttctt attccctttc taaagcacgc tgcttcgggg gccacgcgt    2880 ctcctcggag aattccgatg tacgggccag atatacgcgt tgacattgat tattgactag    2940
tcgcgttaca taacttacgg taaatggccc gcctggctga ccgcccaacg accccccgccc    3000 attgacgtca ataatgacgt atgttcccat agtaacgcca tagggacttt ccattgacg    3060 tcaatgggtg gagtatttac ggtaaactgc ccacttggca gtacatcaag tgtatcatat    3120
gccaagtccg cccctattg acgtcaatga cggtaaatgg cccgcctggc attatgccca    3180
gtacatgacc ttacgggact ttcctacttg gcagtacatc tacgtattag tcatcgctat    3240
taccatggtg atgcggtttt ggcagtacac caatgggcgt ggatagcggt ttgactcacg    3300
gggatttcca agtctccacc ccattgacgt caatgggagt ttgttttggc accaaaatca    3360
acgggacttt ccaaaatgtc gtaataaccc cgccccgttg acgcaaatgg gcggtaggcg    3420
tgtacggtgg gaggtctata taagcagagc tcgtttagtg aaccgtcaga tcctcactct    3480
cttccgcatc gctgtctgcg agggccagct gttgggctcg cggttgagga caaactcttc    3540
gcggtctttc cagtactctt ggatcggaaa cccgtcggcc tccgaacggt actccgccac    3600
cgagggacct gagcgagtcc gcatcgaccg gatcggaaaa cctctcgaga aaggcgtcta    3660
accagtcaca gtcgcaaggt aggctgagca ccgtggcggg cggcagcggg tggcggtcgg    3720
ggttgtttct ggcggaggtg ctgctgatga tgtaattaaa gtaggcgtc ttgagacggc    3780 ggatggtcga ggtgaggtgt ggcaggcttg agatccagct gttggggtga gtactccctc    3840
tcaaaagcgg gcatgacttc tgcgctaaga ttgtcagttt ccaaaaacga ggaggatttg    3900
```

```
atattcacct ggcccgatct ggccatacac ttgagtgaca atgacatcca ctttgccttt    3960
ctctccacag gtgtccactc ccaggtccaa gcggccgccc tgcagggcct cgactgtgcc    4020
ttctagttgc cagccatctg ttgtttgccc ctcccccgtg ccttccttga ccctggaagg    4080
tgccactccc actgtccttt cctaataaaa tgaggaaatt gcatcgcatt gtctgagtag    4140
gtgtcattct attctggggg gtggggtggg gcaggacagc aaggggagg attgggaaga     4200 caatagcagg catgctgggg aggatctccg cggggccctc cgcgcctaca gctcaagcca    4260
catccgaagg gggagggagc cggagctgc gcgcggggcc gccgggggga ggggtggcac     4320
cgcccacgcc gggcggccac gaagggcggg gcagcgggcg cgcgcgcggc gggggaggg    4380 gccggcgccg cgcccgctgg gaattgggc cctaggggga gggcggaggc gccgacgacc     4440
gcggcactta ccgttcgcgg cgtggcgccc ggtggtcccc aagggagggg aaggggagg    4500 cggggcgagg acagtgaccg gagtctcctc agcggtggct tttctgcttg gcagcctcag    4560
cggctggcgc caaaaccgga ctccgcccac ttcctcgccc gccggtgcga gggtgtggaa    4620
tcctccagac gctgggggag ggggagttgg gagcttaaaa actagtaccc ctttgggacc    4680
actttcagca gcgaactctc ctgtacacca ggggtcagtt ccacagacgc gggccagggg    4740
tgggtcattg cggcgtgaac aataatttga ctagaagttg attcgggtgt ttccggaagg    4800
ggccgagtca atccgccgag ttggggcacg gaaaacaaaa agggaaggct actaagattt    4860
ttctggcggg ggttatcatt ggcgtaactg cagggaccac ctcccgggtt gaggggctg     4920 gatctccagg ctgcggatta gcccctcccc gtcggcgtta atttcaaact gcgcgacgtt    4980
tctcacctgc cttcgccaag gcaggggccg ggaccctatt ccaagaggta gtaactagca    5040
ggactctagc cttccgcaat tcattgagcg catttacgga agtaacgtcg ggtactgtct    5100
ctggccgcaa gggtgggagg agtacgcatt tggcgtaagg tggggcgtag agccttcccg    5160
ccattggcgg cggatagggc gtttacgcga cggcctgacg tagcgaagca cgccttagtg    5220 gggggggaagg ttctagaaaa gcggcggcag cggctctagc ggcagtagca gcagcgccgg   5280
gtcccgtgcg gaggtgctcc tcgcagagtt gtttctccag cagcggcagt tctcactaca    5340
gcgccaggac gagtccggtt cgtgttcgtc cgcggagatc tctctcatct cgctcggctg    5400
cgggaaatcg ggctgaagcg actgagtccg cgatggaggt aacgggtttg aaatcaatga    5460
gttattgaaa agggcatggc gaggccgttg gcgcctcagt ggaagtcggc cagccgcctc    5520
cgtgggagag aggcaggaaa tcggaccaat tcagtagcag tggggcttaa ggtttatgaa    5580
cggggtcttg agcggaggcc tgagcgtaca aacagcttcc ccaccctcag cctcccggcg    5640
ccatttccct tcactggggg tggggatgg ggagctttca catggcggac gctgccccgc     5700
tggggtgaaa gtgggcgcg gaggcgggac ttcttattcc ctttctaaag cacgctgctt     5760
cgggggccac ggcgtctcct cggaaccggt tgtggaatgt gtgtcagtta gggtgtggaa    5820
agtccccagg ctccccagca ggcagaagta tgcaaagcat gcatctcaat tagtcagcaa    5880
ccatagtccc gcccctaact ccgcccatcc cgcccctaac tccgcccagt tccgcccatt    5940
ctccgcccca tggctgacta attttttta tttatgcaga ggccgaggcc gcctcggcct    6000
ctgagctatt ccagaagtag tgaggaggct ttttggagg cctaggcttt tgcaaaaaag     6060
ctgcagatgg tacgaccatt aaattgtatt gtagcagtat cacaaaatat gggtattggt    6120
aaaaatggtg atttaccatg gccaccatta cgaaatgaat ttaaatattt tcaacgaatg    6180
actactactt catcagtaga aggtaaacaa aatttagtaa ttatgggtcg aaaaacttgg    6240
```

```
ttttcaattc ctgagaagaa tcgacccttta aaggacagaa ttaatatagt tctcagtaga    6300
gaactcaaag aaccaccacg aggagctcat tttcttgcca aaagtttgga tgatgcctta    6360
agacttattg aacaaccgga attggcaagt aaagtagaca tggtttggat agtcggaggc    6420
agttctgttt accaggaagc catgaatcaa ccaggccacc tcagactctt tgtgacaagg    6480
atcatgcagg aatttgaaag tgacacgttt ttcccagaaa ttgatttggg gaaatataaa    6540
cttctcccag aatacccagg cgtcctctct gaggtccagg aggaaaaagg catcaagtat    6600
aagtttgaag tctacgagaa gaaagactaa agatccgtga cataattgga caaactacct    6660
acagagattt aaagctctaa ggtaaatata aaatttttaa gtgtataatg tgttaaacta    6720
ctgattctaa ttgtttgtgt attttagatt ccaacctatg gaactgatga atgggagcag    6780
tggtggaatg cctttaatga ggaaaacctg ttttgctcag aagaaatgcc atctagtgat    6840
gatgaggcta ctgctgactc tcaacattct actcctccaa aaaagaagag aaaggtagaa    6900
gaccccaagg actttccttc agaattgcta agttttttga gtcatgctgt gtttagtaat    6960
agaactcttg cttgctttgc tatttacacc acaaaggaaa aagctgcact gctatacaag    7020
aaaattatgg aaaaatattc tgtaacctt ataagtaggc ataacagtta taatcataac    7080
atactgtttt ttcttactcc acacaggcat agagtgtctg ctattaataa ctatgctcaa    7140
aaattgtgta cctttagctt tttaatttgt aaagggtta ataaggaata tttgatgtat    7200
agtgccttga ctagagatca taatcagcca taccacattt gtagaggttt tacttgcttt    7260
aaaaaacctc ccacacctcc ccctgaacct gaaacataaa atgaatgcaa ttgttgttgt    7320
taacttgttt attgcagctt ataatggtta caaataaagc aatagcatca caaatttcac    7380
aaataaagca ttttttttcac tgcattctag ttgtggtttg tccaaactca tcaatgtatc    7440
ttatcatgtc tgggccatc gatgccgacg tagcgcctga tgcggtattt tctccttacg    7500
catctgtgcg gtatttcaca ccgcatatgg tgcactctca gtacaatctg ctctgatgcc    7560
gcatagttaa gccagccccg acacccgcca cacccgctg acgcgccctg acgggcttgt    7620
ctgctcccgg catccgctta cagacaagct gtgaccgtct ccgggagctg catgtgtcag    7680
aggttttcac cgtcatcacc gaaacgcgcg agacgaaagg gcctcgtgat acgcctattt    7740
ttataggtta atgtcatgat aataatggtt tcttagacgt caggtggcac tttcgggga    7800 aatgtgcgcg gaacccctat ttgtttattt ttctaaatac attcaaatat gtatccgctc    7860
atgagacaat aaccctgata atgcttcaa taatattgaa aaaggaagag tatgagtatt    7920
caacatttcc gtgtcgccct tattcccttt tttgcggcat tttgccttcc tgttttgct    7980 cacccagaaa cgctggtgaa agtaaaagat gctgaagatc agttgggtgc acgagtgggt    8040
tacatcgaac tggatctcaa cagcggtaag atccttgaga gttttcgccc cgaagaacgt    8100
tttccaatga tgagcacttt taaagttctg ctatgtggcg cggtattatc ccgtattgac    8160
gccgggcaag agcaactcgg tcgccgcata cactattctc agaatgactt ggttgagtac    8220
tcaccagtca cagaaaagca tcttacggat ggcatgacag taagagaatt atgcagtgct    8280
gccataacca tgagtgataa cactgcggcc aacttacttc tgacaacgat cggaggaccg    8340
aaggagctaa ccgcttttt gcacaacatg ggggatcatg taactcgcct tgatcgttgg    8400
gaaccggagc tgaatgaagc cataccaaac gacgagcgtg acaccacgat gcctgtagca    8460
atggcaacaa cgttgcgcaa actattaact ggcgaactac ttactctagc ttcccggcaa    8520
caattaatag actggatgga ggcggataaa gttgcaggac cacttctgcg ctcggccctt    8580
ccggctggct ggtttattgc tgataaatct ggagccggtg agcgtgggtc tcgcggtatc    8640
```

```
attgcagcac tggggccaga tggtaagccc tcccgtatcg tagttatcta cacgacgggg   8700
agtcaggcaa ctatggatga acgaaataga cagatcgctg agataggtgc ctcactgatt   8760
aagcattggt aactgtcaga ccaagtttac tcatatatac tttagattga tttaaaactt   8820 cattttaat ttaaaaggat ctaggtgaag atccttttg ataatctcat gaccaaaatc   8880
ccttaacgtg agttttcgtt ccactgagcg tcagaccccg tagaaaagat caaaggatct   8940
tcttgagatc ctttttttct gcgcgtaatc tgctgcttgc aaacaaaaaa accaccgcta   9000
ccagcggtgg tttgtttgcc ggatcaagag ctaccaactc tttttccgaa ggtaactggc   9060
ttcagcagag cgcagatacc aaatactgtt cttctagtgt agccgtagtt aggccaccac   9120
ttcaagaact ctgtagcacc gcctacatac ctcgctctgc taatcctgtt accagtggct   9180
gctgccagtg gcgataagtc gtgtcttacc gggttggact caagacgata gttaccggat   9240
aaggcgcagc ggtcgggctg aacggggggt tcgtgcacac agcccagctt ggagcgaacg   9300
acctacaccg aactgagata cctacagcgt gagctatgag aaagcgccac gcttcccgaa   9360
gggagaaagg cggacaggta tccggtaagc ggcagggtcg gaacaggaga gcgcacgagg   9420
gagcttccag ggggaaacgc ctggtatctt tatagtcctg tcgggtttcg ccacctctga   9480
cttgagcgtc gatttttgtg atgctcgtca gggggggcgga gcctatggaa aaacgccagc   9540
aacgcggcct ttttacggtt cctggccttt tgctggcctt ttgctcacat gttctttcct   9600
gcgttatccc ctgattctgt ggataaccgt attaccgcct ttgagtgagc tgataccgct   9660
cgccgcagcc gaacgaccga gcgcagcgag tcagtgagcg aggaagcgga agagcgccca   9720
atacgcaaac cgcctctccc cgcgcgttgg ccgattcatt aatgcagctg gccctccgc   9780 gcctacagct caagccacat ccgaagggg agggagccgg gagctgcgcg cggggccgcc   9840
gggggagggg gtggcaccgc ccacgccggg cggccacgaa gggcgggca gcgggcgcgc   9900 gcgcggcggg gggaggggcc ggcgccgcgc ccgctgggaa ttggggccct agggggaggg   9960
cggaggcgcc gacgaccgcg gcacttaccg ttcgcggcgt ggcgcccggt ggtccccaag  10020
gggagggaag ggggaggcgg ggcgaggaca gtgaccggag tctcctcagc ggtggctttt  10080
ctgcttggca gcctcagcgg ctggcgccaa aaccggactc cgcccacttc ctcgcccgcc  10140
ggtgcgaggg tgtggaatcc tccagacgct gggggagggg gagttgggag cttaaaaact  10200
agtacccctt tgggaccact ttcagcagcg aactctcctg tacaccaggg gtcagttcca  10260
cagacgcggg ccaggggtgg gtcattgcgg cgtgaacaat aatttgacta gaagttgatt  10320
cgggtgtttc cggaagggggc cgagtcaatc cgccgagttg gggcacgaaa acaaaaaagg  10380
gaaggctact aagatttttc tggcgggggt tatcattggc gtaactgcag ggaccacctc  10440
ccgggttgag ggggctggat ctccaggctg cggattaagc ccctcccgtc ggcgttaatt  10500
tcaaactgcg cgacgtttct cacctgcctt cgccaaggca ggggccggga ccctattcca  10560
agaggtagta actagcagga ctctagcctt ccgcaattca ttgagcgcat ttacggaagt  10620
aacgtcgggt actgtctctg gccgcaaggg tgggaggagt acgcatttgg cgtaaggtgg  10680
ggcgtagagc cttcccgcca ttggcggcgg atagggcgtt tacgcgacgg cctgacgtag  10740
cggaagacgc cttagtgggg gggaaggttc tagaaaagcg gcgcagcgg ctctagcggc  10800 agtagcagca gcgccgggtc ccgtgcggag gtgctcctcg cagagttgtt tctccagcag  10860
cggcagttct cactacagcg ccaggacgag tccggttcgt gttcgtccgc ggagatctct  10920
ctcatctcgc tcggctgcgg gaaatcgggc tgaagcgact gagtccgcga tggaggtaac  10980
```

-continued

```
gggtttgaaa tcaatgagtt attgaaaagg gcatggcgag gccgttggcg cctcagtgga    11040
agtcggccag ccgcctccgt gggagagagg caggaaatcg gaccaattca gtagcagtgg    11100
ggcttaaggt ttatgaacgg ggtcttgagc ggaggcctga gcgtacaaac agcttcccca    11160
ccctcagcct cccggcgcca tttcccttca ctggggtgg gggatgggga gctttcacat     11220
ggcggacgct gccccgctgg ggtgaaagtg gggcgcggag gcgggacttc ttattccctt    11280
tctaaagcac gctgcttcgg gggccacggc gtctcctcgg aaagctt                  11327
```

<210> SEQ ID NO 4
<211> LENGTH: 736
<212> TYPE: DNA
<213> ORGANISM: Artificial Sequence
<220> FEATURE:
<223> OTHER INFORMATION: Antibody (OMLH) light chain gene cDNA with
      optimized Kozak sequence added upstream of the initiation codon

<400> SEQUENCE: 4

```
cgcgccccgc cgccaccatg ggttggtctt gtatcatctt atttttagtt gctactgcta     60
ctggtgttca ttctgatata cagctcaccc aaagcccatc atctctgtct gcaagcgtcg    120
gcgacagggt gaccattacc tgtcgcgcaa gccaaagcgt tgactacgac ggcgacagct    180
acatgaactg gtaccagcag aagcccggca aggctcctaa gctgctgatc tatgccgcct    240
cctaccttga atctggagtg cctctctcgtt tttccggctc agggtccgga actgatttta    300
ccctgaccat ttcctccctc cagcccgagg attttgccac ttactactgt cagcagtccc    360
acgaggaccc atatacattc ggacaaggta caaaggtaga aatcaagcgt acggtggctg    420
ccccatccgt gttcatattt cctcctagcg acgaacaact caagtccggt accgccagcg    480
tggtctgcct gttgaacaat ttttatccaa gagaagctaa ggtccagtgg aaggttgaca    540
acgcccttca gtccggaaat agccaagaga gcgtcaccga acaggactcc aaggacagta    600
catactcact gagctctaca ctgacccttt ctaaggccga ctacgagaag cacaaggtct    660
acgcatgcga agtgacccat cagggactca gtagccctgt aacaaagagt tttaatcgag    720
gcgagtgcta agcgat                                                    736
```

<210> SEQ ID NO 5
<211> LENGTH: 1436
<212> TYPE: DNA
<213> ORGANISM: Artificial Sequence
<220> FEATURE:
<223> OTHER INFORMATION: Antibody (OMLH) heavy chain gene cDNA with
      optimized Kozak sequence added upstream of the initiation codon

<400> SEQUENCE: 5

```
ggccgccccgc cgccaccatg gaatttggtt tatcttgggt ttttttagtt gctttattaa     60
gaggtgttca atgtgaggtg cagttggtcg aatccggcgg cggactcgtg caaccaggcg    120
gaagtttgcg gctgtcctgc gcagtgtctg gttacagcat cacctccggg tatagctgga    180
actggatccg ccaggctcct ggaaagggc ttgagtgggg gcttccatt acctacgacg     240 gctccactaa ctataacccg agcgtcaaag cagaatcac catctctcgg gacgactcaa    300
agaatacctt ctacctgcag atgaactcac tgagggccga gataccgca gtttactact    360 gcgccagggg gtcccactat ttcggccact ggcacttcgc cgtgtgggga cagggcacac    420
tcgtgaccgt tagtagcgct agcaccaaag ccccctctgt gttcccactt gctccctcca    480
gtaaatctac ctccggagga accgcagccc tcggctgcct ggtgaaggat tacttcccag    540
agcccgtcac cgtctcttgg aactccggag ccttgactag cggagtgcac actttccctg    600
```

| | |
|---|---|
| ctgtattgca gtccagcggc ttgtattcac tgagtagcgt cgtcaccgtg ccttcaagca | 660 |
| gcctcgggac acagacatac atatgtaatg tcaaccataa gccatcaaac actaaagttg | 720 |
| ataaaaaggt ggaacctaag agttgcgata gacccatac ctgtcctcct tgccctgctc | 780 |
| ctgagctgct gggaggccct agcgtgtttc tgttccccc caagcccaaa gatacactga | 840 |
| tgatttcccg cacacctgaa gtaacatgtg tcgtggttga tgtgagtcac gaggatccag | 900 |
| aggtcaagtt taattggtac gtggacggag tggaggtgca caacgctaag actaagcctc | 960 |
| gggaggaaca gtacaacagc acataccgcg tggtcagcgt tttgactgtg ctgcatcaag | 1020 |
| actggctcaa tggaaaggaa tacaagtgca aggtctctaa taaagccctc cccgctccta | 1080 |
| ttgagaagac tatttctaaa gccaagggcc agcctcgcga acctcaggta tatactttgc | 1140 |
| caccctctcg cgaagaaatg acaaagaatc aggtctcact cacttgcctc gtcaaagggt | 1200 |
| tttacccttc tgacatcgct gtcgaatggg aaagtaatgg tcagccagaa aacaattaca | 1260 |
| agactactcc accagtgctc gattctgatg gaagtttctt tctctacagt aagctcactg | 1320 |
| tggacaaatc tcgctggcag cagggtaacg tattctcatg ctccgtgatg catgaagccc | 1380 |
| tccacaacca ttacacccag aagagcctgt ctctgagccc aggcaagtaa cctgca | 1436 |

<210> SEQ ID NO 6
<211> LENGTH: 7317
<212> TYPE: DNA
<213> ORGANISM: Artificial Sequence
<220> FEATURE:
<223> OTHER INFORMATION: pDC61

<400> SEQUENCE: 6

| | |
|---|---|
| cgatgtacgg gccagatata cgcgttgaca ttgattattg actagttatt aatagtaatc | 60 |
| aattacgggg tcattagttc atagcccata tatggagttc cgcgttacat aacttacggt | 120 |
| aaatggcccg cctggctgac cgcccaacga ccccgccca ttgacgtcaa taatgacgta | 180 |
| tgttcccata gtaacgccaa tagggacttt ccattgacgt caatgggtgg agtatttacg | 240 |
| gtaaactgcc cacttggcag tacatcaagt gtatcatatg ccaagtacgc cccctattga | 300 |
| cgtcaatgac ggtaaatggc ccgcctggca ttatgcccag tacatgacct tatgggactt | 360 |
| tcctacttgg cagtacatct acgtattagt catcgctatt accatggtga tgcggttttg | 420 |
| gcagtacatc aatgggcgtg atagcggtt tgactcacgg ggatttccaa gtctccaccc | 480 |
| cattgacgtc aatgggagtt tgttttggca ccaaaatcaa cgggactttc caaaatgtcg | 540 |
| taacaactcc gccccattga cgcaaatggg cggtaggcgt gtacggtggg aggtctatat | 600 |
| aagcagagct ctctggctaa ctagagaacc cactgttaac tggcttatcg aaattgtcga | 660 |
| ggagaacttc agggtgagtt tggggacccct tgattgttct ttcttttcg ctattgtaaa | 720 |
| attcatgtta tatggagggg gcaaagtttt cagggtgttg tttagaatgg aagatgtcc | 780 |
| cttgtatcac catggaccct catgataatt ttgtttcttt cactttctac tctgttgaca | 840 |
| accattgtct cctcttattt tcttttcatt ttctgtaact ttttcgttaa actttagctt | 900 |
| gcatttgtaa cgaattttta aattcacttt tgtttatttg tcagattgta agtactttct | 960 |
| ctaatcactt ttttttcaag gcaatcaggg tatattatat tgtacttcag cacagtttta | 1020 |
| gagaacaatt gttataatta aatgataagg tagaatattt ctgcatataa attctggctg | 1080 |
| gcgtggaaat attcttattg gtagaaacaa ctacatcctg gtcatcatcc tgcctttctc | 1140 |
| tttatggtta caatgatata cactgtttga gatgaggata aatactctg agtccaaacc | 1200 |

```
gggcccctct gctaaccatg ttcatgcctt cttcttttc ctacagctcc tgggcaacgt    1260
gctggcggcc gccccggggc ctcgactgtg ccttctagtt gccagccatc tgttgtttgc    1320
ccctcccccg tgccttcctt gaccctggaa ggtgccactc ccactgtcct ttcctaataa    1380
aatgaggaaa ttgcatcgca ttgtctgagt aggtgtcatt ctattctggg gggtggggtg    1440
gggcaggaca gcaaggggga ggattgggaa gacaatagca ggcatgctgg ggactcgagc    1500
gatgtacggg ccagatatac gcgttgacat tgattattga ctagttatta atagtaatca    1560 attacgggt cattagttca tagcccatat atggagttcc gcgttacata acttacggta    1620
aatggcccgc ctggctgacc gcccaacgac ccccgcccat tgacgtcaat aatgacgtat    1680
gttcccatag taacgccaat agggactttc cattgacgtc aatgggtgga gtatttacgg    1740
taaactgccc acttggcagt acatcaagtg tatcatatgc caagtacgcc ccctattgac    1800
gtcaatgacg gtaaatggcc cgcctggcat tatgcccagt acatgacctt atgggacttt    1860
cctacttggc agtacatcta cgtattagtc atcgctatta ccatggtgat gcggttttgg    1920
cagtacatca atgggcgtgg atagcggttt gactcacggg gatttccaag tctccacccc    1980
attgacgtca atgggagttt gttttggcac caaaatcaac gggactttcc aaaatgtcgt    2040
aacaactccg ccccattgac gcaaatgggc ggtaggcgtg tacggtggga ggtctatata    2100
agcagagctc tctggctaac tagagaaccc actgttaact ggcttatcga aattgtcgag    2160
gagaacttca gggtgagttt ggggacccct gattgttctt tctttttcgc tattgtaaaa    2220
ttcatgttat atggaggggg caaagttttc agggtgttgt ttagaatggg aagatgtccc    2280
ttgtatcacc atggaccctc atgataattt tgtttctttc actttctact ctgttgacaa    2340
ccattgtctc ctcttattt cttttcattt tctgtaactt tttcgttaaa ctttagcttg    2400
catttgtaac gaattttta attcactttt gtttatttgt cagattgtaa gtactttctc    2460
taatcacttt tttttcaagg caatcagggt atattatatt gtacttcagc acagttttag    2520
agaacaattg ttataattaa atgataaggt agaatatttc tgcatataaa ttctggctgg    2580
cgtggaaata ttcttattgg tagaaacaac tacatcctgg tcatcatcct gcctttctct    2640
ttatggttac aatgatatac actgtttgag atgaggataa aatactctga gtccaaaccg    2700
ggcccctctg ctaaccatgt tcatgccttc ttcttttcc tacagctcct gggcaacgtg    2760
ctggcgcgcc tctagagcct cgactgtgcc ttctagttgc cagccatctg ttgtttgccc    2820
ctcccccgtg ccttccttga ccctggaagg tgccactccc actgtccttt cctaataaaa    2880
tgaggaaatt gcatcgcatt gtctgagtag gtgtcattct attctggggg gtggggtggg    2940
gcaggacagc aagggggagg attgggaaga caatagcagg catgctgggg aggatctccg    3000
cggtgtggaa tgtgtgtcag ttagggtgtg gaaagtcccc aggctcccca gcaggcagaa    3060
gtatgcaaag catgcatctc aattagtcag caaccatagt cccgccccta actccgccca    3120
tcccgcccct aactccgccc agttccgccc attctccgcc ccatggctga ctaattttt    3180 ttatttatgc agaggccgag gccgcctcgg cctctgagct attccagaag tagtgaggag    3240
gcttttttgg aggcctaggc ttttgcaaaa agctgcaga tggtacgacc attaaattgt    3300
attgtagcag tatcacaaaa tatgggtatt ggtaaaaatg gtgatttacc atggccacca    3360
ttacgaaatg aatttaaata ttttcaacga atgactacta cttcatcagt agaaggtaaa    3420
caaaatttag taattatggg tcgaaaaact tggttttcaa ttcctgagaa gaatcgacct    3480
ttaaaggaca gaattaatat agttctcagt agagaactca aagaaccacc acgaggagct    3540
cattttcttg ccaaaagttt ggatgatgcc ttaagactta ttgaacaacc ggaattggca    3600
```

```
agtaaagtag acatggtttg gatagtcgga ggcagttctg tttaccagga agccatgaat    3660
caaccaggcc acctcagact ctttgtgaca aggatcatgc aggaatttga aagtgacacg    3720
tttttcccag aaattgattt ggggaaatat aaacttctcc cagaataccc aggcgtcctc    3780
tctgaggtcc aggaggaaaa aggcatcaag tataagtttg aagtctacga gaagaaagac    3840
taaagatccg tgacataatt ggacaaacta cctacagaga tttaaagctc taaggtaaat    3900
ataaaatttt taagtgtata atgtgttaaa ctactgattc taattgtttg tgtattttag    3960
attccaacct atggaactga tgaatgggag cagtggtgga atgcctttaa tgaggaaaac    4020
ctgttttgct cagaagaaat gccatctagt gatgatgagg ctactgctga ctctcaacat    4080
tctactcctc caaaaagaa gagaaaggta gaagacccca aggactttcc ttcagaattg    4140
ctaagttttt tgagtcatgc tgtgtttagt aatagaactc ttgcttgctt tgctatttac    4200
accacaaagg aaaagctgc actgctatac aagaaaatta tggaaaaata ttctgtaacc    4260
tttataagta ggcataacag ttataatcat aacatactgt ttttcttac tccacacagg    4320 catagagtgt ctgctattaa taactatgct caaaaattgt gtacctttag cttttttaatt    4380 tgtaaagggg ttaataagga atatttgatg tatagtgcct tgactagaga tcataatcag    4440
ccataccaca tttgtagagg ttttacttgc tttaaaaaac ctcccacacc tcccctgaa    4500 cctgaaacat aaaatgaatg caattgttgt tgttaacttg tttattgcag cttataatgg    4560
ttacaaataa agcaatagca tcacaaattt cacaaataaa gcattttttt cactgcattc    4620
tagttgtggt ttgtccaaac tcatcaatgt atcttatcat gtctgggccc atcgatgaat    4680
tcactggccg tcgttttaca acgtcgtgac tgggaaaacc ctggcgttac ccaacttaat    4740
cgccttgcag cacatcccc tttcgccagc tggcgtaata gcgaagaggc ccgcaccgat    4800
cgcccttccc aacagttgcg cagcctgaat ggcgaatggc gcctgatgcg gtattttctc    4860
cttacgcatc tgtgcggtat ttcacaccgc atatggtgca ctctcagtac aatctgctct    4920
gatgccgcat agttaagcca gccccgacac ccgccaacac ccgctgacgc gccctgacgg    4980
gcttgtctgc tcccggcatc cgcttacaga caagctgtga ccgtctccgg gagctgcatg    5040
tgtcagaggt tttcaccgtc atcaccgaaa cgcgcgagac gaaagggcct cgtgatacgc    5100
ctatttttat aggttaatgt catgataata atggtttctt agacgtcagg tggcactttt    5160
cggggaaatg tgcgcggaac ccctatttgt ttatttttct aaatacattc aaatatgtat    5220
ccgctcatga gacaataacc ctgataaatg cttcaataat attgaaaaag gaagagtatg    5280
agtattcaac atttccgtgt cgcccttatt ccctttttg cggcattttg ccttcctgtt    5340
tttgctcacc cagaaacgct ggtgaaagta aaagatgctg aagatcagtt gggtgcacga    5400
gtgggttaca tcgaactgga tctcaacagc ggtaagatcc ttgagagttt cgccccgaa    5460 gaacgttttc caatgatgag cacttttaaa gttctgctat gtggcgcggt attatcccgt    5520
attgacgccg ggcaagagca actcggtcgc cgcatacact attctcagaa tgacttggtt    5580
gagtactcac cagtcacaga aaagcatctt acggatggca tgacagtaag agaattatgc    5640
agtgctgcca taaccatgag tgataacact gcggccaact tacttctgac aacgatcgga    5700
ggaccgaagg agctaaccgc ttttttgcac aacatggggg atcatgtaac tcgccttgat    5760
cgttgggaac cggagctgaa tgaagccata ccaaacgacg agcgtgacac cacgatgcct    5820
gtagcaatgg caacaacgtt gcgcaaacta ttaactggcg aactacttac tctagcttcc    5880
cggcaacaat taatagactg gatggaggcg gataaagttg caggaccact tctgcgctcg    5940
```

-continued

```
gcccttccgg ctggctggtt tattgctgat aaatctggag ccggtgagcg tgggtctcgc    6000
ggtatcattg cagcactggg gccagatggt aagccctccc gtatcgtagt tatctacacg    6060
acggggagtc aggcaactat ggatgaacga atagacaga tcgctgagat aggtgcctca     6120
ctgattaagc attggtaact gtcagaccaa gtttactcat atatacttta gattgattta    6180
aaacttcatt tttaatttaa aaggatctag gtgaagatcc ttttttgataa tctcatgacc   6240
aaaatccctt aacgtgagtt ttcgttccac tgagcgtcag accccgtaga aaagatcaaa    6300
ggatcttctt gagatccttt ttttctgcgc gtaatctgct gcttgcaaac aaaaaaacca    6360
ccgctaccag cggtggtttg tttgccggat caagagctac caactctttt tccgaaggta    6420
actggcttca gcagagcgca gataccaaat actgttcttc tagtgtagcc gtagttaggc    6480
caccacttca agaactctgt agcaccgcct acatacctcg ctctgctaat cctgttacca    6540
gtggctgctg ccagtggcga taagtcgtgt cttaccgggt tggactcaag acgatagtta    6600
ccggataagg cgcagcggtc gggctgaacg ggggggttcgt gcacacagcc cagcttggag    6660
cgaacgacct acaccgaact gagatacta cagcgtgagc tatgagaaag cgccacgctt      6720
cccgaaggga gaaaggcgga caggtatccg gtaagcggca gggtcggaac aggagagcgc    6780
acgagggagc ttccaggggg aaacgcctgg tatctttata gtcctgtcgg gtttcgccac    6840
ctctgacttg agcgtcgatt tttgtgatgc tcgtcagggg gcggagcct atggaaaaac      6900
gccagcaacg cggccttttt acggttcctg gccttttgct ggccttttgc tcacatgttc    6960
tttcctgcgt tatcccctga ttctgtggat aaccgtatta ccgcctttga gtgagctgat    7020
accgctcgcc gcagccgaac gaccgagcgc agcgagtcag tgagcgagga agcggaagag    7080
cgcccaatac gcaaaccgcc tctccccgcg cgttggccga ttcattaatg cagctggcac    7140
gacaggtttc ccgactggaa agcgggcagt gagcgcaacg caattaatgt gagttagctc    7200
actcattagg caccccaggc tttacacttt atgcttccgg ctcgtatgtt gtgtggaatt    7260
gtgagcggat aacaatttca cacaggaaac agctatgacc atgattacgc caagctt       7317
```

<210> SEQ ID NO 7
<211> LENGTH: 2635
<212> TYPE: DNA
<213> ORGANISM: Artificial Sequence
<220> FEATURE:
<223> OTHER INFORMATION: Sequence in pDC61, which is substitued for the
      sequence from No. 3182 to No. 5843 in pDC6

<400> SEQUENCE: 7

```
aattcactgg ccgtcgtttt acaacgtcgt gactgggaaa accctggcgt tacccaactt      60
aatcgccttg cagcacatcc cccttttcgcc agctggcgta atagcgaaga ggcccgcacc    120
gatcgccctt cccaacagtt gcgcagcctg aatggcgaat ggcgcctgat gcggtatttt     180
ctccttacgc atctgtgcgg tatttcacac cgcatatggt gcactctcag tacaatctgc    240
tctgatgccg catagttaag ccagccccga caccgccaa cacccgctga gcgccctga      300
cgggcttgtc tgctcccggc atccgcttac agacaagctg tgaccgtctc cgggagctgc    360
atgtgtcaga ggttttcacc gtcatcaccg aaacgcgcga gacgaaaggg cctcgtgata    420
cgcctatttt tataggttaa tgtcatgata ataatggttt cttagacgtc aggtggcact    480
tttcggggaa atgtgcgcgg aacccctatt tgtttatttt tctaaataca ttcaaatatg    540
tatccgctca tgagacaata accctgataa atgcttcaat aatattgaaa aaggaagagt    600
atgagtattc aacatttccg tgtcgccctt attcccttttt ttgcggcatt ttgccttcct    660
```

| | |
|---|---|
| gtttttgctc acccagaaac gctggtgaaa gtaaagatg ctgaagatca gttgggtgca | 720 |
| cgagtgggtt acatcgaact ggatctcaac agcggtaaga tccttgagag ttttcgcccc | 780 |
| gaagaacgtt ttccaatgat gagcactttt aaagttctgc tatgtggcgc ggtattatcc | 840 |
| cgtattgacg ccgggcaaga gcaactcggt cgccgcatac actattctca gaatgacttg | 900 |
| gttgagtact caccagtcac agaaaagcat cttacggatg gcatgacagt aagagaatta | 960 |
| tgcagtgctg ccataaccat gagtgataac actgcggcca acttacttct gacaacgatc | 1020 |
| ggaggaccga aggagctaac cgcttttttg cacaacatgg gggatcatgt aactcgcctt | 1080 |
| gatcgttggg aaccggagct gaatgaagcc ataccaaacg acgagcgtga caccacgatg | 1140 |
| cctgtagcaa tggcaacaac gttgcgcaaa ctattaactg gcgaactact tactctagct | 1200 |
| tcccggcaac aattaataga ctggatggag gcggataaag ttgcaggacc acttctgcgc | 1260 |
| tcggcccttc cggctggctg gtttattgct gataaatctg gagccggtga gcgtgggtct | 1320 |
| cgcggtatca ttgcagcact ggggccagat ggtaagccct cccgtatcgt agttatctac | 1380 |
| acgacgggga gtcaggcaac tatggatgaa cgaaatagac agatcgctga ataggtgcc | 1440 |
| tcactgatta agcattggta actgtcagac caagtttact catatatact ttagattgat | 1500 |
| ttaaaacttc attttaatt taaaggatc taggtgaaga tcctttttga taatctcatg | 1560 |
| accaaaatcc cttaacgtga gttttcgttc cactgagcgt cagaccccgt agaaaagatc | 1620 |
| aaaggatctt cttgagatcc ttttttctg cgcgtaatct gctgcttgca acaaaaaaa | 1680 |
| ccaccgctac cagcggtggt ttgtttgccg gatcaagagc taccaactct ttttccgaag | 1740 |
| gtaactggct tcagcagagc gcagatacca aatactgttc ttctagtgta gccgtagtta | 1800 |
| ggccaccact tcaagaactc tgtagcaccg cctacatacc tcgctctgct aatcctgtta | 1860 |
| ccagtggctg ctgccagtgg cgataagtcg tgtcttaccg ggttggactc aagacgatag | 1920 |
| ttaccggata aggcgcagcg tcgggctga cgggggggtt cgtgcacaca gcccagcttg | 1980 |
| gagcgaacga cctacaccga actgagatac ctacagcgtg agctatgaga aagcgccacg | 2040 |
| cttcccgaag ggagaaaggc ggacaggtat ccggtaagcg gcagggtcgg aacaggagag | 2100 |
| cgcacgaggg agcttccagg gggaaacgcc tggtatcttt atagtcctgt cgggtttcgc | 2160 |
| cacctctgac ttgagcgtcg atttttgtga tgctcgtcag ggggggcggag cctatggaaa | 2220 |
| aacgccagca acgcggcctt tttacggttc ctggccttt gctggccttt tgctcacatg | 2280 |
| ttctttcctg cgttatcccc tgattctgtg ataaccgta ttaccgcctt tgagtgagct | 2340 |
| gataccgctc gccgcagccg aacgaccgag cgcagcgagt cagtgagcga ggaagcggaa | 2400 |
| gagcgcccaa tacgcaaacc gcctctcccc gcgcgttggc cgattcatta atgcagctgg | 2460 |
| cacgacaggt ttcccgactg gaaagcgggc agtgagcgca acgcaattaa tgtgagttag | 2520 |
| ctcactcatt aggcaccca ggctttacac tttatgcttc cggctcgtat gttgtgtgga | 2580 |
| attgtgagcg gataacaatt tcacacagga aacagctatg accatgatta cgcca | 2635 |

<210> SEQ ID NO 8
<211> LENGTH: 725
<212> TYPE: DNA
<213> ORGANISM: Artificial Sequence
<220> FEATURE:
<223> OTHER INFORMATION: cDNA encoding human omalizumab antibody light chain (OML) to be substitued for the sequence from No. 1267 to No. 1273 in pDC61

<400> SEQUENCE: 8

| | |
|---|---|
| ggccgccacc atgggttggt cttgtatcat cttatttta gttgctactg ctactggtgt | 60 |

```
tcattctgat atacagctca cccaaagccc atcatctctg tctgcaagcg tcggcgacag    120
ggtgaccatt acctgtcgcg caagccaaag cgttgactac gacggcgaca gctacatgaa    180
ctggtaccag cagaagcccg gcaaggctcc taagctgctg atctatgccg cctcctacct    240
tgaatctgga gtgcctctct gttttccgg ctcagggtcc ggaactgatt ttaccctgac     300
catttcctcc ctccagcccg aggattttgc cacttactac tgtcagcagt cccacgagga    360
cccatataca ttcggacaag gtacaaaggt agaaatcaag cgtacggtgg ctgccccatc    420
cgtgttcata tttcctccta gcgacgaaca actcaagtcc ggtaccgcca gcgtggtctg    480
cctgttgaac aattttttatc aagagaagc taaggtccag tggaaggttg acaacgccct    540
tcagtccgga aatagccaag agagcgtcac cgaacaggac tccaaggaca gtacatactc    600
actgagctct acactgaccc tttctaaggc cgactacgag aagcacaagg tctacgcatg    660
cgaagtgacc catcagggac tcagtagccc tgtaacaaag agttttaatc gaggcgagtg    720
ctaac                                                                725

<210> SEQ ID NO 9
<211> LENGTH: 1423
<212> TYPE: DNA
<213> ORGANISM: Artificial Sequence
<220> FEATURE:
<223> OTHER INFORMATION: cDNA encoding human omalizumab antibody heavy
      chain (OMH) to be substitued for the sequence from No. 2765 to No.
      2771 in pDC61

<400> SEQUENCE: 9
cgcgccacca tggaatttgg tttatcttgg gttttttag ttgctttatt aagaggtgtt     60
caatgtgagg tgcagttggt cgaatccggc ggcggactcg tgcaaccagg cggaagtttg   120
cggctgtcct gcgcagtgtc tggttacagc atcacctccg ggtatagctg gaactggatc   180
cgccaggctc ctggaaaggg gcttgagtgg gtggcttcca ttacctacga cggctccact   240
aactataacc cgagcgtcaa aggcagaatc accatctctc gggacgactc aaagaatacc   300
ttctacctgc agatgaactc actgagggcc gaagataccg cagtttacta ctgcgccagg   360
gggtcccact atttcggcca ctggcacttc gccgtgtggg gacagggcac actcgtgacc   420
gttagtagcg ctagcaccaa aggcccctct gtgttcccac ttgctccctc cagtaaatct   480
acctccggag gaaccgcagc cctcggctgc ctggtgaagg attactttccc agagcccgtc   540 accgtctctt ggaactccgg agccttgact agcggagtgc acactttccc tgctgtattg   600
cagtccagcg gcttgtattc actgagtagc gtcgtcaccg tgccttcaag cagcctcggg   660
acacagacat acatatgtaa tgtcaaccat aagccatcaa acactaaagt tgataaaaag   720
gtggaaccta gagttgcga taagacccat acctgtcctc cttgccctgc tcctgagctg     780
ctgggaggcc ctagcgtgtt tctgttcccc ccaagccca agatacact gatgatttcc    840 cgcacacctg aagtaacatg tgtcgtggtt gatgtgagtc acgaggatcc agaggtcaag    900
tttaattggt acgtggacgg agtggaggtg cacaacgcta agactaagcc tcgggaggaa    960
cagtacaaca gcacataccg cgtggtcagc gttttgactg tgctgcatca agactggctc   1020
aatggaaagg aatacaagtg caaggtctct aataaagccc tccccgctcc tattgagaag   1080
actatttcta aagccaaggg ccagcctcgc gaacctcagg tatatacttt gccaccctct   1140
cgcgaagaaa tgacaaagaa tcaggtctca ctcacttgcc tcgtcaaagg gttttaccct   1200
tctgacatcg ctgtcgaatg ggaaagtaat ggtcagccag aaaacaatta caagactact   1260
```

```
ccaccagtgc tcgattctga tggaagtttc tttctctaca gtaagctcac tgtggacaaa      1320
tctcgctggc agcagggtaa cgtattctca tgctccgtga tgcatgaagc cctccacaac      1380 cattcaccc agaagagcct gtctctgagc ccaggcaagt aat                         1423

<210> SEQ ID NO 10
<211> LENGTH: 10686
<212> TYPE: DNA
<213> ORGANISM: Artificial Sequence
<220> FEATURE:
<223> OTHER INFORMATION: pNC32c-U533

<400> SEQUENCE: 10
cgatgtacgg gccagatata cgcgttgaca ttgattattg actagttatt aatagtaatc        60
aattacgggg tcattagttc atagcccata tatggagttc cgcgttacat aacttacggt       120
aaatggcccg cctggctgac cgcccaacga ccccccgccca ttgacgtcaa taatgacgta      180
tgttcccata gtaacgccaa tagggacttt ccattgacgt caatgggtgg agtatttacg      240
gtaaactgcc cacttggcag tacatcaagt gtatcatatg ccaagtacgc cccctattga      300
cgtcaatgac ggtaaatggc ccgcctggca ttatgcccag tacatgacct tatgggactt      360
tcctacttgg cagtacatct acgtattagt catcgctatt accatggtga tgcggttttg      420
gcagtacatc aatgggcgtg gatagcggtt tgactcacgg ggatttccaa gtctccaccc      480
cattgacgtc aatgggagtt gttttggca ccaaaatcaa cgggactttc caaaatgtcg      540
taacaactcc gccccattga cgcaaatggg cggtaggcgt gtacggtggg aggtctatat      600
aagcagagct ctctggctaa ctagagaacc cactgttaac tggcttatcg aaattggcgc      660
gccgcgatcg ccctcccaca cctcccctg aacctgaaac ataaaatgaa tgcaattgtt      720
gttgttaact tgtttattgc agcttataat ggttacaaat aaagcaatag catcacaaat      780
ttcacaaata aagcattttt ttcactgcat tctagttgtg gtttgtccaa actcatcaat      840
gtatcttatc atgtctggat ctccgcgcc ctccgcgcct acagctcaag ccacatccga      900
agggggaggg agccgggagc tgcgcgcggg gccgccgggg ggaggggtgg caccgcccac      960
gccgggcggc cacgaagggc ggggcagcgg gcgcgcgcgc ggcgggggga ggggccggcg     1020
ccgcgcccgc tgggaattgg ggccctaggg ggagggcgga ggcgccgacg accgcggcac     1080
ttaccgttcg cggcgtggcg cccggtggtc cccaagggga gggaagggg aggcggggcg     1140 aggacagtga ccggagtctc ctcagcggtg ctttcctgc ttggcagcct cagcggctgg     1200
cgccaaaacc ggactccgcc cacttcctcg cccgccggtg cgagggtgtg gaatcctcca     1260
gacgctgggg gaggggagt tgggagctta aaaactagta cccctttggg accactttca     1320
gcagcgaact ctcctgtaca ccaggggtca gttccacaga cgcggcccag gggtgggtca     1380
ttgcggcgtg aacaataatt tgactagaag ttgattcggg tgtttccgga aggggccgag     1440
tcaatccgcc gagttgggc acggaaaaca aaaaggaag gctactaaga ttttctggc      1500 gggggttatc attggcgtaa ctgcagggac cactcccgg gttgagggg ctggatctcc     1560 aggctgcgga ttaagcccct cccgtcggcg ttaatttcaa actgcgcgac gtttctcacc     1620
tgccttcgcc aaggcagggg ccgggaccct attccaagag gtagtaacta gcaggactct     1680
agccttccgc aattcattga gcgcatttac ggaagtaacg tcgggtactg tctctggccg     1740
caagggtggg aggagtacgc atttggcgta aggtgggggcg tagagccttc cgccattgg      1800 cggcggatag ggcgtttacg cgacggcctg acgtagcgga agacgcctta gtgggggga     1860 aggttctaga aaagcggcgg cagcggctct agcggcagta gcagcagcgc cgggtcccgt     1920
```

```
gcggaggtgc tcctcgcaga gttgtttctc cagcagcggc agttctcact acagcgccag    1980
gacgagtccg gttcgtgttc gtccgcggag atctctctca tctcgctcgg ctgcgggaaa    2040
tcgggctgaa gcgactgagt ccgcgatgga ggtaacgggt ttgaaatcaa tgagttattg    2100 aaagggcat ggcgaggccg ttggcgcctc agtggaagtc ggccagccgc ctccgtggga     2160
gagaggcagg aaatcggacc aattcagtag cagtggggct taaggtttat gaacggggtc    2220
ttgagcggag gcctgagcgt acaaacagct tccccaccct cagcctcccg cgccatttc     2280 ccttcactgg gggtggggga tggggagctt tcacatggcg gacgctgccc cgctggggtg    2340
aaagtggggc gcggaggcgg gacttcttat tcccttcta aagcacgctg cttcgggggc     2400
cacggcgtct cctcggagaa ttccgatgta cgggccagat atacgcgttg acattgatta    2460
ttgactagtt attaatagta atcaattacg gggtcattag ttcatagccc atatatggag    2520
ttccgcgtta cataacttac ggtaaatggc ccgcctggct gaccgcccaa cgaccccgc     2580 ccattgacgt caataatgac gtatgttccc atagtaacgc caatagggac tttccattga    2640
cgtcaatggg tggagtattt acggtaaact gcccacttgg cagtacatca agtgtatcat    2700
atgccaagta cgccccctat tgacgtcaat gacggtaaat ggcccgcctg cattatgcc    2760 cagtacatga ccttatggga ctttcctact tggcagtaca tctacgtatt agtcatcgct    2820
attaccatgg tgatgcggtt ttggcagtac atcaatgggc gtggatagcg gtttgactca    2880
cggggatttc caagtctcca ccccattgac gtcaatggga gtttgtttg gcaccaaaat    2940 caacgggact ttccaaaatg tcgtaacaac tccgccccat tgacgcaaat gggcggtagg    3000
cgtgtacggt gggaggtcta tataagcaga gctctctggc taactagaga acccactgtt    3060
aactggctta tcgaaattgc ggccgcctg caggcctccc acacctcccc ctgaacctga    3120
aacataaaat gaatgcaatt gttgttgtta acttgtttat tgcagcttat aatggttaca    3180
aataaagcaa tagcatcaca aatttcacaa ataaagcatt ttttcactg cattctagtt    3240 gtggtttgtc caaactcatc aatgtatctt atcatgtctg gactccgcgg ggccctccgc    3300
gcctacagct caagccacat ccgaaggggg agggagccgg gagctgcgcg cggggccgcc    3360 gggggggaggg gtggcaccgc ccacgccggg cggccacgaa gggcggggca gcggcgcgc    3420 gcgcggcggg gggagggggcc ggcgccgcgc ccgctgggaa ttggggccct aggggggggg    3480
cggaggcgcc gacgaccgcg gcacttaccg ttcgcggcgt ggcgcccggt ggtccccaag    3540
gggagggaag ggggaggcgg ggcgaggaca gtgaccggag tctcctcagc ggtggcttt     3600 ctgcttggca gcctcagcgg ctggcgccaa aaccggactc cgcccacttc ctcgcccgcc    3660
ggtgcgaggg tgtggaatcc tccagacgct gggggagggg gagttgggag cttaaaaact    3720
agtacccctt tgggaccact ttcagcagcg aactctcctg tacaccaggg gtcagttcca    3780
cagacgcggg ccaggggtgg gtcattgcgg cgtgaacaat aatttgacta gaagttgatt    3840
cgggtgtttc cggaagggc cgagtcaatc gccgagttg gggcacgaaa acaaaaagg      3900 gaaggctact aagattttc tggcgggggt tatcattggc gtaactgcag ggaccacctc    3960
ccgggttgag ggggctggat ctccaggctg cggattaagc ccctcccgtc ggcgttaatt    4020
tcaaactgcg cgacgtttct cacctgcctt cgccaaggca ggggccggga ccctattcca    4080
agaggtagta actagcagga ctctagcctt ccgcaattca ttgagcgcat ttacggaagt    4140
aacgtcgggt actgtctctg gccgcaaggg tgggaggagt acgcatttgg cgtaaggtgg    4200
ggcgtagagc cttcccgcca ttggcggcgg atagggcgtt tacgcgacgg cctgacgtag    4260
```

| | |
|---|---|
| cggaagacgc cttagtgggg gggaaggttc tagaaaagcg gcggcagcgg ctctagcggc | 4320 |
| agtagcagca gcgccgggtc ccgtgcgag gtgctcctcg cagagttgtt tctccagcag | 4380 |
| cggcagttct cactacagcg ccaggacgag tccggttcgt gttcgtccgc ggagatctct | 4440 |
| ctcatctcgc tcggctgcgg gaaatcgggc tgaagcgact gagtccgcga tggaggtaac | 4500 |
| gggtttgaaa tcaatgagtt attgaaaagg gcatggcgag gccgttggcg cctcagtgga | 4560 |
| agtcggccag ccgcctccgt gggagagagg caggaaatcg gaccaattca gtagcagtgg | 4620 |
| ggcttaaggt ttatgaacgg ggtcttgagc ggaggcctga gcgtacaaac agcttcccca | 4680 |
| ccctcagcct cccggcgcca tttcccttca ctggggtgg gggatgggga ctttcacat | 4740 |
| ggcggacgct gccccgctgg ggtgaaagtg gggcgcggag gcgggacttc ttattccctt | 4800 |
| tctaaagcac gctgcttcgg gggccacggc gtctcctcgg aaccggttgt ggaatgtgtg | 4860 |
| tcagttaggg tgtggaaagt ccccaggctc cccagcaggc agaagtatgc aaagcatgca | 4920 |
| tctcaattag tcagcaacca ggtgtggaaa gtccccaggc tccccagcag gcagaagtat | 4980 |
| gcaaagcatg catctcaatt agtcagcaac catagtcccg cccctaactc cgcccatccc | 5040 |
| gccctaact ccgcccagtt ccgcccattc tccgccccat ggctgactaa ttttttttat | 5100 |
| ttatgcagag gccgaggccg cctcggcctc tgagctattc cagaagtagt gaggaggctt | 5160 |
| ttttggaggc ctaggctttt gcaaaaaagc tgcagatgat tgaacaagat ggattgcacg | 5220 |
| caggttctcc ggccgcttgg gtggagaggc tattcggcta tgactgggca acagacaa | 5280 |
| tcggctgctc tgatgccgcc gtgttccggc tgtcagcgca ggggcgcccg gttcttttg | 5340 |
| tcaagaccga cctgtccggt gccctgaatg aactgcagga cgaggcagcg cggctatcgt | 5400 |
| ggctggccac gacgggcgtt ccttgcgcag ctgtgctcga cgttgtcact gaagcgggaa | 5460 |
| gggactggct gctattgggc gaagtgccgg ggcaggatct cctgtcatct caccttgctc | 5520 |
| ctgccgagaa agtatccatc atggctgatg caatgcggcg gctgcatacg cttgatccgg | 5580 |
| ctacctgccc attcgaccac caagcgaaac atcgcatcga gcgagcacgt actcggatgg | 5640 |
| aagccggtct tgtcgatcag gatgatctgg acgaagagca tcaggggctc gcgccagccg | 5700 |
| aactgttcgc caggctcaag gcgcgcatgc ccgacgcga ggatctcgtc gtgacccatg | 5760 |
| gcgatgcctg cttgccgaat atcatggtgg aaaatggccg cttttctgga ttcatcgact | 5820 |
| gtggccggct gggtgtggcg gaccgctatc aggacatagc gttggctacc cgtgatattg | 5880 |
| ctgaagagct tggcggcgaa tgggctgacc gcttcctcgt gctttacggt atcgccgctc | 5940 |
| ccgattcgca gcgcatcgcc ttctatcgcc ttcttgacga gttcttctga tccgtgac | 6000 |
| ataattggac aaactaccta cagagattta agctctaag gtaaatataa aattttttaag | 6060 |
| tgtataatgt gttaaactac tgattctaat tgtttgtgta ttttagattc caacctatgg | 6120 |
| aactgatgaa tgggagcagt ggtggaatgc ctttaatgag gaaaacctgt tttgctcaga | 6180 |
| agaaatgcca tctagtgatg atgaggctac tgctgactct caacattcta ctcctccaaa | 6240 |
| aaagaagaga aaggtagaag accccaagga ctttccttca gaattgctaa gttttttgag | 6300 |
| tcatgctgtg tttagtaata gaactcttgc ttgctttgct atttacacca caaggaaaa | 6360 |
| agctgcactg ctatacaaga aaattatgga aaaatattct gtaacctta taagtaggca | 6420 |
| taacagttat aatcataaca tactgttttt tcttactcca cacaggcata gagtgtctgc | 6480 |
| tattaataac tatgctcaaa aattgtgtac ctttagcttt ttaatttgta aaggggttaa | 6540 |
| taaggaatat ttgatgtata gtgccttgac tagagatcat aatcagccat accacatttg | 6600 |
| tagaggtttt acttgcttta aaaaacctcc cacacctccc cctgaacctg aaacataaaa | 6660 |

```
tgaatgcaat tgttgttgtt aacttgttta ttgcagctta taatggttac aaataaagca    6720
atagcatcac aaatttcaca aataaagcat ttttttcact gcattctagt tgtggtttgt    6780
ccaaactcat caatgtatct tatcatgtct gggcccatcg atgccgacgt agcgcctgat    6840
gcggtatttt ctccttacgc atctgtgcgg tatttcacac cgcatatggt gcactctcag    6900
tacaatctgc tctgatgccg catagttaag ccagccccga cacccgccaa cacccgctga    6960
cgcgccctga cgggcttgtc tgctcccggc atccgcttac agacaagctg tgaccgtctc    7020
cgggagctgc atgtgtcaga ggttttcacc gtcatcaccg aaacgcgcga dacgaaaggg    7080
cctcgtgata cgcctatttt tataggttaa tgtcatgata taatggttt cttagacgtc    7140
aggtggcact tttcggggaa atgtgcgcgg aacccctatt tgtttatttt tctaaataca    7200
ttcaaatatg tatccgctca tgagacaata accctgataa atgcttcaat aatattgaaa    7260
aaggaagagt atgagtattc aacatttccg tgtcgccctt attcccttt ttgcggcatt    7320
ttgccttcct gttttgctc acccagaaac gctggtgaaa gtaaaagatg ctgaagatca    7380
gttgggtgca cgagtgggtt acatcgaact ggatctcaac agcggtaaga tccttgagag    7440
ttttcgcccc gaagaacgtt ttccaatgat gagcactttt aaagttctgc tatgtggcgc    7500
ggtattatcc cgtattgacg ccgggcaaga gcaactcggt cgccgcatac actattctca    7560
gaatgacttg gttgagtact caccagtcac agaaaagcat cttacggatg gcatgacagt    7620
aagagaatta tgcagtgctg ccataaccat gagtgataac actgcggcca acttacttct    7680
gacaacgatc ggaggaccga aggagctaac cgcttttttg cacaacatgg ggatcatgt    7740
aactcgcctt gatcgttggg aaccggagct gaatgaagcc ataccaaacg acgagcgtga    7800
caccacgatg cctgtagcaa tggcaacaac gttgcgcaaa ctattaactg gcgaactact    7860
tactctagct tcccggcaac aattaataga ctggatggag gcggataaag ttgcaggacc    7920
acttctgcgc tcggcccttc cggctggctg gtttattgct gataaatctg gagccggtga    7980
gcgtgggtct cgcggtatca ttgcagcact ggggccagat ggtaagccct cccgtatcgt    8040
agttatctac acgacgggga gtcaggcaac tatggatgaa cgaaatagac agatcgctga    8100
gataggtgcc tcactgatta agcattggta actgtcagac caagtttact catatatact    8160
ttagattgat ttaaaacttc atttttaatt taaaaggatc taggtgaaga tccttttga    8220
taatctcatg accaaaatcc cttaacgtga gttttcgttc cactgagcgt cagacccgt    8280
agaaaagatc aaaggatctt cttgagatcc ttttttctg cgcgtaatct gctgcttgca    8340
aacaaaaaa ccaccgctac cagcggtggt ttgtttgccg gatcaagagc taccaactct    8400
ttttccgaag gtaactggct tcagcagagc gcagatacca aatactgttc ttctagtgta    8460
gccgtagtta ggccaccact tcaagaactc tgtagcaccg cctacatacc tcgctctgct    8520
aatcctgtta ccagtggctg ctgccagtgg cgataagtcg tgtcttaccg ggttggactc    8580
aagacgatag ttaccggata aggcgcagcg gtcgggctga acgggggtt cgtgcacaca    8640
gcccagcttg gagcgaacga cctacaccga actgagatac ctacagcgtg agctatgaga    8700
aagcgccacg cttcccgaag ggagaaaggc ggacaggtat ccggtaagcg cagggtcgg    8760
aacaggagag cgcacgaggg agcttccagg gggaaacgcc tggtatcttt atagtcctgt    8820
cgggtttcgc cacctctgac ttgagcgtcg attttgtga tgctcgtcag ggggggcggag    8880
cctatggaaa aacgccagca acgcggcctt tttacggttc ctggcctttt gctggccttt    8940
tgctcacatg ttctttcctg cgttatcccc tgattctgtg gataaccgta ttaccgcctt    9000
```

-continued

```
tgagtgagct gataccgctc gccgcagccg aacgaccgag cgcagcgagt cagtgagcga    9060
ggaagcggaa gagcgcccaa tacgcaaacc gcctctcccc gcgcgttggc cgattcatta    9120
atgcagctgg gccctccgcg cctacagctc aagccacatc cgaaggggga gggagccggg    9180
agctgcgcgc ggggccgccg gggggagggg tggcaccgcc cacgccgggc ggccacgaag    9240
ggcggggcag cgggcgcgcg cgcggcgggg ggaggggccg gcgccgcgcc cgctgggaat    9300
tggggcccta gggggagggc ggaggcgccg acgaccgcgg cacttaccgt tcgcggcgtg    9360
gcgcccggtg gtccccaagg ggagggaagg gggaggcggg gcgaggacag tgaccggagt    9420
ctcctcagcg gtggctttc tgcttggcag cctcagcggc tggcgccaaa accggactcc     9480
gcccacttcc tcgcccgccg gtgcgagggt gtggaatcct ccagacgctg ggggaggggg    9540
agttgggagc ttaaaaacta gtaccccttt gggaccactt tcagcagcga actctcctgt    9600
acaccagggg tcagttccac agacgcgggc caggggtggg tcattgcggc gtgaacaata    9660
atttgactag aagttgattc gggtgtttcc ggaaggggcc gagtcaatcc gccgagttgg    9720
ggcacggaaa acaaaaaggg aaggctacta agatttttct ggcgggggtt atcattggcg    9780
taactgcagg gaccacctcc cgggttgagg gggctggatc tccaggctgc ggattaagcc    9840
cctcccgtcg gcgttaattt caaactgcgc gacgtttctc acctgccttc gccaaggcag    9900
gggccgggac cctattccaa gaggtagtaa ctagcaggac tctagccttc gcaattcat    9960
tgagcgcatt tacggaagta acgtcgggta ctgtctctgg ccgcaagggt gggaggagta   10020
cgcatttggc gtaaggtggg gcgtagagcc ttcccgccat ggcggcgga tagggcgttt    10080
acgcgacggc ctgacgtagc ggaagacgcc ttagtggggg ggaaggttct agaaaagcgg   10140
cggcagcggc tctagcggca gtagcagcag cgccgggtcc cgtgcggagg tgctcctcgc   10200
agagttgttt ctccagcagc ggcagttctc actacagcgc caggacgagt ccggttcgtg   10260
ttcgtccgcg gagatctctc tcatctcgct cggctgcggg aaatcgggct gaagcgactg   10320
agtccgcgat ggaggtaacg ggtttgaaat caatgagtta ttgaaaaggg catggcgagg   10380
ccgttggcgc ctcagtggaa gtcggccagc cgcctccgtg ggagagaggc aggaaatcgg   10440
accaattcag tagcagtggg gcttaaggtt tatgaacggg gtcttgagcg gaggcctgag   10500
cgtacaaaca gcttccccac cctcagcctc ccggcgccat ttcccttcac tgggggtggg   10560
ggatggggag ctttcacatg gcggacgctg ccccgctggg gtgaaagtgg ggcgcggagg   10620
cgggacttct tattccctt ctaaagcacg ctgcttcggg ggccacggcg tctcctcgga    10680
aagctt                                                              10686
```

<210> SEQ ID NO 11
<211> LENGTH: 728
<212> TYPE: DNA
<213> ORGANISM: Artificial Sequence
<220> FEATURE:
<223> OTHER INFORMATION: cDNA encoding human omalizumab antibody (OKLH) light chain to be substitued for the sequence from No. 658 to No. 668 in pNC32c-U533

<400> SEQUENCE: 11

```
cgcgccacca tgggttggtc ttgtatcatc ttatttttag ttgctactgc tactggtgtt      60
cattctgata tacagctcac ccaaagccca tcatctctgt ctgcaagcgt cggcgacagg     120
gtgaccatta cctgtcgcgc aagccaaagc gttgactacg acggcgacag ctacatgaac     180
tggtaccagc agaagcccgg caaggctcct aagctgctga tctatgccgc tcctacctt      240
gaatctggag tgccttctcg tttttccggc tcagggtccg gaactgattt taccctgacc     300
```

```
atttcctccc tccagcccga ggattttgcc acttactact gtcagcagtc ccacgaggac     360
ccatatacat tcggacaagg tacaaaggta gaaatcaagc gtacggtggc tgccccatcc     420
gtgttcatat ttcctcctag cgacgaacaa ctcaagtccg gtaccgccag cgtggtctgc     480
ctgttgaaca atttttatcc aagagaagct aaggtccagt ggaaggttga caacgcccct     540
cagtccggaa atagccaaga gagcgtcacc gaacaggact ccaaggacag tacatactca     600
ctgagctcta cactgaccct ttctaaggcc gactacgaga agcacaaggt ctacgcatgc     660
gaagtgaccc atcagggact cagtagccct gtaacaaaga gttttaatcg aggcgagtgc     720
taagcgat                                                             728

<210> SEQ ID NO 12
<211> LENGTH: 1429
<212> TYPE: DNA
<213> ORGANISM: Artificial Sequence
<220> FEATURE:
<223> OTHER INFORMATION: cDNA encoding human omalizumab antibody (OKLH)
      heavy chain to be substitued for the sequence from No. 3081 to No.
      3092 in pNC32c-U533

<400> SEQUENCE: 12
ggccgccacc atggaatttg gtttatcttg gttttttta gttgctttat aagaggtgt       60 tcaatgtgag gtgcagttgg tcgaatccgg cggcggactc gtgcaaccag gcggaagttt    120
gcggctgtcc tgcgcagtgt ctggttacag catcacctcc gggtatagct ggaactggat    180
ccgccaggct cctggaaagg gcttgagtg ggtggcttcc attacctacg acggctccac    240
taactataac ccgagcgtca aggcagaat caccatctct cgggacgact caaagaatac    300
cttctacctg cagatgaact cactgagggc cgaagatacc gcagtttact actgcgccag    360
ggggtcccac tatttcggcc actggcactt cgccgtgtgg ggacagggca cactcgtgac    420
cgttagtagc gctagcacca aaggccctc tgtgttccca cttgctccct ccagtaaatc    480
tacctccgga ggaaccgcag ccctcggctg cctggtgaag gattacttcc cagagcccgt    540
caccgtctct tggaactccg gagccttgac tagcggagtg cacactttcc ctgctgtatt    600
gcagtccagc ggcttgtatt cactgagtag cgtcgtcacc gtgccttcaa gcagcctcgg    660
gacacagaca tacatatgta atgtcaacca taagccatca aacactaaag ttgataaaaa    720
ggtggaacct aagagttgcg ataagaccca tacctgtcct ccttgccctg ctcctgagct    780
gctgggaggc cctagcgtgt ttctgttccc ccccaagccc aaagatacac tgatgatttc    840
ccgcacacct gaagtaacat gtgtcgtggt tgatgtgagt cacgaggatc cagaggtcaa    900
gtttaattgg tacgtggacg gagtggaggt gcacaacgct aagactaagc ctcgggagga    960
acagtacaac agcacatacc gcgtggtcag cgttttgact gtgctgcatc aagactggct   1020
caatggaaag gaatacaagt gcaaggtctc taataaagcc ctccccgctc ctattgagaa   1080
gactatttct aaagccaagg gccagcctcg cgaacctcag gtatatactt tgccaccctc   1140
tcgcgaagaa atgacaaaga atcaggtctc actcacttgc ctcgtcaaag gttttaccc   1200 ttctgacatc gctgtcgaat gggaaagtaa tggtcagcca gaaaacaatt acaagactac   1260
tccaccagtg ctcgattctg atggaagttt ctttctctac agtaagctca ctgtggacaa   1320
atctcgctgg cagcaggta acgtattctc atgctccgtg atgcatgaag ccctccacaa   1380
ccattacacc cagaagagcc tgtctctgag cccaggcaag taacctgca              1429

<210> SEQ ID NO 13
```

```
<211> LENGTH: 24
<212> TYPE: DNA
<213> ORGANISM: Artificial Sequence
<220> FEATURE:
<223> OTHER INFORMATION: BstBI recognition site-containing sequence to
      be substituted for the sequence from No. 5309 to No. 5311 in
      UCOE-Hu-P

<400> SEQUENCE: 13
cctagtagta gtagtagttc gaag                                          24

<210> SEQ ID NO 14
<211> LENGTH: 3400
<212> TYPE: DNA
<213> ORGANISM: Artificial Sequence
<220> FEATURE:
<223> OTHER INFORMATION: cDNA encoding human omalizumab antibody light
      chain (OML) linking to cDNA encoding Simian Virus 40
      polyadenylation signal (SV40pA), guinea pig cytomegalovirus
      promoter (PgpCMV) and human omalizumab antibody heavy chain (OMH)

<400> SEQUENCE: 14
cccaccatgg gttggtcttg tatcatctta ttttttagttg ctactgctac tggtgttcat     60
tctgatatac agctcaccca aagcccatca tctctgtctg caagcgtcgg cgacagggtg    120
accattacct gtcgcgcaag ccaaagcgtt gactacgacg gcgacagcta catgaactgg    180
taccagcaga agcccggcaa ggctcctaag ctgctgatct atgccgcctc ctaccttgaa    240
tctggagtgc cttctcgttt ttccggctca gggtccggaa ctgatttac cctgaccatt     300 tcctccctcc agcccgagga ttttgccact tactactgtc agcagtccca cgaggaccca    360
tatacattcg acaaggtac aaaggtagaa atcaagcgta cggtggctgc cccatccgtg     420
ttcatatttc ctcctagcga cgaacaactc aagtccggta ccgccagcgt ggtctgcctg    480
ttgaacaatt tttatccaag agaagctaag gtccagtgga aggttgacaa cgcccttcag    540
tccggaaata gccaagagag cgtcaccgaa caggactcca aggacagtac atactcactg    600
agctctacac tgaccctttc taaggccgac tacgagaagc acaaggtcta cgcatgcgaa    660
gtgacccatc agggactcag tagccctgta caaaagagtt ttaatcgagg cgagtgctaa    720
gcgatcgcgc tagcgcggcc acgtagtcga ctacgtagag ctcggtaccc ggggatcctc    780
tagagtcgac ctgcaggcat gcaagctggc cgcgactcta gatcataatc agccatacca    840
catttgtaga ggttttactt gctttaaaaa acctcccaca cctccccctg aacctgaaac    900
ataaaatgaa tgcaattgtt gttgttaact tgtttattgc agcttataat ggttacaaat    960 aaaagcaatag catcacaaat ttcacaaata aagcattttt tcactgcat tctagttgtg   1020 gtttgtccaa actcatcaat gtatcttaac cggttatgtt acttggcaga ggccgcatgg   1080
aaagtccctg gacgtgggac atctgattaa tacgtgagga ggtcagccat gttcttttg    1140 gcaaaggact acggtcattg gacgtttgat tggcatggga tagggtcagc cagagttaac   1200
agtgttcttt tggcaaaggg atacgtgaaa agtcccggc cattttacagt aaactgatac   1260 ggggacaaag cacagccata tttagtcatg tattgcttgg cagagggtct atggaaagtc   1320
cctggacgtg ggacgtctga ttaatatgaa agaaggtcag ccagaggtag ctgtgtcctt   1380
tttggcaaag ggatacggtt atgggacgtt tgattggact gggatagggt cagccagagt   1440
taacagtgtt cttttggcaa aggaaacgtg gaaagtcccg gccatttac agtaaactga    1500 tactgggaca agtacaccc atatttagtc atgttctttt tggcaaagag catctggaaa    1560
gtcccgggca gcattatagt cacttggcag agggaaaggg tcactcagag ttaagtacat   1620
```

-continued

```
ctttccaggg ccaatattcc agtaaattac acttagtttt atgcaaatca gccacaaagg    1680
ggatttccc ggtcaattat gacttttcc ttagtcatgc ggtatccaat tactgccaaa     1740
ttggcagtac atactaggtg attcactgac atttggccgt cctctggaaa gtccctggaa    1800
accgctcaag tactgtatca tggtgacttt gcatttttgg agagcacgcc ccactccacc    1860
attggtccac gtaccctatg ggggagtggt ttatgagtat ataaggggct ccggtttaga    1920
agccgggcag agcggaattc gagctccctg caggttagtt aagttaacgg cgcgccacca    1980
tggaatttgg tttatcttgg gttttttag ttgctttatt aagaggtgtt caatgtgagg    2040
tgcagttggt cgaatccggc ggcggactcg tgcaaccagg cggaagtttg cggctgtcct    2100
gcgcagtgtc tggttacagc atcacctccg ggtatagctg gaactggatc cgccaggctc    2160
ctggaaaggg gcttgagtgg gtggcttcca ttacctacga cggctccact aactataacc    2220
cgagcgtcaa aggcagaatc accatctctc gggacgactc aaagaatacc ttctacctgc    2280
agatgaactc actgagggcc gaagataccg cagtttacta ctgcgccagg ggtcccact    2340
atttcggcca ctggcacttc gccgtgtggg gacagggcac actcgtgacc gttagtagcg    2400
ctagcaccaa aggcccctct gtgttccac ttgctccctc cagtaaatct acctccggag    2460
gaaccgcagc cctcggctgc ctggtgaagg attacttccc agagcccgtc accgtctctt    2520
ggaactccgg agccttgact agcggagtgc acactttccc tgctgtattg cagtccagcg    2580
gcttgtattc actgagtagc gtcgtcaccg tgccttcaag cagcctcggg acacagacat    2640
acatatgtaa tgtcaaccat aagccatcaa acactaaagt tgataaaaag gtggaaccta    2700
agagttgcga taagacccat acctgtcctc cttgccctgc tcctgagctg ctgggaggcc    2760
ctagcgtgtt tctgttcccc cccaagccca agatacact gatgatttcc cgcacacctg    2820
aagtaacatg tgtcgtggtt gatgtgagtc acgaggatcc agaggtcaag tttaattggt    2880
acgtggacgg agtggaggtg cacaacgcta agactaagcc tcgggaggaa cagtacaaca    2940
gcacataccg cgtggtcagc gttttgactg tgctgcatca agactggctc aatggaaagg    3000
aatacaagtg caaggtctct aataaagccc tccccgctcc tattgagaag actatttcta    3060
aagccaaggg ccagcctcgc gaacctcagg tatatacttt gccaccctct cgcgaagaaa    3120
tgacaaagaa tcaggtctca ctcacttgcc tcgtcaaagg gttttaccct tctgacatcg    3180
ctgtcgaatg ggaaagtaat ggtcagccag aaaacaatta caagactact ccaccagtgc    3240
tcgattctga tggaagtttc tttctctaca gtaagctcac tgtggacaaa tctcgctggc    3300
agcagggtaa cgtattctca tgctccgtga tgcatgaagc cctccacaac cattacaccc    3360
agaagagcct gtctctgagc ccaggcaagt aatctagatt                          3400
```

<210> SEQ ID NO 15
<211> LENGTH: 394
<212> TYPE: PRT
<213> ORGANISM: Canis lupus

<400> SEQUENCE: 15

Met Ala Gly Phe Gly Phe Arg Arg His Gly Ala Gln Pro Asp Leu Ala
1               5                   10                  15

Ser Arg Thr Trp Pro Cys Thr Ala Leu Phe Ser Leu Leu Phe Ile Pro
            20                  25                  30

Val Phe Ser Lys Gly Met His Val Ala Gln Pro Ala Val Val Leu Ala
        35                  40                  45

Ser Ser Arg Gly Val Ala Ser Phe Val Cys Glu Tyr Gly Ser Ser Gly
    50                  55                  60

Asn Ala Ala Glu Val Arg Val Thr Val Leu Arg Gln Ala Gly Ser Gln
65                  70                  75                  80

Met Thr Glu Val Cys Ala Ala Thr Tyr Thr Val Glu Asp Glu Leu Ala
                85                  90                  95

Phe Leu Asp Asp Ser Thr Cys Thr Gly Thr Ser Gly Asn Lys Val
            100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Val Gly Met Gly
130                 135                 140

Asn Gly Thr Gln Ile Tyr Val Ile Asp Pro Glu Pro Cys Pro Asp Ser
145                 150                 155                 160

Asp Pro Lys Glu Ser Thr Cys Lys Cys Ile Ser Pro Cys Pro Val Pro
                165                 170                 175

Glu Ser Leu Gly Gly Pro Ser Val Phe Ile Phe Pro Pro Lys Pro Lys
            180                 185                 190

Asp Ile Leu Arg Ile Thr Arg Thr Pro Glu Ile Thr Cys Val Val Leu
            195                 200                 205

Asp Leu Gly Arg Glu Asp Pro Glu Val Gln Ile Ser Trp Phe Val Asp
210                 215                 220

Gly Lys Glu Val His Thr Ala Lys Thr Gln Pro Arg Glu Gln Gln Phe
225                 230                 235                 240

Asn Ser Thr Tyr Arg Val Val Ser Val Leu Pro Ile Glu His Gln Asp
                245                 250                 255

Trp Leu Thr Gly Lys Glu Phe Lys Cys Arg Val Asn His Ile Gly Leu
            260                 265                 270

Pro Ser Pro Ile Glu Arg Thr Ile Ser Lys Ala Arg Gly Gln Ala His
            275                 280                 285

Gln Pro Ser Val Tyr Val Leu Pro Pro Ser Pro Lys Glu Leu Ser Ser
290                 295                 300

Ser Asp Thr Val Thr Leu Thr Cys Leu Ile Lys Asp Phe Phe Pro Pro
305                 310                 315                 320

Glu Ile Asp Val Glu Trp Gln Ser Asn Gly Gln Pro Glu Pro Glu Ser
                325                 330                 335

Lys Tyr His Thr Thr Ala Pro Gln Leu Asp Glu Asp Gly Ser Tyr Phe
            340                 345                 350

Leu Tyr Ser Lys Leu Ser Val Asp Lys Ser Arg Trp Gln Gln Gly Asp
            355                 360                 365

Thr Phe Thr Cys Ala Val Met His Glu Ala Leu Gln Asn His Tyr Thr
370                 375                 380

Asp Leu Ser Leu Ser His Ser Pro Gly Lys
385                 390

<210> SEQ ID NO 16
<211> LENGTH: 1185
<212> TYPE: DNA
<213> ORGANISM: Artificial Sequence
<220> FEATURE:
<223> OTHER INFORMATION: Codon-optimized nucleotide sequence encoding
      canis lupus CTLA-4-Ig

<400> SEQUENCE: 16
atggctggat tggattcag aaggcacgga gcccagcccg acctggcatc tcgcacttgg      60
ccctgtaccg cactgttttc actgctgttc atcccagtgt tcagcaaggg aatgcacgtg     120

| | |
|---|---|
| gctcagccag ctgtggtgct ggcttccagc agaggcgtgg cttccttcgt gtgcgagtac | 180 |
| ggctcttccg gcaacgccgc tgaggtgaga gtgaccgtgc tgaggcaggc tggctcccag | 240 |
| atgacagagg tgtgcgccgc tacctataca gtggaggacg agctggcttt cctggacgat | 300 |
| agcacctgta caggcaccag ctctggcaac aaggtcaatc tgaccatcca gggcctgcgc | 360 |
| gccatggata caggcctgta catctgtaag gtggagctga tgtatccccc tccatactat | 420 |
| gtgggcatgg gcaatggcac ccagatctac gtgatcgacc ccgagccttg cccagactct | 480 |
| gatccaaagg agtcgacatg caagtgtatc tctccatgtc ctgtgccaga gagcctggga | 540 |
| ggaccttccg tgttcatctt tccccctaag ccaaaggata tcctgaggat cacacggacc | 600 |
| cctgagatca cctgcgtggt gctggacctg ggaagggagg atccagaggt gcagatctcc | 660 |
| tggttcgtgg acggcaagga ggtgcatacc gctaagacac agcccagaga gcagcagttt | 720 |
| aactccacct atcgcgtggt gagcgtgctg cctatcgagc accaggattg gctgacaggc | 780 |
| aaggagttta gtgccgggt gaatcatatc ggcctgccct ctcctatcga gaggaccatc | 840 |
| tccaaggcta ggggacaggc tcaccagcca agcgtgtacg tgctgccacc ctctcctaag | 900 |
| gagctgtcca gctctgacac agtgaccctg acatgtctga tcaaggactt ctttcctcca | 960 |
| gagatcgacg tggagtggca gtccaacggc agccagagc cgagagcaa gtatcatacc | 1020 |
| acagcccccc agctggacga ggatggctct tacttcctgt attccaagct gagcgtggac | 1080 |
| aagtccaggt ggcagcaggg cgatacccttt acatgtgctg tgatgcacga agccctgcag | 1140 |
| aatcattaca ccgacctgtc actgtcccac tcccctggca ataa | 1185 |

<210> SEQ ID NO 17
<211> LENGTH: 8444
<212> TYPE: DNA
<213> ORGANISM: Artificial Sequence
<220> FEATURE:
<223> OTHER INFORMATION: pDC62c5-U533 containing one cloning site

<400> SEQUENCE: 17

| | |
|---|---|
| cgatgtacgg gccagatata cgcgttgaca ttgattattg actagtcgcg ttacataact | 60 |
| tacggtaaat ggcccgcctg gctgaccgcc caacgacccc cgcccattga cgtcaataat | 120 |
| gacgtatgtt cccatagtaa cgccaatagg gactttccat tgacgtcaat gggtggagta | 180 |
| tttacggtaa actgcccact tggcagtaca tcaagtgtat catatgccaa gtccgccccc | 240 |
| tattgacgtc aatgacggta aatggcccgc ctggcattat gcccagtaca tgaccttacg | 300 |
| ggactttcct acttggcagt acatctacgt attagtcatc gctattacca tggtgatgcg | 360 |
| gttttggcag tacaccaatg ggcgtggata gcggtttgac tcacggggat ttccaagtct | 420 |
| ccacccatt gacgtcaatg ggagtttgtt ttggcaccaa aatcaacggg actttccaaa | 480 |
| atgtcgtaat aaccccgccc cgttgacgca aatgggcggt aggcgtgtac ggtgggaggt | 540 |
| ctatataagc agagctcgtt tagtgaaccg tcagatcctc actctcttcc gcatcgctgt | 600 |
| ctgcgagggc cagctgttgg gctcgcggtt gaggacaaac tcttcgcggt ctttccagta | 660 |
| ctcttggatc ggaaacccgt cggcctccga acggtactcc gccaccgagg gacctgagcg | 720 |
| agtccgcatc gaccggatcg gaaaacctct cgagaaaggc gtctaaccag tcacagtcgc | 780 |
| aaggtaggct gagcaccgtg gcgggcggca gcgggtggcg gtcggggttg tttctggcgg | 840 |
| aggtgctgct gatgatgtaa ttaaagtagg cggtcttgag acggcggatg gtcgaggtga | 900 |
| ggtgtggcag gcttgagatc cagctgttgg ggtgagtact ccctctcaaa agcgggcatg | 960 |
| acttctgcgc taagattgtc agtttccaaa aacgaggagg atttgatatt cacctggccc | 1020 |

```
gatctggcca tacacttgag tgacaatgac atccactttg cctttctctc cacaggtgtc  1080
cactcccagg tccaaggcgc gccgcgatcg cgcctcgact gtgccttcta gttgccagcc  1140
atctgttgtt tgcccctccc ccgtgccttc cttgaccctg gaaggtgcca ctcccactgt  1200
cctttcctaa taaaatgagg aaattgcatc gcattgtctg agtaggtgtc attctattct  1260
ggggggtggg gtgggcagg acagcaaggg ggaggattgg gaagacaata gcaggcatgc   1320
tgggaggat ctccgcgggg ccctccgcgc ctacagctca agccacatcc gaaggggag    1380
ggagccggga gctgcgcgcg gggccgccgg ggggagggt ggcaccgccc acgccgggcg   1440
gccacgaagg gcgggcagc gggcgcgcgc gcggcggggg gaggggccgg cgccgcgccc   1500
gctgggaatt ggggccctag ggggagggcg gaggcgccga cgaccgcggc acttaccgtt  1560
cgcggcgtgg cgcccggtgg tccccaaggg gagggaaggg ggaggcgggg cgaggacagt  1620
gaccggagtc tcctcagcgg tggcttttct gcttggcagc ctcagcggct ggcgccaaaa  1680
ccggactccg cccacttcct cgcccgccgg tgcgagggtg tggaatcctc cagacgctgg  1740
gggaggggga gttgggagct taaaaactag taccccttg ggaccacttt cagcagcgaa   1800
ctctcctgta caccagggt cagttccaca gacgcgggcc aggggtgggt cattgcggcg   1860
tgaacaataa tttgactaga agttgattcg ggtgtttccg gaaggggccg agtcaatccg  1920
ccgagttggg gcacggaaaa caaaaaggga aggctactaa gattttctg gcggggtta    1980
tcattggcgt aactgcaggg accacctccc gggttgaggg ggctggatct ccaggctgcg  2040
gattaagccc ctcccgtcgg cgttaatttc aaactgcgcg acgtttctca cctgccttcg  2100
ccaaggcagg ggccgggacc ctattccaag aggtagtaac tagcaggact ctagccttcc  2160
gcaattcatt gagcgcattt acggaagtaa cgtcgggtac tgtctctggc cgcaagggtg  2220
ggaggagtac gcatttggcg taaggtgggg cgtagagcct tcccgccatt ggcggcggat  2280
agggcgttta cgcgacggcc tgacgtagcg gaagacgcct tagtgggggg gaaggttcta  2340
gaaaagcggc ggcagcggct ctagcggcag tagcagcagc gccgggtccc gtgcggaggt  2400
gctcctcgca gagttgtttc tccagcagcg gcagttctca ctacagcgcc aggacgagtc  2460
cggttcgtgt tcgtccgcgg agatctctct catctcgctc ggctgcggga atcgggctg   2520
aagcgactga gtccgcgatg gaggtaacgg gtttgaaatc aatgagttat tgaaaagggc  2580
atggcgaggc cgttggcgcc tcagtggaag tcggccagcc gcctccgtgg gagagaggca  2640
ggaaatcgga ccaattcagt agcagtgggg cttaaggttt atgaacgggg tcttgagcgg  2700
aggcctgagc gtacaaacag cttccccacc ctcagcctcc cggcgccatt tcccttcact  2760
gggggtgggg gatggggagc tttcacatgg cggacgctgc cccgctgggg tgaaagtggg  2820
gcgcggaggc gggacttctt attcccttc taaagcacgc tgcttcgggg gccacggcgt   2880
ctcctcggag aattcaaatg ggaccggttg tggaatgtgt gtcagttagg gtgtggaaag  2940
tccccaggct ccccagcagg cagaagtatg caaagcatgc atctcaatta gtcagcaacc  3000
atagtcccgc ccctaactcc gcccatcccg ccctaactc cgcccagttc cgcccattct   3060
ccgcccatg gctgactaat ttttttatt tatgcagagg ccgaggccgc ctcggcctct    3120
gagctattcc agaagtagtg aggaggcttt tttgaggcc taggcttttg caaaaaagct   3180
gcagatggta cgaccattaa attgtattgt agcagtatca caaaatatgg gtattggtaa  3240
aaatggtgat ttaccatggc caccattacg aaatgaattt aaatatttc aacgaatgac   3300
tactacttca tcagtagaag gtaaacaaaa tttagtaatt atgggtcgaa aaacttggtt  3360
```

```
ttcaattcct gagaagaatc gacctttaaa ggacagaatt aatatagttc tcagtagaga   3420
actcaaagaa ccaccacgag gagctcattt tcttgccaaa agtttggatg atgccttaag   3480
acttattgaa caaccggaat tggcaagtaa agtagacatg gtttggatag tcggaggcag   3540
ttctgtttac caggaagcca tgaatcaacc aggccacctc agactctttg tgacaaggat   3600
catgcaggaa tttgaaagtg acacgttttt cccagaaatt gatttgggga aatataaact   3660
tctcccagaa tacccaggcg tcctctctga ggtccaggag gaaaaaggca tcaagtataa   3720
gtttgaagtc tacgagaaga aagactaaag atccgtgaca taattggaca aactacctac   3780
agagatttaa agctctaagg taaatataaa attttttaagt gtataatgtg ttaaactact   3840
gattctaatt gtttgtgtat tttagattcc aacctatgga actgatgaat gggagcagtg   3900
gtggaatgcc tttaatgagg aaaacctgtt ttgctcagaa gaaatgccat ctagtgatga   3960
tgaggctact gctgactctc aacattctac tcctccaaaa aagaagagaa aggtagaaga   4020
ccccaaggac tttccttcag aattgctaag ttttttgagt catgctgtgt ttagtaatag   4080
aactcttgct tgctttgcta tttacaccac aaaggaaaaa gctgcactgc tatacaagaa   4140
aattatggaa aaatattctg taaccttat aagtaggcat aacagttata atcataacat   4200
actgtttttt cttactccac acaggcatag agtgtctgct attaataact atgctcaaaa   4260
attgtgtacc tttagctttt taatttgtaa aggggttaat aaggaatatt tgatgtatag   4320
tgccttgact agagatcata atcagccata ccacatttgt agaggtttta cttgctttaa   4380
aaaacctccc acacctcccc ctgaacctga aacataaaat gaatgcaatt gttgttgtta   4440
acttgtttat tgcagcttat aatggttaca aataaagcaa tagcatcaca aatttcacaa   4500
ataaagcatt ttttcactg cattctagtt gtggtttgtc caaactcatc aatgtatctt   4560
atcatgtctg ggcccatcga tgccgacgta gcgctgatgc ggtattttct ccttacgcat   4620
ctgtgcggta tttcacaccg catatggtgc actctcagta caatctgctc tgatgccgca   4680
tagttaagcc agccccgaca cccgccaaca cccgctgacg cgccctgacg ggcttgtctg   4740
ctcccggcat ccgcttacag acaagctgtg accgtctccg ggagctgcat gtgtcagagg   4800
ttttcaccgt catcaccgaa acgcgcgaga cgaaagggcc tcgtgatacg cctatttta   4860 taggttaatg tcatgataat aatggtttct tagacgtcag gtggcacttt tcggggaaat   4920
gtgcgcggaa cccctatttg tttatttttc taaatacatt caaatatgta tccgctcatg   4980
agacaataac cctgataaat gcttcaataa tattgaaaaa ggaagagtat gagtattcaa   5040
catttccgtg tcgcccttat tccctttttt gcggcatttt gccttcctgt ttttgctcac   5100
ccagaaacgc tggtgaaagt aaaagatgct gaagatcagt tgggtgcacg agtgggttac   5160
atcgaactgg atctcaacag cggtaagatc cttgagagtt ttcgccccga agaacgtttt   5220
ccaatgatga gcacttttaa agttctgcta tgtggcgcgg tattatcccg tattgacgcc   5280
gggcaagagc aactcggtcg ccgcatacac tattctcaga atgacttggt tgagtactca   5340
ccagtcacag aaaagcatct tacggatggc atgacagtaa gagaattatg cagtgctgcc   5400
ataaccatga gtgataacac tgcggccaac ttacttctga caacgatcgg aggaccgaag   5460
gagctaaccg cttttttgca caacatgggg gatcatgtaa ctcgccttga tcgttgggaa   5520
ccggagctga atgaagccat accaaacgac gagcgtgaca ccacgatgcc tgtagcaatg   5580
gcaacaacgt tgcgcaaact attaactggc gaactactta ctctagcttc ccggcaacaa   5640
ttaatagact ggatggaggc ggataaagtt gcaggaccac ttctgcgctc ggcccttccg   5700
gctggctggt ttattgctga taaatctgga gccggtgagc gtgggtctcg cggtatcatt   5760
```

```
gcagcactgg ggccagatgg taagccctcc cgtatcgtag ttatctacac gacgggagt      5820 caggcaacta tggatgaacg aaatagacag atcgctgaga taggtgcctc actgattaag     5880
cattggtaac tgtcagacca agtttactca tatatacttt agattgattt aaaacttcat    5940
ttttaattta aaaggatcta ggtgaagatc cttttgata atctcatgac caaatccct      6000 taacgtgagt tttcgttcca ctgagcgtca gaccccgtag aaaagatcaa aggatcttct    6060
tgagatcctt ttttctgcgc gtaatctgc tgcttgcaaa caaaaaaacc accgctacca    6120
gcggtggttt gtttgccgga tcaagagcta ccaactcttt ttccgaaggt aactggcttc    6180
agcagagcgc agataccaaa tactgttctt ctagtgtagc cgtagttagg ccaccacttc    6240
aagaactctg tagcaccgcc tacatacctc gctctgctaa tcctgttacc agtggctgct    6300
gccagtggcg ataagtcgtg tcttaccggg ttggactcaa gacgatagtt accggataag    6360
gcgcagcggt cgggctgaac ggggggttcg tgcacacagc ccagcttgga gcgaacgacc    6420
tacaccgaac tgagatacct acagcgtgag cattgagaaa gcgccacgct tcccgaaggg    6480
agaaaggcgg acaggtatcc ggtaagcggc agggtcggaa caggagagcg cacgagggag    6540
cttccagggg gaaacgcctg gtatctttat agtcctgtcg ggtttcgcca cctctgactt    6600
gagcgtcgat ttttgtgatg ctcgtcaggg gggcggagcc tatggaaaaa cgccagcaac    6660
gcggcctttt tacggttcct ggccttttgc tggccttttg ctcacatgtt ctttcctgcg    6720 ttatccctg attctgtgga taaccgtatt accgcctttg agtgagctga taccgctcgc    6780
cgcagccgaa cgaccgagcg cagcgagtca gtgagcgagg aagcggaaga gcgcccaata    6840
cgcaaaccgc ctctccccgc gcgttggccg attcattaat gcagctgggc cctccgcgcc    6900
tacagctcaa gccacatccg aagggggagg gagccgggag ctgcgcgcgg ggccgccggg    6960
gggaggggtg gcaccgccca cgccgggcgg ccacgaaggg cggggcagcg ggcgcgcgcg    7020 cggcggggg aggggccggc gccgcgcccg ctgggaattg gggccctagg gggagggcgg    7080
aggcgccgac gaccgcggca cttaccgttc gcggcgtggc gccggtggt ccccaagggg    7140 agggaagggg gaggcgggc gaggacagtg accggagtct cctcagcggt ggcttttctg    7200
cttggcagcc tcagcggctg cgccaaaac cggactccgc ccacttcctc gcccgccggt    7260
gcgagggtgt ggaatcctcc agacgctggg ggaggggag ttgggagctt aaaaactagt    7320 accccttgg gaccactttc agcagcgaac tctcctgtac accaggggtc agttccacag    7380
acgcgggcca ggggtgggtc attgcggcgt gaacaataat ttgactagaa gttgattcgg    7440
gtgtttccgg aaggggccga gtcaatccgc cgagttgggg cacggaaaac aaaaagggaa    7500
ggctactaag atttttctgg cggggttat cattggcgta actgcaggga ccacctcccg    7560
ggttgagggg gctggatctc caggctgcgg attaagcccc tcccgtcggc gttaatttca    7620
aactgcgcga cgtttctcac ctgccttcgc caaggcaggg gccgggaccc tattccaaga    7680
ggtagtaact agcaggactc tagccttccg caattcattg agcgcattta cggaagtaac    7740
gtcgggtact gtctctggcc gcaagggtgg gaggagtacg catttggcgt aaggtggggc    7800
gtagagcctt cccgccattg gcggcggata gggcgtttac gcgacggcct gacgtagcgg    7860
aagacgcctt agtggggggg aaggttctag aaaagcggcg gcagcggctc tagcggcagt    7920
agcagcagcg ccgggtcccg tgcggaggtg ctcctcgcag agttgtttct ccagcagcgg    7980
cagttctcac tacagcgcca ggacgagtcc ggttcgtgtt cgtccgcgga gatctctctc    8040
atctcgctcg gctgcgggaa atcgggctga agcgactgag tccgcgatgg aggtaacggg    8100
```

| | |
|---|---|
| tttgaaatca atgagttatt gaaaagggca tggcgaggcc gttggcgcct cagtggaagt | 8160 |
| cggccagccg cctccgtggg agagaggcag gaaatcggac caattcagta gcagtggggc | 8220 |
| ttaaggttta tgaacggggt cttgagcgga ggcctgagcg tacaaacagc ttccccaccc | 8280 |
| tcagcctccc ggcgccattt cccttcactg ggggtggggg atggggagct ttcacatggc | 8340 |
| ggacgctgcc ccgctggggt gaaagtgggg cgcggaggcg ggacttctta ttccctttct | 8400 |
| aaagcacgct gcttcggggg ccacggcgtc tcctcggaaa gctt | 8444 |

<210> SEQ ID NO 18
<211> LENGTH: 724
<212> TYPE: DNA
<213> ORGANISM: Artificial Sequence
<220> FEATURE:
<223> OTHER INFORMATION: Antibody (TRLH) light chain gene cDNA with
      optimized Kozak sequence added upstream of the initiation codon

<400> SEQUENCE: 18

| | |
|---|---|
| cgcgccccgc cgccaccatg ggttggtctt gtatcatctt atttttagtt gctactgcta | 60 |
| ctggtgttca ttctgatata cagatgaccc aaagcccatc atctctgtct gcaagcgtcg | 120 |
| gcgacagggt gaccattacc tgtcgcgcaa gccaagacgt taatacagca gtggcttggt | 180 |
| accagcagaa gcccggcaag gctcctaagc tgctgatcta tagcgcctcc tttctttatt | 240 |
| ctggagtgcc ttctcgtttt tccggctcaa ggtccggaac tgattttacc ctgaccattt | 300 |
| cctccctcca gcccgaggat tttgccactt actactgtca gcagcactat accacaccac | 360 |
| ctacattcgg acaaggtaca aaggtagaaa tcaagcgtac ggtggctgcc ccatccgtgt | 420 |
| tcatatttcc tcctagcgac gaacaactca gtccggtac cgccagcgtg gtctgcctgt | 480 |
| tgaacaattt ttatccaaga gaagctaagg tccagtggaa ggttgacaac gcccttcagt | 540 |
| ccggaaatag ccaagagagc gtcaccgaac aggactccaa ggacagtaca tactcactga | 600 |
| gctctacact gaccctttct aaggccgact acgagaagca aaggtctac gcatgcgaag | 660 |
| tgacccatca gggactcagt agccctgtaa caaagagttt taatcgaggc gagtgctaag | 720 |
| cgat | 724 |

<210> SEQ ID NO 19
<211> LENGTH: 1430
<212> TYPE: DNA
<213> ORGANISM: Artificial Sequence
<220> FEATURE:
<223> OTHER INFORMATION: Antibody (TRLH) heavy chain gene cDNA with
      optimized Kozak sequence added upstream of the initiation codon

<400> SEQUENCE: 19

| | |
|---|---|
| ggccgccccgc cgccaccatg gaatttggtt tatcttgggt ttttttagtt gctttattaa | 60 |
| gaggtgttca atgtgaggtg cagttggtcg aatccggcgg cggactcgtg caaccaggcg | 120 |
| gaagtttgcg gctgtcctgc gcagcctctg gttttaacat caaagatacc tatattcatt | 180 |
| gggtacgcca ggctcctgga aaggggcttg agtgggtggc tcgaatttac ccaaccaatg | 240 |
| gctacactcg gtatgccgac agcgtcaaag gcagattcac catctctgca gacacatcaa | 300 |
| agaataccgc ttacctgcag atgaactcac tgagggccga agataccgca gtttactact | 360 |
| gctccaggtg gggggggggac ggcttctacg ccatggatta ctggggacag ggcacactcg | 420 |
| tgaccgttag tagcgctagc accaaaggcc cctctgtgtt cccacttgct ccctccagta | 480 |
| aatctacctc cggaggaacc gcagccctcg gctgcctggt gaaggattac ttcccagagc | 540 |
| ccgtcaccgt ctcttggaac tccggagcct tgactagcgg agtgcacact ttccctgctg | 600 |

```
tattgcagtc cagcggcttg tattcactga gtagcgtcgt caccgtgcct tcaagcagcc      660
tcgggacaca gacatacata tgtaatgtca accataagcc atcaaacact aaagttgata      720
aaaaggtgga acctaagagt tgcgataaga cccatacctg tcctccttgc cctgctcctg      780
agctgctggg aggccctagc gtgtttctgt tccccccaa gcccaaagat acactgatga       840
tttcccgcac acctgaagta acatgtgtcg tggttgatgt gagtcacgag gatccagagg      900
tcaagtttaa ttggtacgtg gacggagtgg aggtgcacaa cgctaagact aagcctcggg      960
aggaacagta caacagcaca taccgcgtgg tcagcgtttt gactgtgctg catcaagact     1020
ggctcaatgg aaaggaatac aagtgcaagg tctctaataa agccctcccc gctcctattg     1080
agaagactat ttctaaagcc aagggccagc ctcgcgaacc tcaggtatat actttgccac     1140
cctctcgcga agaaatgaca aagaatcagg tctcactcac ttgcctcgtc aaagggtttt     1200
acccttctga catcgctgtc gaatgggaaa gtaatggtca gccagaaaac aattacaaga     1260
ctactccacc agtgctcgat tctgatggaa gtttctttct ctacagtaag ctcactgtgg     1320
acaaatctcg ctggcagcag ggtaacgtat tctcatgctc cgtgatgcat gaagccctcc     1380
acaaccatta cacccagaag agcctgtctc tgagcccagg ctaacctgca              1430
```